(12) United States Patent
Branca et al.

(10) Patent No.: US 8,268,827 B2
(45) Date of Patent: Sep. 18, 2012

(54) PYRIDAZINONE DERIVATIVES AS PARP INHIBITORS

(75) Inventors: Danila Branca, Rome (IT); Gabriella Dessole, Rome (IT); Federica Ferrigno, Rome (IT); Philip Jones, Rome (IT); Olaf Kinzel, Rome (IT); Samuele Lillini, Rome (IT); Ester Muraglia, Rome (IT); Giovanna Pescatore, Rome (IT); Carsten Schultz-Fademrecht, Oss (NL)

(73) Assignee: Istituto di Ricerche di Biologia Molecolare P. Angeletti SpA., Pomezia, Rome (IT)

( * ) Notice: Subject to any disclaimer, the term of this patent is extended or adjusted under 35 U.S.C. 154(b) by 117 days.

(21) Appl. No.: 12/739,262

(22) PCT Filed: Nov. 14, 2008

(86) PCT No.: PCT/GB2008/051063
§ 371 (c)(1),
(2), (4) Date: Apr. 22, 2010

(87) PCT Pub. No.: WO2009/063244
PCT Pub. Date: May 22, 2009

(65) Prior Publication Data
US 2010/0261709 A1  Oct. 14, 2010

(30) Foreign Application Priority Data
Nov. 15, 2007 (GB) .................................. 0722401.7
Sep. 12, 2008 (GB) .................................. 0816707.4

(51) Int. Cl.
*C07D 401/00* (2006.01)
*A60K 31/50* (2006.01)
(52) U.S. Cl. ............... 514/252.01; 544/234; 544/238
(58) Field of Classification Search ............. 544/234, 544/238; 514/252.01
See application file for complete search history.

(56) References Cited

U.S. PATENT DOCUMENTS

| 2005/0234236 A1 | 10/2005 | Kertesz et al. |
| 2008/0161280 A1 | 7/2008 | Gandhi et al. |
| 2008/0269234 A1 | 10/2008 | Gandhi et al. |
| 2009/0176765 A1 | 7/2009 | Jones et al. |

FOREIGN PATENT DOCUMENTS

| EP | 0714895 | 6/1996 |
| EP | 0810218 | 12/1997 |
| WO | WO02/36576 | 5/2002 |
| WO | WO02/090334 | 11/2002 |
| WO | WO03/093261 | 11/2003 |
| WO | WO2004/080976 | 9/2004 |
| WO | WO2004/085406 | 10/2004 |
| WO | WO2005/090317 | 9/2005 |
| WO | WO2005/097750 | 10/2005 |
| WO | WO2006/021801 | 3/2006 |
| WO | WO 2007/009913 | 1/2007 |
| WO | WO2007/138351 | 12/2007 |
| WO | WO2008/114023 | 9/2008 |
| WO | WO2008/122810 | 10/2008 |
| WO | WO2009/004356 | 1/2009 |

OTHER PUBLICATIONS

McMahon et al.*
Pinedo et al.*
Leeson, et al., Journal of Medicinal Chemistry, American Chemical Society, vol. 32(2), pp. 320-336 (1989).
Jagtap, et al., Nature Reviews Drug Discovery, vol. 4, No. 5, pp. 421-440 (2005).
Bryant, et al., Nature, vol. 434, pp. 913-917 (2005).
Peukert, et al., Exp. Opin. Ther. Patents, vol. 14(11), p. 1531 (2004).
Loh, et al., Bioorganic & Medicinal Chemistry Letters, vol. 15(9), pp. 2235-2238 (2005).
Cockcroft, et al., Bioorganic & Medicinal Chemistry Letters, vol. 16(4), pp. 1040 (2006).
Ishida, et al., Bioorganic and Medicinal Chemistry Letters, vol. 15, p. 4221 (2005).

* cited by examiner

*Primary Examiner* — Paul V. Ward
(74) *Attorney, Agent, or Firm* — Yong Zhao; David A. Muthard; Matthew A. Leff

(57) ABSTRACT

The present invention relates to compounds of formula (I): and pharmaceutically acceptable salts or tautomers thereof which are inhibitors of poly(ADP-ribose)polymerase (PARP) and thus useful for the treatment of cancer, inflammatory diseases, reperfusion injuries, ischaemic conditions, stroke, renal failure, cardiovascular diseases, vascular diseases other than cardiovascular diseases, diabetes mellitus, neurodegenerative diseases, retroviral infections, retinal damage, skin senescence and UV-induced skin damage, and as chemo- or radiosensitizers for cancer treatment.

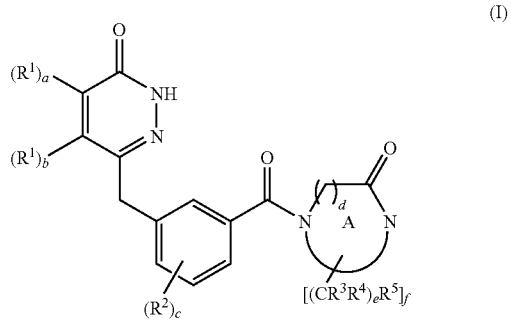

12 Claims, No Drawings

PYRIDAZINONE DERIVATIVES AS PARP INHIBITORS

PRIORITY CLAIM

This application is a §371 National Stage Application of PCT/GB2008/051063, filed on Nov. 14, 2008 which claims priority from GB Provisional Application Serial Numbers 0722401.7, filed on Nov. 15, 2007 and 0816707.4, filed on Sep. 12, 2008.

The present invention relates to pyridazinone derivatives which are inhibitors of the enzyme poly(ADP-ribose)polymerase (PARP), previously known as poly(ADP-ribose)synthase and poly(ADP-ribosyl)transferase. Compounds of the present invention are useful as mono-therapies in tumors with specific defects in DNA-repair pathways and as enhancers of certain DNA-damaging agents such as anticancer agents and radiotherapy. Furthermore, compounds of the present invention are useful for reducing cell necrosis (in stroke and myocardial infarction), down regulating inflammation and tissue injury, treating retroviral infections and protecting against the toxicity of chemotherapy.

Poly(ADP-ribose) polymerase (PARP) constitute a super family of eighteen proteins containing PARP catalytic domains (*Bioessays* (2004) 26:1148). These proteins include PARP-1, PARP-2, PARP-3, tankyrase-1, tankyrase-2, vault-PARP and TiPARP. PARP-1, the founding member, consists of three main domains: an amino (N)-terminal DNA-binding domain (DBD) containing two zinc fingers, the automodification domain, and a carboxy (C)-terminal catalytic domain.

PARP are nuclear and cytoplasmic enzymes that cleave NAD$^+$ to nicotinamide and ADP-ribose to form long and branched ADP-ribose polymers on target proteins, including topoisomerases, histones and PARP itself (*Biochem. Biophys. Res. Commun.* (1998) 245:1-10).

Poly(ADP-ribosyl)ation has been implicated in several biological processes, including DNA repair, gene transcription, cell cycle progression, cell death, chromatin functions and genomic stability.

The vast majority of PARP inhibitors to date interact with the nicotinamide binding domain of the enzyme and behave as competitive inhibitors with respect to NAD$^+$ (*Expert Opin. Ther. Patents* (2004) 14:1531-1551). Structural analogues of nicotinamide, such as benzamide and derivatives were among the first compounds to be investigated as PARP inhibitors. However, these molecules have a weak inhibitory activity and possess other effects unrelated to PARP inhibition. Thus, there is a need to provide potent inhibitors of the PARP enzyme.

US 2005/0234236 describes a process for the synthesis of pyridazinones, WO2004/085406 describes benzyl-pyridazinones as reverse transcriptase inhibitors and EP0810218 describes benzyl-pyridazinones as COX I and COX II inhibitors.

Compounds of this invention are useful in the inhibition of poly(ADP-ribose)polymerase (PARP). They are particularly useful as inhibitors of PARP-1 and/or PARP-2.

International Patent Application PCT/GB07/050,295 describes pyridinone and pyridazinone derivatives as PARP inhibitors. It has now been found that the presence of a carbonyl substituent on a saturated heterocyclic ring at the $R^5$ position of such compounds improves the inhibition of the PARP enzyme. Thus, the present invention provides compounds of formula I:

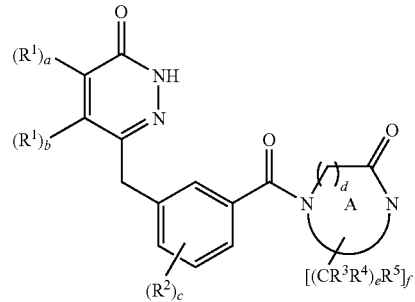

wherein:
 a is 0 or 1;
 b is 0 or 1;
 c is 0, 1, 2, 3 or 4;
 d is 1 or 2;
 e is 0, 1, 2, 3 or 4;
 f is 0, 1, 2, 3 or 4;
 A is a 6 to 15 membered monocyclic, fused, bridged or spiro saturated heterocyclic ring containing two N atoms and zero or one O atom, substituted by one oxo group;
 each $R^1$ is independently $C_{1-6}$alkyl, halo$C_{1-6}$alkyl, halogen or cyano;
 each $R^2$ is independently hydroxy, halogen, cyano, $C_{1-6}$alkyl, halo$C_{1-6}$alkyl, $C_{1-6}$alkoxy, halo$C_{1-6}$alkoxy or $NR^aR^b$;
 each of $R^3$ and $R^4$ is independently hydrogen, halogen, $C_{1-6}$alkyl or halo$C_{1-6}$alkyl;
 each $R^5$ is independently cyano, halogen, hydroxy, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;
 each $R^6$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, —O(C═O)$C_{1-6}$alkyl, —(C═O)O$C_{1-6}$alkyl, $NR^aR^b$, CONR$^a$R$^b$, NR$^a$COR$^b$, S(O)$_r$NR$^a$R$^b$, S(O)$_r$R$^c$, NR$^a$S(O)$_r$R$^c$ or a ring which is: $C_{3-10}$cycloalkyl, $C_{6-10}$aryl, $C_{6-10}$aryl$C_{1-6}$alkyl, $C_{6-10}$arylcarbonyl, $C_{6-10}$aryloxycarbonyl, $C_{6-10}$aryl$C_{1-6}$alkoxycarbonyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from halogen, $C_{1-6}$alkyl or halo$C_{1-6}$alkyl;
 r is 0, 1 or 2;
 each of $R^a$ and $R^b$ is independently hydrogen, $C_{1-6}$alkyl or a ring which is: $C_{3-10}$cycloalkyl, $C_{6-10}$aryl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 N atoms; any of which rings being optionally substituted by one, two or three groups independently selected from halogen, $C_{1-6}$alkyl or halo$C_{1-6}$alkyl;

$R^c$ is hydrogen or $C_{1-6}$alkyl;

or a pharmaceutically acceptable salt, stereoisomer or tautomer thereof.

In an embodiment of the previous embodiment, $R^5$ is not hydroxy.

In an embodiment of the previous embodiment:

f is 1, 2, 3 or 4;

A is a 6 to 15 membered monocyclic, fused, bridged or spiro saturated heterocyclic ring containing two N atoms and substituted by one oxo group; and each $R^6$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, —O(C=O)$C_{1-6}$alkyl, —(C=O)O$C_{1-6}$alkyl, $NR^aR^b$, $CONR^aR^b$, $NR^aCOR^b$, $S(O)_rNR^aR^b$, $NR^aS(O)_r$ or a ring which is: $C_{3-10}$cycloalkyl, $C_{6-10}$aryl, $C_{6-10}$aryl$C_{1-6}$alkyl, $C_{6-10}$arylcarbonyl, $C_{6-10}$aryloxycarbonyl, $C_{6-10}$aryl$C_{1-6}$alkoxycarbonyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from halogen, $C_{1-6}$alkyl or halo$C_{1-6}$alkyl.

In an embodiment the sum of a and b is 1 or 2.

In an embodiment a is 1 and b is 0 or 1.

In another embodiment a is 0 or 1 and b is 1.

In another embodiment each of a and b is 1.

In an embodiment c is 1 or 2.

In another embodiment c is 1.

In an embodiment d is 1.

In an embodiment e is 0, 1 or 2.

In an embodiment f is 0, 1, 2 or 3.

In another embodiment f is 1, 2 or 3.

In another embodiment f is 1 or 2.

In an embodiment f is 1.

In an embodiment r is 2.

In an embodiment A is a 6, 7, 8, 9 or 10 membered monocyclic, fused, bridged or spiro saturated heterocyclic ring containing two N atoms and zero or one O atom, substituted by one oxo group.

In an embodiment A is a 6, 7, 8, 9 or 10 membered monocyclic, fused, bridged or spiro saturated heterocyclic ring containing two N atoms and substituted by one oxo group.

Particular A groups are 3-oxopiperazin-1-yl, 4-oxooctahydro-2H-pyrido[1,2-a]pyrazin-2-yl, 3-oxo-2,5-diazabicyclo[2.2.1]heptan-5-yl, 3-oxo-1,4-diazepan-1-yl, 5-oxo-1,4-diazepan-1-yl, 6-oxohexahydropyrazino[2,1-c][1,4]oxazin-8(1H)-yl and 4-oxooctahydro-4H-pyrido[1,2-a]pyrazin-2-yl. Specific A groups are 3-oxopiperazin-1-yl, 4-oxooctahydro-2H-pyrido[1,2-a]pyrazin-2-yl, (1S,4S)-3-oxo-2,5-diazabicyclo[2.2.1]heptan-5-yl, 3-oxo-1,4-diazepan-1-yl and 5-oxo-1,4-diazepan-1-yl.

Further specific A groups are 6-oxohexahydropyrazino[2,1-c][1,4]oxazin-8(1H)-yl, (9aS)-4-oxooctahydro-4H-pyrido[1,2-a]pyrazin-2-yl and (9aR)-4-oxooctahydro-4H-pyrido[1,2-a]pyrazin-2-yl.

In an embodiment $R^1$ is $C_{1-6}$alkyl or halo$C_{1-6}$alkyl.

Particular $R^1$ groups are methyl, ethyl and trifluoromethyl. A further particular $R^1$ group is pentafluoroethyl.

In an embodiment $R^2$ is halogen, particularly fluorine and bromine. In an embodiment $R^2$ is fluorine.

In an embodiment $R^3$ is hydrogen, or $C_{1-6}$alkyl and each $R^4$ is independently selected from hydrogen, $C_{1-6}$alkyl or halo$C_{1-6}$alkyl.

In an embodiment $R^3$ is hydrogen and each $R^4$ is independently selected from hydrogen, $C_{1-6}$alkyl or halo$C_{1-6}$alkyl.

In an embodiment each $R^3$ is independently hydrogen or methyl and each $R^4$ is independently selected from hydrogen, methyl, ethyl or difluoromethyl.

In an embodiment $R^3$ is hydrogen and each $R^4$ is independently selected from hydrogen, methyl and difluoromethyl. A specific $R^3$ group is hydrogen and specific $R^4$ groups are hydrogen, methyl, difluoromethyl, (R)-methyl and (S)-methyl. A further specific $R^3$ group is methyl and a further specific $R^4$ group is ethyl.

In an embodiment each of $R^3$ and $R^4$ is hydrogen.

In an embodiment $R^5$ is halogen, $C_{1-6}$alkyl, $C_{1-6}$alkoxy, $C_{2-10}$alkenyl, halo$C_{1-6}$alkyl, halo$C_{1-6}$alkoxy or a ring which is: oxetanyl, azetidinyl, $C_{3-10}$cycloalkyl or a 5 or 6 membered saturated or partially saturated heterocyclic ring containing 1, 2 or 3 atoms independently selected from N, O and S; any of which rings being optionally substituted by one, two or three groups independently selected from $R^6$. A further $R^5$ group is hydroxy.

In another embodiment $R^5$ is $C_{6-10}$aryl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 N atoms; optionally substituted by one, two or three groups independently selected from $R^6$.

In an embodiment $R^5$ is cyclopentyl, cyclohexyl or phenyl, optionally substituted by one, two or three groups independently selected from fluorine, chlorine or cyano.

In an embodiment $R^5$ is halogen, $C_{1-4}$alkyl, halo$C_{1-4}$alkyl, $C_{1-4}$alkoxycarbonyl or a ring which is: phenyl, cyclohexyl, cyclopentyl, pyridinyl, naphthyl, thienyl, tetrahydropyranyl, bicyclo[1.1.1]pentyl, tetrahydronaphthalenyl, oxadiazolyl, cyclobutyl, quinolinyl, benzothienyl, thiazolyl, pyrimidinyl, tetrahydrofuranyl, dihydroindenyl or cycloheptyl; any of which rings being optionally substituted by one, two or three groups independently selected from $R^6$. Further $R^5$ rings are cyclopropyl, dihydrochromenyl, bicyclo[2.2.1]heptyl, oxaspiro[4.4]nonyl, oxaspiro[4.5]decyl, piperidinyl and imidazolyl, optionally substituted by one, two or three groups independently selected from $R^6$. Further $R^5$ groups are hydroxy and $C_{1-6}$alkoxy.

In an embodiment when $R^5$ is a ring it is unsubstituted, monosubstituted or disubstituted.

In an embodiment $R^6$ is cyano, halogen, $C_{1-6}$alkoxy, halo$C_{1-6}$alkyl, $C_{1-6}$alkylsulfonyl or $C_{6-10}$aryl. A further $R^6$ group is $C_{1-6}$alkyl.

In an embodiment:

$R^5$ is $C_{3-10}$cycloalkyl or $C_{6-10}$aryl, optionally substituted by one, two or three groups independently selected from $R^6$; and $R^6$ is fluorine, chlorine or cyano.

In an embodiment $R^6$ is halogen, $C_{1-6}$alkyl, $C_{1-6}$alkoxy, halo$C_{1-6}$alkyl or $C_{6-10}$aryl.

Particular $R^6$ groups include fluorine, chlorine, trifluoromethyl, methyl, methoxy, isopropyl and phenyl. Further particular $R^6$ groups are cyano and methylsulfonyl.

Thus, particular $R^5$ groups are phenyl, cyclohexyl, cyclopentyl, methyl, fluorophenyl, chlorophenyl, chlorofluorophenyl, difluorophenyl, (trifluoromethyl)phenyl, ethyl, butyl, dimethylphenyl, methoxyphenyl, methoxycarbonyl, pyridinyl, dichlorophenyl, naphthyl, thienyl, trifluoromethyl, tetrahydropyranyl, difluorocyclohexyl, difluorocyclopentyl, dimethylcyclohexyl, bicyclo[1.1.1]pentyl, tetrahydronaphthalenyl, isopropyloxadiazolyl, difluorocyclobutyl, phenyltetrahydropyranyl, cyclobutyl, fluoro, quinolinyl, (trifluoromethyl)pyridinyl, benzothienyl, thiazolyl, pyrimidinyl, phenylcyclohexyl, tetrahydrofuranyl, dihydroindenyl, cycloheptyl and isopropyl. Further particular $R^5$ groups are dimethyltetrahydropyranyl, fluorocyclopentyl, cyclopropyl, cyanophenyl, (methylsulfonyl)phenyl, methyltetrahydrofuranyl, dihydrochromenyl, bicyclo[2.2.1]heptyl, oxaspiro[4.4]nonyl, oxaspiro[4.5]decyl, methylcyclohexyl, (methylsulfonyl)piperidinyl, methylimidazolyl, dimethylthiazolyl and phenylcyclopentyl. Further particular $R^5$ groups are methoxy, ethoxy, isopropoxy, hydroxy and cyano fluorophenyl.

Specific $R^5$ groups are phenyl, cyclohexyl, cyclopentyl, methyl, 4-fluorophenyl, 3-chlorophenyl, 3-chloro-4-fluorophenyl, 3,4-difluorophenyl, 3,5-difluorophenyl, 4-chlorophenyl, 2-chlorophenyl, 2-(trifluoromethyl)phenyl, 2-chloro-4-fluorophenyl, ethyl, butyl, 3,5-dimethylphenyl, 4-methoxyphenyl, 3-methoxyphenyl, methoxycarbonyl, pyridin-2-yl, pyridin-3-yl, 3,5-dichlorophenyl, 1-naphthyl, 2-thienyl, trifluoromethyl, tetrahydro-2H-pyran-3-yl, 4,4-difluorocyclohexyl, 3,3-difluorocyclopentyl, 4,4-dimethylcyclohexyl, 3,3-dimethylcyclohexyl, bicyclo[1.1.1]pent-1-yl, 1,2,3,4-tetrahydronaphthalen-1-yl, 3-isopropyl-1,2,4-oxadiazol-5-yl, 3,3-difluorocyclobutyl, 4-phenyltetrahydro-2H-pyran-4-yl, cyclobutyl, fluoro, 3-fluorophenyl, quinolin-3-yl, 4-(trifluoromethyl)pyridin-2-yl, 1-benzothien-3-yl, 1,3-thiazol-5-yl, pyrimidin-5-yl, 5-(trifluoromethyl)pyridin-3-yl, 3-phenylcyclohexyl, (1S,2R)-2-phenylcyclohexyl, 4-phenylcyclohexyl, tetrahydrofuran-3-yl, 1,2,3,4-tetrahydronaphthalen-2-yl, 2,3-dihydro-1H-inden-2-yl, cycloheptyl, 3-thienyl and isopropyl. Further specific $R^5$ groups are (3R)-tetrahydrofuran-3-yl, (3S)-tetrahydrofuran-3-yl, 2,2-dimethyltetrahydro-2H-pyran-4-yl, S-methyl, R-methyl, cis-3-fluorocyclopentyl, cyclopropyl, 4-cyanophenyl, 4-(methylsulfonyl)phenyl, 2-methyltetrahydrofuran-2-yl, 3,4-dihydro-2H-chromen-3-yl, 2,3-dihydro-1H-inden-1-yl, (1R,2R,4S)-bicyclo[2.2.1]hept-2-yl, (3R)-tetrahydropyran-3-yl, (3S)-tetrahydropyran-3-yl, 1-oxaspiro[4.4]non-3-yl, 1-oxaspiro[4.5]dec-3-yl, 1-methylcyclohexyl, 1-(methylsulfonyl)piperidin-4-yl, 1-methyl-1H-imidazol-5-yl, 2,4-dimethyl-1,3-thiazol-5-yl, 3-phenylcyclopentyl, tetrahydro-2H-pyran-4-yl and (1R,4S)-bicyclo[2.2.1]hept-2-yl. Further specific $R^5$ groups are methoxy, (S)-methyl, (R)-methyl, (S)-ethyl, (R)-ethyl, ethoxy, isopropoxy, hydroxy, 4-cyano-3-fluorophenyl, 4-chloro-3-fluorophenyl, 4-chloro-2-fluorophenyl, 3-cyano-4-fluorophenyl, 5-chloro-3-fluorophenyl, 4-cyano-2-fluorophenyl, 5-cyano-3-fluorophenyl, 5-chloro-2-fluorophenyl, 3-chloro-2-fluorophenyl and (trans)-3-fluorocyclopentyl.

In an embodiment each of $R^a$ and $R^b$ is independently hydrogen or $C_{1-6}$alkyl. In an embodiment $R^c$ is $C_{1-6}$alkyl, for example methyl.

The present invention also provides compounds of formula II:

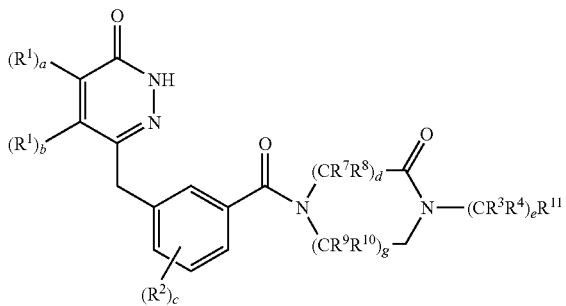

(II)

wherein:
a, b, c, d, e, $R^1$, $R^2$, $R^3$ and $R^4$ are as defined above;
g is 2 or 3;
each of $R^7$, $R^8$, $R^9$ and $R^{10}$ is independently hydrogen, halogen, $C_{1-6}$alkyl or halo$C_{1-6}$alkyl;
$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cyclo alkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;
$R^6$ is as defined above;
or one $R^7$ together with one $R^9$ forms a bridge containing 1, 2, or 3 carbon atoms optionally substituted by one, two or three groups independently selected from halogen or $C_{1-6}$alkyl;
or one $R^9$ and one $R^{10}$ together with the carbon atom to which they are attached form a spiro ring containing 3, 4, 5 or 6 carbon atoms optionally substituted by one, two or three groups independently selected from halogen, $C_{1-6}$alkyl or halo$C_{1-6}$alkyl;
or $R^{11}$ ($CR^3R^4$), together with N—($CR^9R^{10}$) forms a 4 to 8 membered fused saturated heterocyclic ring containing one N atom, optionally substituted by one, two or three groups independently selected from halogen, $C_{1-6}$alkyl or halo$C_{1-6}$alkyl;
or a pharmaceutically acceptable salt, stereoisomer or tautomer thereof.

In an embodiment of compounds of formula II:
each of $R^7$, $R^8$, $R^9$ and $R^{10}$ is independently hydrogen, halogen, $C_{1-6}$alkyl or halo$C_{1-6}$alkyl; and
$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cyclo alkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$.

In an embodiment:
each of $R^7$, $R^8$, $R^9$ and $R^{10}$ is independently hydrogen, halogen, $C_{1-6}$alkyl or halo$C_{1-6}$alkyl; or one $R^7$ together with one $R^9$ forms a bridge containing 1, 2, or 3 carbon atoms optionally substituted by one, two or three groups independently selected from halogen or $C_{1-6}$alkyl; and
$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cyclo alkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$.

In an embodiment:

each of $R^7$ and $R^8$ is independently hydrogen, halogen, $C_{1-6}$alkyl or halo$C_{1-6}$alkyl;

$R^{11}$ $(CR^3R^4)_e$ together with N—$(CR^9R^{10}$ forms a 4 to 8 membered fused saturated heterocyclic ring containing one N atom, optionally substituted by one, two or three groups independently selected from halogen, $C_{1-6}$alkyl or halo$C_{1-6}$alkyl;

each of the other $R^9$ and $R^{10}$ groups is independently hydrogen, halogen, $C_{1-6}$alkyl or halo$C_{1-6}$alkyl.

In an embodiment:

each of $R^7$, $R^8$, $R^9$ and $R^{10}$ is independently hydrogen, halogen, $C_{1-6}$alkyl or halo$C_{1-6}$alkyl;

or one $R^9$ and one $R^{10}$ together with the carbon atom to which they are attached form a spiro ring containing 3, 4, 5 or 6 carbon atoms optionally substituted by one, two or three groups independently selected from halogen, $C_{1-6}$alkyl or halo$C_{1-6}$alkyl;

$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cyclo alkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$.

The preferred identities with reference to compounds of formula II are as defined for formula I mutatis mutandis.

The preferred identities for $R^{11}$ are the same as provided for $R^5$ above. Thus, these include the particular and specific groups provided for $R^5$ above.

In an embodiment $R^{11}$ is halogen, $C_{1-4}$alkyl, halo$C_{1-4}$alkyl, $C_{1-6}$alkoxy, $C_{1-4}$alkoxycarbonyl or a ring which is: phenyl, cyclohexyl, cyclopentyl, pyridinyl, naphthyl, thienyl, tetrahydropyranyl, bicyclo[1.1.1]pentyl, tetrahydronaphthalenyl, oxadiazolyl, cyclobutyl, quinolinyl, benzothienyl, thiazolyl, pyrimidinyl, tetrahydrofuranyl, dihydroindenyl, cycloheptyl, cyclopropyl, dihydrochromenyl, bicyclo[2.2.1]heptyl, oxaspiro[4.4]nonyl, oxaspiro[4.5]decyl, piperidinyl or imidazolyl; any of which rings being optionally substituted by one, two or three groups independently selected from $R^6$.

In an embodiment each of $R^7$, $R^8$, $R^9$ and $R^{10}$ is hydrogen.

In an embodiment g is 2.

In an embodiment the sum of d and g is 3 or 4.

The present invention also provides compounds of formula III:

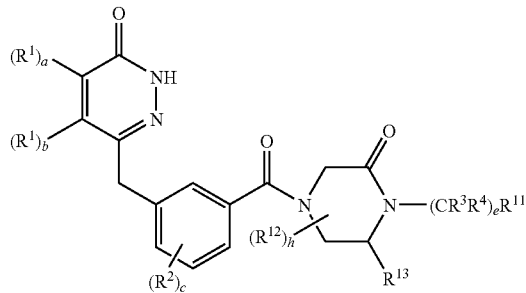

(III)

wherein:

a, b, c, $R^1$ and $R^2$ are as defined above;

h is 0, 1 or 2;

$R^{12}$ is $C_{1-6}$alkyl or halo$C_{1-6}$alkyl;

either:

$R^{13}$ is hydrogen or $R^{12}$;

e is 0, 1, 2, 3 or 4;

each $R^3$ and $R^4$ is independently hydrogen, halogen, $C_{1-6}$alkyl or halo$C_{1-6}$alkyl; and each $R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;

or:

$R^{11}$ $(CR^3R^4)_e$ and $R^{13}$ together with the N and C atoms to which they are attached form a fused 5, 6 or 7 membered saturated heterocyclic ring containing one N atom, optionally substituted by one, two or three groups independently selected from halogen, $C_{1-6}$alkyl or halo$C_{1-6}$alkyl;

or a pharmaceutically acceptable salt, stereoisomer or tautomer thereof.

The present invention also provides compounds of formula IV:

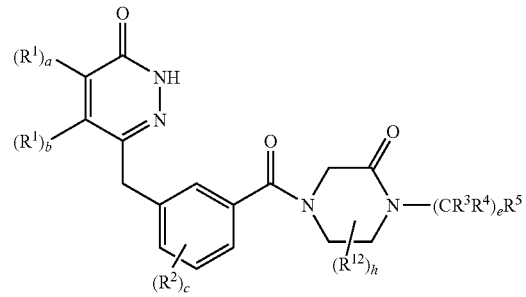

(IV)

wherein:

a, b, c, h, e, $R^1$, $R^2$, $R^3$, $R^4$, $R^5$ and $R^{12}$ are as defined above;

or a pharmaceutically acceptable salt, stereoisomer or tautomer thereof.

The present invention also provides compounds of formula V:

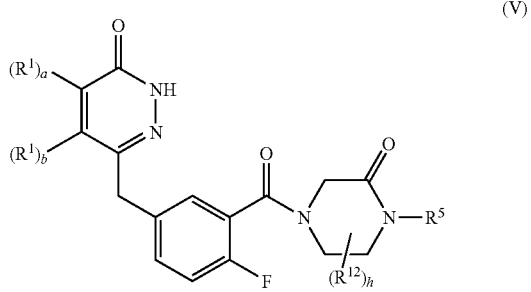

(V)

wherein:
a, b, and $R^1$ are as defined above;
h is 0 or 1;
$R^5$ is $C_{3-10}$cycloalkyl or $C_{6-10}$aryl, optionally substituted by one, two or three groups independently selected from fluorine, chlorine or cyano;
$R^{12}$ methyl;
or a pharmaceutically acceptable salt, stereoisomer or tautomer thereof.

In an embodiment $R^5$ is cyclopentyl, cyclohexyl or phenyl, optionally substituted by one, two or three groups independently selected from fluorine, chlorine or cyano.

The preferred identities with reference to compounds of formulae III, IV and V are as defined above for formulae I and II mutatis mutandis.

In an embodiment h is 0.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

The compounds disclosed herein may exist as tautomers and both tautomeric forms are intended to be encompassed by the scope of the invention, even though only one tautomeric structure may be depicted. For example, compounds of formula I may tautomerise into compounds of the following structure I:

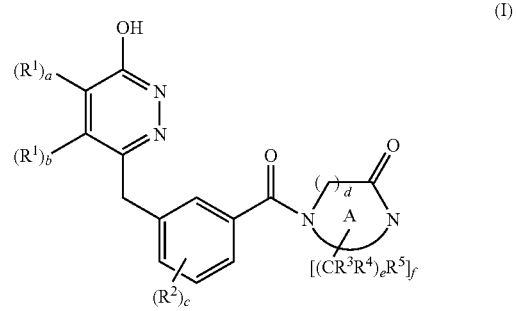

(I)

The compounds may exist in different isomeric forms, all of which are encompassed by the present invention.

The compounds may exist in a number of different polymorphic forms.

When any variable (e.g. $R^1$ etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain, saturated aliphatic hydrocarbon groups having the specified number of carbon atoms. For example, "$C_{1-6}$alkyl" is defined to include groups having 1, 2, 3, 4, 5 or 6 carbons in a linear or branched arrangement. For example, "$C_{1-6}$alkyl" specifically includes methyl, ethyl, n-propyl, i-propyl, n-butyl, t-butyl, i-butyl, pentyl and hexyl and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-10}$alkenyl" refers to a non-aromatic hydrocarbon radical, straight or branched, containing from 2 to 10, including 2 to 6, carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-10}$alkynyl" refers to a hydrocarbon radical straight or branched, containing from containing from 2 to 10, including 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy, t-butoxy, cyclopropyloxy, cyclobutyloxy and cyclopentyloxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$. The term 'hydroxy$C_{2-10}$alkenyl' and 'hydroxy$C_{2-10}$alkynyl' can be construed analogously. An example of 'hydroxy$C_{2-10}$alkynyl' is (hydroxy)(methyl)butynyl.

As used herein, the term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

The rings present in the compounds of this invention may be monocyclic or multicyclic, particularly bicyclic. The multicyclic rings may be fused, bridged or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

6-15 membered heterocycles include 6, 7, 8, 9, 10, 11, 12, 13, 14 and 15 membered heterocycles. Similarly, 7-10 membered rings include 7, 8, 9 and 10 membered rings.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, diazepanyl, azoniabicyclohexanyl, azoniabicycloheptanyl, azepanyl, octahydropyridopyrazinyl, diazabicycloheptanyl diazoniaspirodecanyl, diazoniaspirononanyl, octahydropyrrolopyrrolyl and tetrahydrotriazolopyrazinyl and N-oxides thereof. Attachment of a heterocyclyl substituent can occur via a carbon atom or via a heteroatom.

Preferred 5 or 6 membered saturated or partially saturated heterocycles are pyrrolidinyl, piperidinyl, piperazinyl, morpholinyl, tetrahydrofuran, thiomorpholinyl, azoniabicyclohexanyl, azoniabicycloheptanyl and tetrahydropyranyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteroaromatic rings are pyridinyl, pyrimidinyl, pyridazinyl and pyrazinyl.

Preferred 7-10 membered saturated, partially saturated or unsaturated heterocyclic rings are diazepanyl, azepanyl, tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, octahydropyridopyrazinyl, diazabicycloheptanyl, diazoniaspirodecanyl, diazoniaspirononanyl, octahydropyrrolopyrrolyl and tetrahydrotriazolopyrazinyl.

As used herein, the term "halogen" refers to fluorine, chlorine, bromine and iodine, of which fluorine and chlorine are preferred.

Particular compounds within the scope of the present invention are:

6-{4-Fluoro-3-[(3-oxo-4-phenylpiperazin-1-yl)carbonyl]benzyl}-4,5-dimethyl-3-oxo-2,3-dihydropyridazin-1-ium trifluoroacetate;
6-{3-[(4-Cyclohexyl-3-oxopiperazin-1-yl)carbonyl]-4-fluorobenzyl}-4,5-dimethyl-3-oxo-2,3-dihydropyridazin-1-ium trifluoroacetate;
6-{3-[(4-Cyclopentyl-3-oxopiperazin-1-yl)carbonyl]-4-fluorobenzyl}-4,5-dimethylpyridazin-3(2H)-one;
6-{4-Fluoro-3-[(3-oxo-4-phenylpiperazin-1-yl)carbonyl]benzyl}-4,5-dimethylpyridazin-3(2H)-one hydrochloride;
4-Ethyl-6-{4-fluoro-3-[(3-oxo-4-phenylpiperazin-1-yl)carbonyl]benzyl}pyridazin-3(2H)-one trifluoroacetate;
6-{3-[(4-Cyclohexyl-3-oxopiperazin-1-yl)carbonyl]-4-fluorobenzyl}-4-ethylpyridazin-3(2H)-one trifluoroacetate;
3-{4-Fluoro-3-[(4-methyl-3-oxopiperazin-1-yl)carbonyl]benzyl}-4,5-dimethyl-6-oxo-1,6-dihydropyridazin-1-ium trifluoroacetate;
3-(4-Fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate;
6-(3-{[4-(2-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,4-Difluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,5-Difluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(4-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(2-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-[4-Fluoro-3-({3-oxo-4-[2-(trifluoromethyl)phenyl]piperazin-1-yl}carbonyl)benzyl]-4,5-dimethyl-3-oxo-2,3-dihydropyridazin-1-ium trifluoroacetate;
6-(3-{[4-(2-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate;
6-{3-[(4-Ethyl-3-oxopiperazin-1-yl)carbonyl]-4-fluorobenzyl}-4,5-dimethylpyridazin-3(2H)-one trifluoroacetate;
6-{3-[(4-Butyl-3-oxopiperazin-1-yl)carbonyl]-4-fluorobenzyl}-4,5-dimethylpyridazin-3(2H)-one trifluoroacetate;
6-(3-{[4-(3,5-Dimethylbenzyl)-3-oxopiperazin-1-yl]carbonyl}-4-fluorobenzyl)-4,5-dimethylpyridazin-3(2H)-one trifluoroacetate;
6-(4-Fluoro-3-{[4-(4-methoxybenzyl)-3-oxopiperazin-1-yl]carbonyl}benzyl)-4,5-dimethylpyridazin-3(2H)-one trifluoroacetate;
6-(4-Fluoro-3-{[3-oxo-4-(2-phenylethyl)piperazin-1-yl]carbonyl}benzyl)-4,5-dimethylpyridazin-3(2H)-one trifluoroacetate;
6-(4-Fluoro-3-{[4-(3-methoxyphenyl)-3-oxopiperazin-1-yl]carbonyl}benzyl)-4,5-dimethylpyridazin-3(2H)-one trifluoroacetate;
6-(3-{[4-(3,5-Dimethylphenyl)-3-oxopiperazin-1-yl]carbonyl}-4-fluorobenzyl)-4,5-dimethylpyridazin-3(2H)-one trifluoroacetate;
Methyl (4-{5-[(4,5-dimethyl-6-oxo-1,6-dihydropyridazin-3-yl)methyl]-2-fluorobenzoyl}-2-oxopiperazin-1-yl)acetate trifluoroacetate;
3-{3-[(4-Cyclohexyl-3-oxopiperazin-1-yl)carbonyl]-4-fluorobenzyl}-4-methyl-6-oxo-5-(trifluoromethyl)-1,6-dihydropyridazin-1-ium trifluoroacetate;
3-(3-{[4-(3,4-Difluorophenyl)-3-oxopiperazin-1-yl]carbonyl}-4-fluorobenzyl)-4-methyl-6-oxo-5-(trifluoromethyl)-1,6-dihydropyridazin-1-ium trifluoroacetate;
6-{3-[(4-Cyclohexyl-3-oxopiperazin-1-yl)carbonyl]-4-fluorobenzyl}-3-oxo-4-(trifluoromethyl)-2,3-dihydropyridazin-1-ium trifluoroacetate;
3-{3-[(4-Cyclohexyl-3-oxopiperazin-1-yl)carbonyl]-4-fluorobenzyl}-4-ethyl-5-methyl-6-oxo-1,6-dihydropyridazin-1-ium trifluoroacetate;
3-{3-[(4-Cyclohexyl-3-oxopiperazin-1-yl)carbonyl]-4-fluorobenzyl}-5-ethyl-4-methyl-6-oxo-1,6-dihydropyridazin-1-ium trifluoroacetate;
3-{3-[(4-Cyclopentyl-3-oxopiperazin-1-yl)carbonyl]-4-fluorobenzyl}-5-ethyl-6-oxo-1,6-dihydropyridazin-1-ium trifluoroacetate;
3-{4-Fluoro-3-[(3-oxo-4-pyridin-2-ylpiperazin-1-yl)carbonyl]benzyl}-4,5-dimethyl-6-oxo-1,6-dihydropyridazin-1-ium trifluoroacetate;
6-{4-Fluoro-3-[(4-oxooctahydro-2H-pyrido[1,2-a]pyrazin-2-yl)carbonyl]benzyl}-4,5-dimethyl-3-oxo-2,3-dihydropyridazin-1-ium trifluoroacetate;
6-{3-[(4-Cyclopentyl-3-oxopiperazin-1-yl)carbonyl]-4-fluorobenzyl}-3-oxo-4-(trifluoromethyl)-2,3-dihydropyridazin-1-ium trifluoroacetate;
6-{3-[(4-Cyclohexyl-3-oxo-1,4-diazepan-1-yl)carbonyl]-4-fluorobenzyl}-4,5-dimethyl-3-oxo-2,3-dihydropyridazin-1-ium trifluoroacetate;
6-{3-[(4-Cyclohexyl-2-methyl-3-oxopiperazin-1-yl)carbonyl]-4-fluorobenzyl}-4,5-dimethyl-3-oxo-2,3-dihydropyridazin-1-ium trifluoroacetate;
6-{4-Fluoro-3-[(4-isopropyl-5-oxo-1,4-diazepan-1-yl)carbonyl]benzyl}-4,5-dimethyl-3-oxo-2,3-dihydropyridazin-1-ium trifluoroacetate;
3-{3-[(4-Cyclohexyl-2,2-dimethyl-3-oxopiperazin-1-yl)carbonyl]-4-fluorobenzyl}-4,5-dimethyl-6-oxo-1,6-dihydropyridazin-1-ium trifluoroacetate;
6-{4-Fluoro-3-[(3-oxo-4-pyridin-3-ylpiperazin-1-yl)carbonyl]benzyl}-4,5-dimethylpyridazin-3(2H)-one;
6-{3-[(4-Cyclohexyl-3-oxopiperazin-1-yl)carbonyl]-4-fluorobenzyl}-5-ethyl-4-(trifluoromethyl)pyridazin-3(2H)-one trifluoroacetate;
6-(4-Fluoro-3-{[4-(4-fluorophenyl)-3-oxopiperazin-1-yl]carbonyl}benzyl)-4,5-dimethyl-3-oxo-2,3-dihydropyridazin-1-ium trifluoroacetate;

(1S,4S)-5-{5-[(4,5-Dimethyl-6-oxo-1,6-dihydropyridazin-3-yl)methyl]-2-fluorobenzoyl}-2-phenyl-2,5-diazabicyclo[2.2.1]heptan-3-one trifluoroacetate;
3-(3-{[4-(3,5-Dichlorophenyl)-3-oxopiperazin-1-yl]carbonyl}-4-fluorobenzyl)-4,5-dimethyl-6-oxo-1,6-dihydropyridazin-1-ium trifluoroacetate;
3-(4-Fluoro-3-{[4-(1-naphthyl)-3-oxopiperazin-1-yl]carbonyl}benzyl)-4,5-dimethyl-6-oxo-1,6-dihydropyridazin-1-ium trifluoroacetate;
3-(4-Fluoro-3-{[3-oxo-4-(2-thienyl)piperazin-1-yl]carbonyl}benzyl)-4,5-dimethyl-6-oxo-1,6-dihydropyridazin-1-ium trifluoroacetate;
6-(4-Fluoro-3-{[3-oxo-4-(3,3,3-trifluoro-2-methylpropyl)piperazin-1-yl]carbonyl}benzyl)-4,5-dimethyl-3-oxo-2,3-dihydropyridazin-1-ium trifluoroacetate;
6-(3-{[4-(2,2-Difluoro-1-phenylethyl)-3-oxopiperazin-1-yl]carbonyl}-4-fluorobenzyl)-4,5-dimethyl-3-oxo-2,3-dihydropyridazin-1-ium trifluoroacetate;
6-(4-Fluoro-3-{[3-oxo-4-(tetrahydro-2H-pyran-3-yl)piperazin-1-yl]carbonyl}benzyl)-4,5-dimethyl-3-oxo-2,3-dihydropyridazin-1-ium trifluoroacetate;
6-(3-{[4-(4,4-Difluorocyclohexyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,3-Difluorocyclopentyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(4,4-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,3-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate;
6-{3-[(4-Bicyclo[1.1.1]pent-1-yl-3-oxopiperazin-1-yl)carbonyl]-4-fluorobenzyl}-4,5-dimethyl-3-oxo-2,3-dihydropyridazin-1-ium trifluoroacetate;
6-(4-Fluoro-3-{[3-oxo-4-(1,2,3,4-tetrahydronaphthalen-1-ylmethyl)piperazin-1-yl]carbonyl}benzyl)-4,5-dimethyl-3-oxo-2,3-dihydropyridazin-1-ium trifluoroacetate;
6-[4-Fluoro-3-({4-[1-(3-isopropyl-1,2,4-oxadiazol-5-yl)ethyl]-3-oxopiperazin-1-yl}carbonyl)benzyl]-4,5-dimethyl-3-oxo-2,3-dihydropyridazin-1-ium trifluoroacetate;
6-(3-{[4-(3,3-Difluorocyclobutyl)-3-oxopiperazin-1-yl]carbonyl}-4-fluorobenzyl)-4,5-dimethyl-3-oxo-2,3-dihydropyridazin-1-ium trifluoroacetate;
6-[4-Fluoro-3-({3-oxo-4-[(4-phenyltetrahydro-2H-pyran-4-yl)methyl]piperazin-1-yl}carbonyl)benzyl]-4,5-dimethyl-3-oxo-2,3-dihydropyridazin-1-ium trifluoroacetate;
6-{3-[(4-Cyclobutyl-3-oxopiperazin-1-yl)carbonyl]-4-fluorobenzyl}-4,5-dimethyl-3-oxo-2,3-dihydropyridazin-1-ium trifluoroacetate;
6-(4-Fluoro-3-{[4-(2-fluoroethyl)-3-oxopiperazin-1-yl]carbonyl}benzyl)-4,5-dimethyl-3-oxo-2,3-dihydropyridazin-1-ium trifluoroacetate;
6-[4-Fluoro-3-({4-[2-(3-fluorophenyl)ethyl]-3-oxopiperazin-1-yl}carbonyl)benzyl]-4,5-dimethyl-3-oxo-2,3-dihydropyridazin-1-ium trifluoroacetate;
6-{4-Fluoro-3-[(3-oxo-4-quinolin-3-ylpiperazin-1-yl)carbonyl]benzyl}-4,5-dimethylpyridazin-3(2H)-one;
3-[4-Fluoro-3-({3-oxo-4-[4-(trifluoromethyl)pyridin-2-yl]piperazin-1-yl}carbonyl)benzyl]-4,5-dimethyl-6-oxo-1,6-dihydropyridazin-1-ium trifluoroacetate;
3-(3-{[4-(1-Benzothien-3-yl)-3-oxopiperazin-1-yl]carbonyl}-4-fluorobenzyl)-4,5-dimethyl-6-oxo-1,6-dihydropyridazin-1-ium trifluoroacetate;
3-(4-Fluoro-3-{[3-oxo-4-(1,3-thiazol-5-yl)piperazin-1-yl]carbonyl}benzyl)-4,5-dimethyl-6-oxo-1,6-dihydropyridazin-1-ium trifluoroacetate;
3-{4-Fluoro-3-[(3-oxo-4-pyrimidin-5-ylpiperazin-1-yl)carbonyl]benzyl}-4,5-dimethyl-6-oxo-1,6-dihydropyridazin-1-ium trifluoroacetate;
3-[4-Fluoro-3-({3-oxo-4-[5-(trifluoromethyl)pyridin-3-yl]piperazin-1-yl}carbonyl)benzyl]-4,5-dimethyl-6-oxo-1,6-dihydropyridazin-1-ium trifluoroacetate;
6-(4-Fluoro-3-{[3-oxo-4-(3-phenylcyclohexyl)piperazin-1-yl]carbonyl}benzyl)-4,5-dimethyl-3-oxo-2,3-dihydropyridazin-1-ium trifluoroacetate;
6-[4-Fluoro-3-({3-oxo-4-[(1R,2S)-2-phenylcyclohexyl]piperazin-1-yl}carbonyl)benzyl]-4,5-dimethyl-3-oxo-2,3-dihydropyridazin-1-ium trifluoroacetate;
6-(4-Fluoro-3-{[3-oxo-4-(4-phenylcyclohexyl)piperazin-1-yl]carbonyl}benzyl)-4,5-dimethyl-3-oxo-2,3-dihydropyridazin-1-ium trifluoroacetate;
6-(4-Fluoro-3-{[3-oxo-4-(tetrahydrofuran-3-yl)piperazin-1-yl]carbonyl}benzyl)-4,5-dimethyl-3-oxo-2,3-dihydropyridazin-1-ium trifluoroacetate;
6-(4-Fluoro-3-{[3-oxo-4-(1,2,3,4-tetrahydronaphthalen-2-yl)piperazin-1-yl]carbonyl}benzyl)-4,5-dimethyl-3-oxo-2,3-dihydropyridazin-1-ium trifluoroacetate;
6-(3-{[4-(2,3-Dihydro-1H-inden-2-yl)-3-oxopiperazin-1-yl]carbonyl}-4-fluorobenzyl)-4,5-dimethyl-3-oxo-2,3-dihydropyridazin-1-ium trifluoroacetate;
6-(4-Fluoro-3-{[3-oxo-4-(2,2,2-trifluoroethyl)piperazin-1-yl]carbonyl}benzyl)-4,5-dimethyl-3-oxo-2,3-dihydropyridazin-1-ium trifluoroacetate;
6-{3-[(4-Cycloheptyl-3-oxopiperazin-1-yl)carbonyl]-4-fluorobenzyl}-4,5-dimethyl-3-oxo-2,3-dihydropyridazin-1-ium trifluoroacetate;
3-(4-Fluoro-3-{[4-(3-thienyl)piperazin-1-yl]carbonyl}benzyl)-4,5-dimethyl-6-oxo-1,6-dihydropyridazin-1-ium trifluoroacetate;

and pharmaceutically acceptable salts, stereoisomers, free bases and tautomers thereof.

Further particular compounds within the scope of the present invention are:
6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one;
6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one;
6-(3-{[4-(2,2-dimethyltetrahydro-2H-pyran-4-yl)-3-oxopiperazin-1-yl]carbonyl}-4-fluorobenzyl)-4,5-dimethylpyridazin-3(2H)-one trifluoroacetate;
6-{3-[(3,3-Dimethyl-5-oxo-4-phenylpiperazin-1-yl)carbonyl]-4-fluorobenzyl}-4,5-dimethylpyridazin-3(2H)-one;
3-[4-fluoro-3-(3-methyl-5-oxo-4-phenyl-piperazine-1-carbonyl)-benzyl]-4,5-dimethyl-6-oxo-1,6-dihydro-pyridazin-1-ium trifluoroacetate;
6-(4-fluoro-3-{[(3S)-3-methyl-5-oxo-4-phenylpiperazin-1-yl]carbonyl}benzyl)-4,5-dimethylpyridazin-3(2H)-one;
6-(4-fluoro-3-{[(3R)-3-methyl-5-oxo-4-phenylpiperazin-1-yl]carbonyl}benzyl)-4,5-dimethylpyridazin-3(2H)-one;
3-{4-fluoro-3-[4-(4-fluoro-phenyl)-3-methyl-5-oxo-piperazine-1-carbonyl]-benzyl}-4,5-dimethyl-6-oxo-1,6-dihydro-pyridazin-1-ium trifluoroacetate;
6-(4-fluoro-3-{[(3S)-4-(4-fluorophenyl)-3-methyl-5-oxopiperazin-1-yl]carbonyl}benzyl)-4,5-dimethylpyridazin-3(2H)-one;
6-(4-fluoro-3-{[(3R)-4-(4-fluorophenyl)-3-methyl-5-oxopiperazin-1-yl]carbonyl}benzyl)-4,5-dimethylpyridazin-3(2H)-one;

cis-3-{4-Fluoro-3-[4-(3-fluoro-cyclopentyl)-3-oxo-piperazine-1-carbonyl]-benzyl}-4,5-dimethyl-6-oxo-1,6-dihydro-pyridazin-1-ium trifluoroacetate;
6-{3-[(4-cyclopentyl-3-oxopiperazin-1-yl)carbonyl]-4-fluorobenzyl}-4-(pentafluoroethyl)pyridazin-3(2H)-one;
1-cyclopropyl-4-{5-[(4,5-dimethyl-6-oxo-1,6-dihydropyridazin-3-yl)methyl]-2-fluorobenzoyl}-1,4-diazepan-2-one;
6-{2-bromo-5-[(4-cyclopentyl-3-oxopiperazin-1-yl)carbonyl]-4-fluorobenzyl}-4,5-dimethylpyridazin-3(2H)-one;
6-{4-fluoro-3-[(6-oxohexahydropyrazino[2,1-c][1,4]oxazin-8(1H)-yl)carbonyl]benzyl}-4,5-dimethyl-3-oxo-2,3-dihydropyridazin-1-ium trifluoroacetate;
6-{4-fluoro-3-[(cis-6-methyl-4-oxooctahydro-2H-pyrido[1,2-a]pyrazin-2-yl)carbonyl]benzyl}-4,5-dimethyl-3-oxo-2,3-dihydropyridazin-1-ium trifluoroacetate;
(6S,9aS)-2-{5-[(4,5-dimethyl-6-oxo-1,6-dihydropyridazin-3-yl)methyl]-2-fluorobenzoyl}-6-methyloctahydro-4H-pyrido[1,2-a]pyrazin-4-one;
(6R,9aR)-2-{5-[(4,5-dimethyl-6-oxo-1,6-dihydropyridazin-3-yl)methyl]-2-fluorobenzoyl}-6-methyloctahydro-4H-pyrido[1,2-a]pyrazin-4-one;
6-{4-fluoro-3-[(cis-6-methyl-4-oxooctahydro-2H-pyrido[1,2-a]pyrazin-2-yl)carbonyl]benzyl}-3-oxo-4-(trifluoromethyl)-2,3-dihydropyridazin-1-ium trifluoroacetate;
(6S,9aS)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one;
(6R,9aR)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one;
(9aS)-2-{5-[(4,5-dimethyl-6-oxo-1,6-dihydropyridazin-3-yl)methyl]-2-fluorobenzoyl}octahydro-4H-pyrido[1,2-a]pyrazin-4-one trifluoroacetate;
(9aR)-2-{5-[(4,5-dimethyl-6-oxo-1,6-dihydropyridazin-3-yl)methyl]-2-fluorobenzoyl}octahydro-4H-pyrido[1,2-a]pyrazin-4-one trifluoroacetate;
2-(2-fluoro-5-{[6-oxo-5-(trifluoromethyl)-1,6-dihydropyridazin-3-yl]methyl}benzoyl)octahydro-4H-pyrido[1,2-a]pyrazin-4-one;
(9aS)-2-(2-fluoro-5-{[6-oxo-5-(trifluoromethyl)-1,6-dihydropyridazin-3-yl]methyl}benzoyl)octahydro-4H-pyrido[1,2-c]pyrazin-4-one;
(9aR)-2-(2-fluoro-5-{[6-oxo-5-(trifluoromethyl)-1,6-dihydropyridazin-3-yl]methyl}benzoyl)octahydro-4H-pyrido[1,2-c]pyrazin-4-one;
3-{3-[(4-cyclohexyl-2,2-dimethyl-5-oxopiperazin-1-yl)carbonyl]-4-fluorobenzyl}-4,5-dimethyl-6-oxo-1,6-dihydropyridazin-1-ium trifluoroacetate;
3-(3-{[4-(4-cyanophenyl)-3-oxopiperazin-1-yl]carbonyl}-4-fluorobenzyl)-4,5-dimethyl-6-oxo-1,6-dihydropyridazin-1-ium trifluoroacetate;
3-[4-fluoro-3-({4-[4-(methylsulfonyl)phenyl]-3-oxopiperazin-1-yl}carbonyl)benzyl]-4,5-dimethyl-6-oxo-1,6-dihydropyridazin-1-ium trifluoroacetate;
6-(3-{[4-(2,2-difluoro-1-pyridin-3-ylethyl)-3-oxopiperazin-1-yl]carbonyl}-4-fluorobenzyl)-4,5-dimethyl-3-oxo-2,3-dihydropyridazin-1-ium trifluoroacetate;
6-[4-fluoro-3-({4-[(2-methyltetrahydrofuran-2-yl)methyl]-3-oxopiperazin-1-yl}carbonyl)benzyl]-4,5-dimethyl-3-oxo-2,3-dihydropyridazin-1-ium trifluoroacetate;
6-(3-{[4-(3,4-dihydro-2H-chromen-3-yl)-3-oxopiperazin-1-yl]carbonyl}-4-fluorobenzyl)-4,5-dimethyl-3-oxo-2,3-dihydropyridazin-1-ium trifluoroacetate;
6-(4-fluoro-3-{[3-oxo-4-(1,2,3,4-tetrahydronaphthalen-1-yl)piperazin-1-yl]carbonyl}benzyl)-4,5-dimethyl-3-oxo-2,3-dihydropyridazin-1-ium trifluoroacetate;
6-(3-{[4-(2,3-dihydro-1H-inden-1-yl)-3-oxopiperazin-1-yl]carbonyl}-4-fluorobenzyl)-4,5-dimethyl-3-oxo-2,3-dihydropyridazin-1-ium trifluoroacetate;
6-[3-({4-[(1R,2R,4S)-bicyclo[2.2.1]hept-2-yl]-3-oxopiperazin-1-yl}carbonyl)-4-fluorobenzyl]-4,5-dimethyl-3-oxo-2,3-dihydropyridazin-1-ium trifluoroacetate;
6-{3-[(4-cyclopentyl-3-methyl-5-oxopiperazin-1-yl)carbonyl]-4-fluorobenzyl}-4,5-dimethyl-3-oxo-2,3-dihydropyridazin-1-ium trifluoroacetate;
6-[4-fluoro-3-({3-oxo-4-[(3S)-tetrahydro-2H-pyran-3-yl]piperazin-1-yl}carbonyl)benzyl]-4,5-dimethylpyridazin-3(2H)-one;
6-[4-fluoro-3-({3-oxo-4-[(3R)-tetrahydro-2H-pyran-3-yl]piperazin-1-yl}carbonyl)benzyl]-4,5-dimethylpyridazin-3(2H)-one;
3-{3-[(4-ethyl-3-oxopiperazin-1-yl)carbonyl]-4-fluorobenzyl}-4-methyl-6-oxo-5-(trifluoromethyl)-1,6-dihydropyridazin-1-ium trifluoroacetate;
6-(4-fluoro-3-{[4-(1-oxaspiro[4.4]non-3-yl)-3-oxopiperazin-1-yl]carbonyl}benzyl)-4,5-dimethylpyridazin-3(2H)-one trifluoroacetate;
6-(4-fluoro-3-{[4-(1-oxaspiro[4.5]dec-3-yl)-3-oxopiperazin-1-yl]carbonyl}benzyl)-4,5-dimethylpyridazin-3(2H)-one trifluoroacetate;
(9aR)-2-{5-[(4,5-dimethyl-6-oxo-1,6-dihydropyridazin-3-yl)methyl]-2-fluorobenzoyl}octahydro-4H-pyrido[1,2-a]pyrazin-4-one;
(9aS)-2-{5-[(4,5-dimethyl-6-oxo-1,6-Dihydropyridazin-3-yl)methyl]-2-fluorobenzoyl}octahydro-4H-pyrido[1,2-a]pyrazin-4-one;
6-(4-fluoro-3-{[4-(1-methylcyclohexyl)-3-oxopiperazin-1-yl]carbonyl}benzyl)-4,5-dimethyl-3-oxo-2,3-dihydropyridazin-1-ium trifluoroacetate;
6-[4-fluoro-3-({4-[1-(methylsulfonyl)piperidin-4-yl]-3-oxopiperazin-1-yl}carbonyl)benzyl]-4,5-dimethyl-3-oxo-2,3-dihydropyridazin-1-ium trifluoroacetate;
6-[4-fluoro-3-({3-oxo-4-[(3R)-tetrahydrofuran-3-yl]piperazin-1-yl}carbonyl)benzyl]-4,5-dimethylpyridazin-3(2H)-one;
6-[4-fluoro-3-({3-oxo-4-[(3S)-tetrahydrofuran-3-yl]piperazin-1-yl}carbonyl)benzyl]-4,5-dimethylpyridazin-3(2H)-one;
6-(3-{[(3S)-4-cyclopentyl-3-methyl-5-oxopiperazin-1-yl]carbonyl}-4-fluorobenzyl)-4,5-dimethylpyridazin-3(2H)-one;
6-(3-{[(3R)-4-cyclopentyl-3-methyl-5-oxopiperazin-1-yl]carbonyl}-4-fluorobenzyl)-4,5-dimethylpyridazin-3(2H)-one;
3-(4-fluoro-3-{[4-(1-methyl-1H-imidazol-5-yl)-3-oxopiperazin-1-yl]carbonyl}benzyl)-4,5-dimethyl-6-oxo-1,6-dihydropyridazin-1-ium trifluoroacetate;
3-(3-{[4-(2,4-dimethyl-1,3-thiazol-5-yl)-3-oxopiperazin-1-yl]carbonyl}-4-fluorobenzyl)-4,5-dimethyl-6-oxo-1,6-dihydropyridazin-1-ium trifluoroacetate;
6-[3-({4-[2,2-difluoro-1-(4-fluorophenyl)ethyl]-3-oxopiperazin-1-yl}carbonyl)-4-fluorobenzyl]-4,5-dimethyl-3-oxo-2,3-dihydropyridazin-1-ium trifluoroacetate;
6-(4-fluoro-3-{[3-oxo-4-(3-phenylcyclopentyl)piperazin-1-yl]carbonyl}benzyl)-4,5-dimethyl-3-oxo-2,3-dihydropyridazin-1-ium trifluoroacetate;
6-(4-fluoro-3-{[3-oxo-4-(tetrahydro-2H-pyran-4-yl)piperazin-1-yl]carbonyl}benzyl)-4,5-dimethyl-3-oxo-2,3-dihydropyridazin-1-ium trifluoroacetate;
6-[4-fluoro-3-({3-oxo-4-[(1R)-1-phenylethyl]piperazin-1-yl}carbonyl)benzyl]-4,5-dimethyl-3-oxo-2,3-dihydropyridazin-1-ium trifluoroacetate;

6-[4-fluoro-3-({3-oxo-4-[(1S)-1-phenylethyl]piperazin-1-yl}carbonyl)benzyl]-4,5-dimethyl-3-oxo-2,3-dihydropyridazin-1-ium trifluoroacetate;
6-(3-{[4-(2,2-difluoro-1R-phenylethyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(2,2-difluoro-1S-phenylethyl)-3-oxopiperazin-1-yl]carbonyl}-4-fluorobenzyl)-4,5-dimethyl-3-oxo-2,3-dihydropyridazin-1-ium trifluoroacetate;
3-{3-[(4-cyclohexyl-3-methyl-5-oxopiperazin-1-yl)carbonyl]-4-fluorobenzyl}-4,5-dimethyl-6-oxo-1,6-dihydropyridazin-1-ium trifluoroacetate;
6-(3-{[4-(4,4-difluorocyclohexyl)-3-methyl-5-oxopiperazin-1-yl]carbonyl}-4-fluorobenzyl)-4,5-dimethylpyridazin-3(2H)-one trifluoroacetate;
6-(3-{[4-(3,3-difluorocyclopentyl)-3-methyl-5-oxopiperazin-1-yl]carbonyl}-4-fluorobenzyl)-4,5-dimethylpyridazin-3(2H)-one trifluoroacetate;
6-(3-{[4-(4,4-dimethylcyclohexyl)-3-methyl-5-oxopiperazin-1-yl]carbonyl}-4-fluorobenzyl)-4,5-dimethylpyridazin-3(2H)-one trifluoroacetate;
6-(4-fluoro-3-{[3-methyl-5-oxo-4-(tetrahydro-2h-pyran-3-yl)piperazin-1-yl]carbonyl}benzyl)-4,5-dimethylpyridazin-3(2H)-one trifluoroacetate;
6-(4-fluoro-3-{[3-methyl-5-oxo-4-(tetrahydrofuran-3-yl)piperazin-1-yl]carbonyl}benzyl)-4,5-dimethylpyridazin-3(2H)-one trifluoroacetate;
6-(3-{[4-(2,2-difluoro-1-phenylethyl)-3-methyl-5-oxopiperazin-1-yl]carbonyl}-4-fluorobenzyl)-4,5-dimethylpyridazin-3(2H)-one trifluoroacetate;
6-(3-{[4-(3,4-dihydro-2H-chromen-3-yl)-3-methyl-5-oxopiperazin-1-yl]carbonyl}-4-fluorobenzyl)-4,5-dimethylpyridazin-3(2H)-one trifluoroacetate;
4-ethyl-6-(4-fluoro-3-{[3-oxo-4-(tetrahydro-2H-pyran-3-yl)piperazin-1-yl]carbonyl}benzyl)-3-oxo-2,3-dihydropyridazin-1-ium trifluoroacetate;
4-ethyl-6-(4-fluoro-3-{[3-oxo-4-(2,2,2-trifluoroethyl)piperazin-1-yl]carbonyl}benzyl)-3-oxo-2,3-dihydropyridazin-1-ium trifluoroacetate;
3-(4-fluoro-3-{[(9aS)-4-oxooctahydro-2H-pyrido[1,2-a]pyrazin-2-yl]carbonyl}benzyl)-4-methyl-6-oxo-5-(trifluoromethyl)-1,6-dihydropyridazin-1-ium trifluoroacetate;
3-{4-fluoro-3-[(6-oxohexahydropyrazino[2,1-c][1,4]oxazin-8(1H)-yl)carbonyl]benzyl}-4-methyl-6-oxo-5-(trifluoromethyl)-1,6-dihydropyridazin-1-ium trifluoroacetate;
6-{3-[(4-ethyl-3-methyl-5-oxopiperazin-1-yl)carbonyl]-4-fluorobenzyl}-4,5-dimethyl-3-oxo-2,3-dihydropyridazin-1-ium trifluoroacetate;
6-(4-fluoro-3-{[4-(4-methoxybenzyl)-3-methyl-5-oxopiperazin-1-yl]carbonyl}benzyl)-4,5-dimethyl-3-oxo-2,3-dihydropyridazin-1-ium trifluoroacetate;
6-(4-fluoro-3-{[3-methyl-5-oxo-4-(2,2,2-trifluoroethyl)piperazin-1-yl]carbonyl}benzyl)-4,5-dimethyl-3-oxo-2,3-dihydropyridazin-1-ium trifluoroacetate;
6-[3-({4-[(1R,4S)-bicyclo[2.2.1]hept-2-yl]-3-methyl-5-oxopiperazin-1-yl-}carbonyl)-4-fluorobenzyl]-4,5-dimethyl-3-oxo-2,3-dihydropyridazin-1-ium trifluoroacetate;
3-(4-fluoro-3-{[3-oxo-4-(tetrahydro-2h-pyran-3-yl)piperazin-1-yl]carbonyl}benzyl)-4-methyl-6-oxo-5-(trifluoromethyl)-1,6-dihydropyridazin-1-ium trifluoroacetate;
3-(4-fluoro-3-{[3-oxo-4-(tetrahydro furan-3-yl)piperazin-1-yl]carbonyl}benzyl)-4-methyl-6-oxo-5-(trifluoromethyl)-1,6-dihydropyridazin-1-ium trifluoroacetate;
6-{3-[(4-ethyl-3-oxopiperazin-1-yl)carbonyl]-4-fluorobenzyl}-5-methyl-4-(trifluoromethyl)pyridazin-3(2H)-one;
4-ethyl-6-[4-fluoro-3-({3-oxo-4-[(3S)-tetrahydro-2H-pyran-3-yl]piperazin-1-yl}carbonyl)benzyl]pyridazin-3(2H)-one;
4-ethyl-6-[4-fluoro-3-({3-oxo-4-[(3R)-tetrahydro-2H-pyran-3-yl]piperazin-1-yl}carbonyl)benzyl]pyridazin-3(2H)-one;
3-(4-fluoro-3-{[3-oxo-4-(tetrahydro-2H-pyran-4-yl)piperazin-1-yl]carbonyl}benzyl)-4-methyl-6-oxo-5-(trifluoromethyl)-1,6-dihydropyridazin-1-ium trifluoroacetate;
3-{3-[(4-ethyl-3-methyl-5-oxopiperazin-1-yl)carbonyl]-4-fluorobenzyl}-4-methyl-6-oxo-5-(trifluoromethyl)-1,6-dihydropyridazin-1-ium trifluoroacetate;
4-ethyl-6-(4-fluoro-3-{[3-oxo-4-(1,2,3,4-tetrahydronaphthalen-2-yl)piperazin-1-yl]carbonyl}benzyl)pyridazin-3(2H)-one;
6-{3-[(4-cyclopentyl-3-oxopiperazin-1-yl)carbonyl]-4-fluorobenzyl}-3-oxo-4-(pentafluoroethyl)-2,3-dihydropyridazin-1-ium trifluoroacetate;
6-(4-fluoro-3-{[4-(3-fluorocyclopentyl)-3-oxopiperazin-1-yl]carbonyl}benzyl)-4,5-dimethylpyridazin-3(2H)-one;
6-(3-{[(3R)-4-cyclopentyl-3-methyl-5-oxopiperazin-1-yl]carbonyl}-4-fluorobenzyl)-4-(trifluoromethyl)pyridazin-3(2H)-one;
6-(3-{[(3S)-4-cyclopentyl-3-methyl-5-oxopiperazin-1-yl]carbonyl}-4-fluorobenzyl)-4-(trifluoromethyl)pyridazin-3(2H)-one;
6-[4-fluoro-3-({3-oxo-4-[(3S)-tetrahydro-2H-pyran-3-yl]piperazin-1-yl}carbonyl)benzyl]-4-(trifluoromethyl)pyridazin-3(2H)-one;
6-[4-fluoro-3-({3-oxo-4-[(3R)-tetrahydro-2H-pyran-3-yl]piperazin-1-yl}carbonyl)benzyl]-4-(trifluoromethyl)pyridazin-3(2H)-one;
6-(3-{[(3S)-4-ethyl-3-methyl-5-oxopiperazin-1-yl]carbonyl}-4-fluorobenzyl)-5-methyl-4-(trifluoromethyl)pyridazin-3(2H)-one;
6-(3-{[(3R)-4-ethyl-3-methyl-5-oxopiperazin-1-yl]carbonyl}-4-fluorobenzyl)-5-methyl-4-(trifluoromethyl)pyridazin-3(2H)-one;
6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one;
6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one;
4-ethyl-6-[4-fluoro-3-({3-oxo-4-[(2S)-1,2,3,4-tetrahydronaphthalen-2-yl]piperazin-1-yl}carbonyl)benzyl]pyridazin-3(2H)-one;
4-ethyl-6-[4-fluoro-3-({3-oxo-4-[(2R)-1,2,3,4-tetrahydronaphthalen-2-yl]piperazin-1-yl}carbonyl)benzyl]pyridazin-3(2H)-one;
and pharmaceutically acceptable salts, stereoisomers, free bases and tautomers thereof.

Further particular compounds within the scope of the present invention are:
6-[4-Fluoro-3-({4-[(1S)-1-methylpropyl]-3-oxopiperazin-1-yl}carbonyl)benzyl]-4,5-dimethylpyridazin-3(2H)-one;
6-(4-Fluoro-3-{[4-(2-methoxy-1-methylethyl)-3-oxopiperazin-1-yl]carbonyl}benzyl)-4,5-dimethylpyridazin-3(2H)-one;
6-{3-[(4-Cyclobutyl-3-methyl-5-oxopiperazin-1-yl)carbonyl]-4-fluorobenzyl}-4,5-dimethylpyridazin-3(2H)-one;
6-{3-[(4-Cyclobutyl-3-ethyl-5-oxopiperazin-1-yl)carbonyl]-4-fluorobenzyl}-4,5-dimethylpyridazin-3(2H)-one;
6-(3-{[4-(3-Chlorophenyl)-3-methyl-5-oxopiperazin-1-yl]carbonyl}-4-fluorobenzyl)-4,5-dimethylpyridazin-3(2H)-one;

4-((2S)-4-{5-[(4,5-Dimethyl-6-oxo-1,6-dihydropyridazin-3-yl)methyl]-2-fluorobenzoyl}-2-methyl-6-oxopiperazin-1-yl)benzonitrile;

6-(3-{[4-(1-Ethylpropyl)-3-oxopiperazin-1-yl]carbonyl}-4-fluorobenzyl)-4,5-dimethylpyridazin-3(2H)-one;

6-[4-Fluoro-3-({4-[(1R)-1-methylpropyl]-3-oxopiperazin-1-yl}carbonyl)benzyl]-4,5-dimethylpyridazin-3(2H)-one;

6-[4-Fluoro-3-({4-[(1S)-2-methoxy-1-methylethyl]-3-oxopiperazin-1-yl}carbonyl)benzyl]-4,5-dimethylpyridazin-3(2H)-one;

6-(4-Fluoro-3-{[4-(2-methoxyethyl)-3-oxopiperazin-1-yl]carbonyl}benzyl)-4,5-dimethylpyridazin-3(2H)-one;

6-(3-{[4-(2-Ethoxyethyl)-3-oxopiperazin-1-yl]carbonyl}-4-fluorobenzyl)-4,5-dimethylpyridazin-3(2H)-one;

6-(4-Fluoro-3-{[4-(2-isopropoxyethyl)-3-oxopiperazin-1-yl]carbonyl}benzyl)-4,5-dimethylpyridazin-3(2H)-one;

6-(4-Fluoro-3-{[4-(2-hydroxy-2-methylpropyl)-3-oxopiperazin-1-yl]carbonyl}benzyl)-4,5-dimethylpyridazin-3(2H)-one;

4-((2S)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-(3-{[(3R)-4-Cyclobutyl-3-methyl-5-oxopiperazin-1-yl]carbonyl}-4-fluorobenzyl)-4,5-dimethylpyridazin-3(2H)-one;

6-(3-{[(3S)-4-Cyclobutyl-3-methyl-5-oxopiperazin-1-yl]carbonyl}-4-fluorobenzyl)-4,5-dimethylpyridazin-3(2H)-one;

6-(3-{[(3S)-4-(3-Chlorophenyl)-3-methyl-5-oxopiperazin-1-yl]carbonyl}-4-fluorobenzyl)-4,5-dimethylpyridazin-3(2H)-one;

6-(3-{[(3R)-4-(3-Chlorophenyl)-3-methyl-5-oxopiperazin-1-yl]carbonyl}-4-fluorobenzyl)-4,5-dimethylpyridazin-3(2H)-one;

6-[4-Fluoro-3-({4-[(1R)-2-methoxy-1-methylethyl]-3-oxopiperazin-1-yl}carbonyl)benzyl]-4,5-dimethylpyridazin-3(2H)-one;

6-(3-{[(3R)-4-Cyclobutyl-3-ethyl-5-oxopiperazin-1-yl]carbonyl}-4-fluorobenzyl)-4,5-dimethylpyridazin-3(2H)-one;

6-(3-{[(3S)-4-Cyclobutyl-3-ethyl-5-oxopiperazin-1-yl]carbonyl}-4-fluorobenzyl)-4,5-dimethylpyridazin-3(2H)-one;

6-[3-({4-[(1R)-1,2-Dimethylpropyl]-3-oxopiperazin-1-yl}carbonyl)-4-fluorobenzyl]-4,5-dimethylpyridazin-3(2H)-one;

6-[3-({4-[(1S)-1,2-Dimethylpropyl]-3-oxopiperazin-1-yl}carbonyl)-4-fluorobenzyl]-4,5-dimethylpyridazin-3(2H)-one;

6-{3-[(4-Cyclohexyl-3-ethyl-5-oxopiperazin-1-yl)carbonyl]-4-fluorobenzyl}-4,5-dimethylpyridazin-3(2H)-one;

6-{3-[(4-Cyclopentyl-3-isobutyl-5-oxopiperazin-1-yl)carbonyl]-4-fluorobenzyl}-4,5-dimethylpyridazin-3(2H)-one;

6-{3-[(4-Cyclopentyl-3-ethyl-5-oxopiperazin-1-yl)carbonyl]-4-fluorobenzyl}-4,5-dimethylpyridazin-3(2H)-one;

6-(3-{[(3R)-4-(4-Chloro-3-fluorophenyl)-3-methyl-5-oxopiperazin-1-yl]carbonyl}-4-fluorobenzyl)-4,5-dimethylpyridazin-3(2H)-one;

6-(3-{[4-(3,3-Difluorocyclobutyl)-3-methyl-5-oxopiperazin-1-yl]carbonyl}-4-fluorobenzyl)-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)benzonitrile;

6-(3-{[(3R)-4-(3-Chlorophenyl)-3-methyl-5-oxopiperazin-1-yl]carbonyl}-4-fluorobenzyl)-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-[4-Fluoro-3-({3-oxo-4-[(1S)-2,2,2-trifluoro-1-methylethyl]piperazin-1-yl}carbonyl)benzyl]-4,5-dimethylpyridazin-3(2H)-one;

6-(3-{[(3R)-4-(3,5-Difluorophenyl)-3-methyl-5-oxopiperazin-1-yl]carbonyl}-4-fluorobenzyl)-4,5-dimethylpyridazin-3(2H)-one;

6-(3-{[(3R)-4-(4-Chlorophenyl)-3-methyl-5-oxopiperazin-1-yl]carbonyl}-4-fluorobenzyl)-4,5-dimethylpyridazin-3(2H)-one;

6-(4-Fluoro-3-{[(3R)-3-methyl-5-oxo-4-(2-thienyl)piperazin-1-yl]carbonyl}benzyl)-4,5-dimethylpyridazin-3(2H)-one;

6-(3-{[(3R)-4-(4-Chloro-2-fluorophenyl)-3-methyl-5-oxopiperazin-1-yl]carbonyl}-4-fluorobenzyl)-4,5-dimethylpyridazin-3(2H)-one;

5-((2R)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-(3-{[(3R)-4-(3-Chloro-5-fluorophenyl)-3-methyl-5-oxopiperazin-1-yl]carbonyl}-4-fluorobenzyl)-4,5-dimethylpyridazin-3(2H)-one;

6-(3-{[(3R)-4-(3-Chloro-4-fluorophenyl)-3-methyl-5-oxopiperazin-1-yl]carbonyl}-4-fluorobenzyl)-4,5-dimethylpyridazin-3(2H)-one;

6-[4-Fluoro-3-({3-oxo-4-[(1R)-2,2,2-trifluoro-1-methylethyl]piperazin-1-yl}carbonyl)benzyl]-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)-3-fluorobenzonitrile;

3-((2R)-4-{5-[(4,5-Dimethyl-6-oxo-1,6-dihydropyridazin-3-yl)methyl]-2-fluorobenzoyl}-2-methyl-6-oxopiperazin-1-yl)-5-fluorobenzonitrile;

6-(3-{[(3R)-4-(3,4-Difluorophenyl)-3-methyl-5-oxopiperazin-1-yl]carbonyl}-4-fluorobenzyl)-4,5-dimethylpyridazin-3(2H)-one;

6-(3-{[4-(1-Cyclopropylethyl)-3-oxopiperazin-1-yl]carbonyl}-4-fluorobenzyl)-4,5-dimethylpyridazin-3(2H)-one;

6-(3-{[(3R)-4-(5-Chloro-2-fluorophenyl)-3-methyl-5-oxopiperazin-1-yl]carbonyl}-4-fluorobenzyl)-4,5-dimethylpyridazin-3(2H)-one;

6-(3-{[(3R)-4-(3-Chloro-2-fluorophenyl)-3-methyl-5-oxopiperazin-1-yl]carbonyl}-4-fluorobenzyl)-4,5-dimethylpyridazin-3(2H)-one;

6-(3-{[(3R)-4-Cyclopentyl-3-isopropyl-5-oxopiperazin-1-yl]carbonyl}-4-fluorobenzyl)-4,5-dimethylpyridazin-3(2H)-one;

6-(3-{[(3S)-4-(4-Chloro-3-fluorophenyl)-3-methyl-5-oxopiperazin-1-yl]carbonyl}-4-fluorobenzyl)-4,5-dimethylpyridazin-3(2H)-one;

6-(3-{[(3S)-4-(3,3-Difluorocyclobutyl)-3-methyl-5-oxopiperazin-1-yl]carbonyl}-4-fluorobenzyl)-4,5-dimethylpyridazin-3(2H)-one;

6-(3-{[(3R)-4-(3,3-Difluorocyclobutyl)-3-methyl-5-oxopiperazin-1-yl]carbonyl}-4-fluorobenzyl)-4,5-dimethylpyridazin-3(2H)-one;

6-{4-Fluoro-3-[(4-isopropyl-3-oxopiperazin-1-yl)carbonyl]benzyl}-4,5-dimethylpyridazin-3(2H)-one;

6-[4-Fluoro-3-({4-[(trans)-3-fluorocyclopentyl]-3-oxopiperazin-1-yl}carbonyl)benzyl]-4,5-dimethylpyridazin-3(2H)-one;

and pharmaceutically acceptable salts, stereoisomers, free bases and tautomers thereof.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, palmitic, gluconic, ascorbic, phenylacetic, aspartic, cinnamic, pyruvic, ethanesulfonic, ethane, disulfonic, valeric, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, lysine, betaine caffeine, choline, N,N$^1$-dibenzylethylenediamine, ethylamine, diethylamine, 2-diethylaminoethanol, 2-dimethylaminoethanol, ethanolamine, diethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine, dicyclohexylamine, butylamine, benzylamine, phenylbenzylamine, tromethamine and the like.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The present invention provides compounds for use in therapy.

The invention provides compounds for use in the treatment or prevention of conditions which can be ameliorated by the inhibition of poly(ADP-ribose)polymerase (PARP) (see, for example, *Nature Review Drug Discovery* (2005) 4:421-440).

Thus, the present invention provides the use of a compound of formula I for the manufacture of a medicament for the treatment or prevention of conditions which can be ameliorated by the inhibition of poly(ADP-ribose)polymerase (PARP). The invention also provides the use of a compound of formula I for the manufacture of a medicament for the treatment or prevention of conditions described herein.

The present invention also provides a method for the treatment or prevention of conditions which can be ameliorated by the inhibition of poly(ADP-ribose)polymerase (PARP), which method comprises administration to a patient in need thereof of an effective amount of a compound of formula I or a composition comprising a compound of formula I.

The PARP inhibitors of the present invention are useful for the treatment of the diseases specified in WO 2005/082368.

PARP inhibitors have been demonstrated as being useful for treatment of inflammation diseases (see *Pharmacological Research* (2005) 52:72-82 and 83-92).

The compounds of the invention are useful for the treatment of inflammatory diseases, including conditions resulting from organ transplant rejection, such as; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympatheticophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDSrelated neurodegeneration and Alzheimer's disease, infectious meningitis, encephalomyelitis, Parkinson's disease, Huntington's disease, amyotrophic lateral sclerosis and viral or autoimmune encephalitis; diabetic complications, including, but not limited to, immune-complex vasculitis, systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, brain and spinal cord trauma and multiple organ dysfunction syndrome (MODS) (multiple organ failure (MOF)). The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g. by a chemotherapeutic agent that is administered as a treatment for cancer.

Thus, the present invention provides a compound of formula I for use in the treatment or prevention of inflammatory diseases.

The present invention also provides a method for the treatment or prevention of inflammatory diseases, which method comprises administration to a patient in need thereof of an effective amount of a compound of formula I or a composition comprising a compound of formula I.

PARP inhibitors have also been shown to be useful for treating acute and chronic myocardial diseases (see *Pharmacological Research* (2005) 52:34-43). For instance, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). These results make it reasonable to assume that PARP inhibitors could salvage previously ischemic heart or reperfusion injury of skeletal muscle tissue (*PNAS* (1997) 94:679-683). Similar findings have also been reported in pigs (*Eur. J. Pharmacol.* (1998) 359:143-150 and *Ann. Thorac. Surg.* (2002) 73:575-581) and in dogs (*Shock.* (2004) 21:426-32).

PARP inhibitors have been demonstrated as being useful for treating certain vascular diseases, septic shock, ischemic injury and neurotoxicity (*Biochim. Biophys. Acta* (1989) 1014:1-7; *J. Clin. Invest.* (1997) 100: 723-735). PARP has also been demonstrated to play a role in the pathogenesis of hemorrhagic shock (*PNAS* (2000) 97:10203-10208).

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine, and cornea.

Thus, the present invention provides a compound of formula I for use in the treatment or prevention of reperfusion injuries.

The present invention also provides a method for the treatment or prevention of reperfusion injuries, which method comprises administration to a patient in need thereof of an effective amount of a compound of formula I or a composition comprising a compound of formula I.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a compound of formula I for use in the treatment or prevention of ischemic conditions.

The present invention also provides a method for the treatment or prevention of ischemic conditions, which method comprises administration to a patient in need thereof of an effective amount of a compound of formula I or a composition comprising a compound of formula I.

The present invention provides a compound of formula I for use in the treatment or prevention of stroke.

The present invention also provides a method for the treatment or prevention of stroke, which method comprises administration to a patient in need thereof of an effective amount of a compound of formula I or a composition comprising a compound of formula I.

The compounds of the instant invention is also be useful for the treatment or prevention of chronic or acute renal failure.

Thus, the present invention provides a compound of formula I for use in the treatment or prevention of renal failure.

The present invention also provides a method for the treatment or prevention of renal failure, which method comprises administration to a patient in need thereof of an effective amount of a compound of formula I or a composition comprising a compound of formula I.

The compounds of the instant invention may also be useful for the treatment or prevention of vascular diseases other than cardiovascular diseases, such as peripheral arterial occlusion, thromboangitis obliterans, Reynaud's disease and phenomenon, acrocyanosis, erythromelalgia, venous thrombosis, varicose veins, arteriovenous fistula, lymphedema and lipedema.

Thus, the present invention provides a compound of formula I for use in the treatment or prevention of vascular diseases other than cardiovascular diseases.

The present invention also provides a method for the treatment or prevention of vascular diseases other than cardiovascular diseases, which method comprises administration to a patient in need thereof of an effective amount of a compound of formula I or a composition comprising a compound of formula I.

The compounds of the instant invention may also be useful for the treatment or prevention of cardiovascular diseases such as chronic heart failure, atherosclerosis, congestive heart failure, circulatory shock, cardiomyopathy, cardiac transplant, myocardialinfarction, and a cardiac arrhythmia, such as atrial fibrillation, supraventricular tachycardia, atrial flutter, and paroxysmal atrial tachycardia.

Thus, the present invention provides a compound of formula I for use in the treatment or prevention of cardiovascular diseases.

The present invention also provides a method for the treatment or prevention of cardiovascular diseases, which method comprises administration to a patient in need thereof of an effective amount of a compound of formula I or a composition comprising a compound of formula I.

In vitro and in vivo experiments have demonstrated that PARP inhibitors can be used for the treatment or prevention of autoimmune diseases such as Type I diabetes and diabetic complications (*Pharmacological Research* (2005) 52:60-71).

The compounds of this invention may also be useful for the treatment and prevention of diabetes mellitus, including Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by (3-cell toxins. The compounds of this invention may also be useful for the treatment or prevention of diabetic complications, such as diabetic cataract, glaucoma, retinopathy, nephropathy, (such asmicroaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, a bacterial infection, and cardiomyopathy.

Thus, the present invention provides a compound of formula I for use in the treatment or prevention of diabetes.

The present invention also provides a method for the treatment or prevention of diabetes, which method comprises administration to a patient in need thereof of an effective amount of a compound of formula I or a composition comprising a compound of formula I.

The compounds of this invention may also be useful for the treatment or prevention of cancer including solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; Lymphomas such as Hodgkin's disease, non-Hodgkin's Lymphoma, Multiple myeloma, Waldenstrom's macroglobulinemia, Heavy chain disease and Polycythemia vera; CNS and brain cancers such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a compound of formula I for use in the treatment or prevention of cancer.

The present invention also provides a method for the treatment or prevention of cancer, which method comprises administration to a patient in need thereof of an effective amount of a compound of formula I or a composition comprising a compound of formula I.

The compounds of the present invention may also be used for the treatment of cancer which is deficient in Homologous Recombination (HR) dependent DNA DSB repair activity (see WO 2006/021801).

The HR dependent DNA DSB repair pathway repairs double-strand breaks (DSBs) in DNA via homologous mechanisms to reform a continuous DNA helix (*Nat. Genet.* (2001) 27(3):247-254). The components of the HR dependent DNA DSB repair pathway include, but are not limited to, ATM (NM-000051), RAD51 (NM-002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9. Other proteins involved in the HR dependent DNA DSB repair pathway include regulatory factors such as EMSY (*Cell* (2003) 115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, *Science* (2001) 291: 1284-1289) and include the components listed above.

The present invention provides a compound of formula I for use in the treatment or prevention of a cancer which is deficient in HR dependent DNA DSB repair activity.

The present invention also provides a method for the treatment or prevention of a cancer which is deficient in HR dependent DNA DSB repair activity, which method comprises administration to a patient in need thereof of an effective amount of a compound of formula I or a composition comprising a compound of formula I In an embodiment the cancer cells are deficient in the HR dependent DNA DSB repair activity of one or more phenotypes selected from ATM (NM-000051), RAD51 (NM- 002875), RAD51 L1 (NM-002877), RAD51C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2 (PARP-2), CTPS, RPA, RPA1, RPA2, RPA3, XPD, ERCC1, XPF, MMS19, RAD51p, RAD51D, DMC1, XRCCR, RAD50, MRE11, NB51, WRN, BLMKU70, RU80, ATRCHK1, CHK2, FANCA, FANCB, FANCC, FANCD1, FANCD2, FANCE, FANCF, FANCG, RAD1 and RAD9.

In another embodiment, the cancer cells have a BRCA1 and/or a BRCA2 deficient phenotype. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (*Cell* (2003) 115:523-535).

BRCA-1 and BRCA-2 are known tumor suppressors whose wild-type alleles are frequently lost in tumors of heterozygous carriers (*Oncogene*, (2002) 21(58):8981-93; *Trends Mol Med.*, (2002) 8(12):571-6). The association of BRCA-1 and/or BRCA-2 mutations with breast cancer has been well-characterized (*Exp Clin Cancer Res.*, (2002) 21 (3 Suppl):9-12). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in EP 699 754, EP 705 903, *Genet. Test* (1992) 1:75-83; *Cancer Treat Res* (2002) 107:29-59; *Neoplasm* (2003) 50(4):246-50; *Ceska Gynekol* (2003) 68(1):11-16). Determination of amplification of the BRCA-2 binding factor EMSY is described in *Cell* 115:523-535. PARP inhibitors have been demonstrated as being useful for the specific killing of BRCA-1 and BRCA-2 deficient tumors (*Nature* (2005) 434:913-916 and 917-921; and *Cancer Biology & Therapy* (2005) 4:934-936).

Thus, the present invention provides a compound of formula I for use in the treatment or prevention of BRCA-1 or BRCA-2 deficient tumors.

The present invention also provides a method for the treatment or prevention of BRCA-1 or BRCA-2 deficient tumors, which method comprises administration to a patient in need thereof of an effective amount of a compound of formula I or a composition comprising a compound of formula I.

In an embodiment, the PARP inhibitors of the present can be used in prophylactic therapy for elimination of BRCA2-deficient cells (see, *Cancer Res.* (2005) 65:10145).

The compounds of this invention may be useful for the treatment or prevention of neurodegenerative diseases, including, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a compound of formula I for use in the treatment or prevention of neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the present invention may also be useful for the treatment or prevention of retroviral infection (U.S. Pat. No. 5,652,260 and *J. Virology*, (1996) 70(6):3992-4000), retinal damage (*Curr. Eye Res.* (2004), 29:403), skin senescence and UV-induced skin damage (U.S. Pat. No. 5,589,483 and *Biochem. Pharmacol* (2002) 63:921). It has also been demonstrated that efficient retroviral infection of mammalian cells is blocked by the inhibition of PARP activity. Such inhibition of recombinant retroviral vector infections has been shown to occur in various different cell types).

The compounds of the invention are useful for the treatment or prevention of premature aging and postponing the onset of age-related cellular dysfunction (*Biochem. Biophys. Res. Comm.* (1994) 201(2):665-672 and *Pharmacological Research* (2005) 52:93-99).

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal such as a vertebrate animal, a mammal and preferably a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection or by a continuous intravenous delivery device. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The instant compounds are also useful in combination with anti-cancer agents or chemotherapeutic agents.

PARP inhibitors have been shown to enhance the efficacy of anticancer drugs (*Pharmacological Research* (2005) 52:25-33), including platinum compounds such as cisplatin and carboplatin (*Cancer Chemother Pharmacol* (1993) 33:157-162 and *Mol Cancer Ther* (2003) 2:371-382). PARP inhibitors have been shown to increase the antitumor activity of topoisomerase I inhibitors such as Irinotecan and Topotecan (*Mol Cancer Ther* (2003) 2:371-382; and *Clin Cancer Res* (2000) 6:2860-2867) and this has been demonstrated in in vivo models (*J Natl Cancer Inst* (2004) 96:56-67).

PARP inhibitors have been shown to act as radiation sensitizers. PARP inhibitors have been reported to be effective in radiosensitizing (hypoxic) tumor cells and effective in preventing tumor cells from recovering from potentially lethal (*Br. J. Cancer* (1984) 49(Suppl. VI):34-42; and *Int. J. Radiat. Bioi.* (1999) 75:91-100) and sub-lethal (*Clin. Oncol.* (2004) 16(1):29-39) damage of DNA after radiation therapy, presumably by their ability to prevent DNA strand break rejoining and by affecting several DNA damage signaling pathways.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a compound of formula I and an anti-cancer agent for simultaneous, separate or sequential administration.

The present invention also provides a compound of formula I for use in the manufacture of a medicament for use as an adjunct in cancer therapy or for potentiating tumor cells for treatment with ionizing radiation or chemotherapeutic agents.

The present invention also provides a method of chemotherapy or radiotherapy, which method comprises administration to a patient in need thereof of an effective amount of a compound of formula I or a composition comprising a compound of formula I in combination with ionizing radiation or chemotherapeutic agents.

In combination therapy, the instant compounds and another anticancer agent can be administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamine, carboplatin, altretamine, prednimustine, dibromodulcitol, ranimustine, fotemustine, nedaplatin, aroplatin, oxaliplatin, temozolomide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulphonyl-daunorubicin (see WO 00/50032).

In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes: dacarbazine, procarbazine and temozolomide; platinum containing complexes: cisplatin, carboplatin, aroplatin and oxaliplatin.

In an embodiment, the alkylating agent is dacarbazine. Dacarbazine can be administered to a subject at dosages ranging from about 150 mg/m2 (of a subject's body surface area) to about 250 mg/m2. In another embodiment, dacarbazine is administered intravenously to a subject once per day for five consecutive days at a dose ranging from about 150 mg/m2 to about 250 mg/m2.

In an embodiment, the alkylating agent is procarbazine. Procarbazine can be administered to a subject at dosages ranging from about 50 mg/m2 (of a subject's body surface area) to about 100 mg/m2. In another embodiment, procarbazine is administered intravenously to a subject once per day for five consecutive days at a dose ranging from about 50 mg/m2 to about 100 mg/m2.

PARP inhibitors have been shown to restore susceptibility to the cytotoxic and antiproliferative effects of temozolomide (TMZ) (see *Curr Med Chem* (2002) 9:1285-1301 and *Med Chem Rev Online* (2004) 1:144-150). This has been demonstrated in a number of in vitro models (*Br J Cancer* (1995) 72:849-856; *Br J Cancer* (1996) 74:1030-1036; *Mol Pharmacol* (1997) 52:249-258; *Leukemia* (1999) 13:901-909; *Glia* (2002) 40:44-54; and *Clin Cancer Res* (2000) 6:2860-2867 and (2004) 10:881-889) and in vivo models (*Blood* (2002) 99:2241-2244; *Clin Cancer Res* (2003) 9:5370-5379 and *J Natl Cancer Inst* (2004) 96:56-67).

In an embodiment, the alkylating agent is temozoloamide. Temozolomide can be administered to a subject at dosages ranging from about 150 mg/m2 (of a subject's body surface area) to about 200 mg/m2. In another embodiment, temozolomide is administered orally to an animal once per day for five consecutive days at a dose ranging from about 150 mg/m2 to about 200 mg/m2.

Examples of anti-mitotic agents include: allocolchicine, halichondrin B, colchicine, colchicine derivative, dolstatin 10, maytansine, rhizoxin, thiocolchicine and trityl cysteine.

An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilising agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, exatecan, gimetecan, diflomotecan, silyl-camptothecins, 9-aminocamptothecin, camptothecin, crisnatol, mitomycin C, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna; non-camptothecin topoisomerase-1 inhibitors such as indolocarbazoles; and dual topoisomerase-1 and II inhibitors such as benzophenazines, XR 20 115761MLN 576 and benzopyridoindoles.

In an embodiment, the topoisomerase inhibitor is irinotecan. Irinotecan can be administered to a subject at dosages ranging from about 50 mg/m2 (of a subject's body surface area) to about 150 mg/m2. In another embodiment, irinotecan is administered intravenously to a subject once per day for five consecutive days at a dose ranging from about 50 mg/m2 to about 150 mg/m2 on days 1-5, then again intravenously once per day for five consecutive days on days 28-32 at a dose ranging from about 50 mg/m2 to about 150 mg/m2, then again intravenously once per day for five consecutive days on days 55-59 at a dose ranging from about 50 mg/m2 to about 150 mg/m2.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer* (1999), 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS* (1992) 89:7384; *JNCI* (1982) 69:475; *Arch. Opthalmol.* (1990) 108: 573; *Anat. Rec.* (1994) 238:68; *FEBS Letters* (1995) 372:83; *Clin, Orthop.* (1995) 313:76; *J. Mol. Endocrinol.* (1996) 16:107; *Jpn. J. Pharmacol.* (1997) 75:105; *Cancer Res.* (1997) 57:1625 (1997); *Cell* (1998) 93:705; *Intl. J. Mol. Med.* (1998) 2:715; *J. Biol. Chem.* (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see *J. Lab. Clin. Med.* (1985) 105:141-145), and antibodies to VEGF (see *Nature Biotechnology* (1999) 17:963-968; Kim et al (1993) *Nature* 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* (2000) 38:679-692). Examples of such agents that modulate or inhibit the coagulation and fibrinolysis pathways include, but are not limited to, heparin (see *Thromb. Haemost.* (1998) 80:10-23), low molecular weight heparins and carboxypeptidase U inhibitors (also known as inhibitors of active thrombin activatable fibrinolysis inhibitor [TAFIa]) (see *Thrombosis Res.* (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, staurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

PAPR inhibitors have also been shown to prevent the appearance of necrosis induced by selective N3-adenine methylating agents such as $MeOSO_2(CH_2)$-lexitropsin (Me-Lex) (*Pharmacological Research* (2005) 52:25-33).

In an embodiment, the compounds of the present invention are useful for the treatment or prevention of the appearance of necrosis induced by selective N3-adenine methylating agents such as $MeOSO_2(CH_2)$-lexitropsin (Me-Lex).

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Opthalmol. Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepeside®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorine®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50e); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid); Uracil Mustard (Uracil Mustard Capsules®); valrubicin (Valstar®); vinblastine (Velban®); vincristine (Oncovin®); vinorelbine (Navelbine®); vorinostat (Zolinza®); zoledronate (Zometa®), nilotinib (Tasigna®); and dasatinib (Sprycel®).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "adjunct" refers to the use of compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-αinterleukin-12, pentosan polysulfate, a cyclooxygenase inhibitor, carboxyamidotriazole, combretastatin A-4, squalamine, 6-O- chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

The compounds of this invention were prepared according to the following procedures. All variables within the formulae are as defined above.

Abbreviations used in the description of the chemistry and in the examples that follow are:

AcOH (acetic acid); DCM (dichloromethane); DIPEA (N,N'-Diisopropylethylamine); DMA (N,N-dimethylacetamide); DMAP (4-dimethyaminoooyridine); DMF (dimethylformamide); DMSO (dimethyl sulfoxide); eq. (equivalent); EtOAc (ethyl acetate); HBTU (O-Benzotriazole-N,N,N',N'-tetramethyl-uronium-hexafluoro-phosphate); NaH (sodium hydride); NMR (nuclear magnetic resonance); PyBOP (1H-benzotriazol-1-yl-oxytripyrrolidinophosphonium); RP-HPLC (reverse phase high performance liquid chromatography); RT (room temperature); sat. aq. (saturated aqueous); TBTU (O-(1H-benzotriazol-1-yl)-N,N,N; N'-tetramethyluronium tetrafluoroborate); TEA (triethylamine); TFA (trifluoroacetic acid); and THF (tetrahydrofuran).

Compounds of formula I can be prepared by condensation of a compound of formula IA with a compound of formula IB:

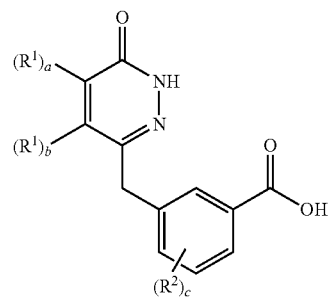

(IA)

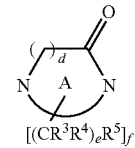

(IB)

wherein a, b, c, d, e, f, A, $R^1$, $R^2$, $R^3$, $R^4$ and $R^5$ are as defined above. The reaction can generally be carried out in the presence of coupling agents such as HBTU, TBTU, HATU and PyBOP, with a base like DIPEA or TEA, optionally with a catalyst like DMAP and in a solvent such as DMA or DMF at about room temperature. Analogous coupling conditions can be used in any step in the synthesis of compounds of formula I using appropriate combinations of starting materials.

Compounds of formula IA can be prepared by concurrent hydrolysis and decarboxylation of a compound of formula IC:

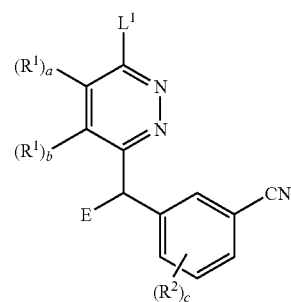

(IC)

wherein a, b, c, $R^1$ and $R^2$ are as defined above, E is an electron withdrawing group, such as cyano and $L^1$ is a leaving group such as halogen, for example chlorine. The reaction is generally carried out under acidic conditions. For example, the reaction may be carried out in solvents such as AcOH and HCl at reflux, followed by treatment with NaOAc in acetic acid to displace the $L^1$ group.

Compounds of formula IC can be prepared by reacting a compound of formula ID with a compound of formula IE:

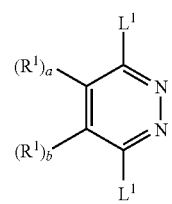

(ID)

(IE)

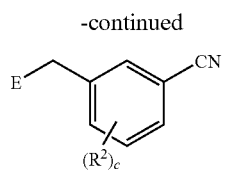

wherein a, b, c, $R^1$, $R^2$, E and each $L^1$ is independently as defined above. The reaction is generally carried out in the presence of a base such as NaH, in a solvent such as DMF at about 0° C. to room temperature. When two different $R^1$ groups are present in the compounds of formula ID the two isomeric products obtained from this reaction can be separated using conventional methods, such as column chromatography on silica, or HPLC separation. Alternatively, the isomeric mixture of the two compounds of formula IC can be used in subsequent reactions and separated at a later stage of the synthesis.

Compounds of formula ID can be converted into other compounds of formula ID before being used in the subsequent reactions. For example, compounds in which $R^1$ is hydrogen can be converted to compounds containing other $R^1$ groups by reacting with a carboxylic acid $R^1$—$CO_2H$, generally in solvents such as sulphuric acid and water, in the presence of a radical generating agent such as silver nitrate or ammonium persulfate, at about 70° C.

Compounds of formula ID wherein $L^1$ is chlorine can be prepared by chlorination of a compound of formula IF:

(IF)

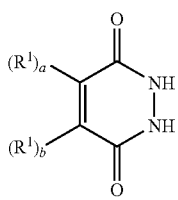

wherein a, b and $R^1$ are as defined above. Standard chlorination conditions can be used, such as the presence of a chlorination agent such as phosphorous oxychloride at about 120° C. in a microwave.

Compounds of formula IF can be prepared from substituted maleic anhydrides by ring opening with a hydrazine derivative, such as tert-butyl carbazate, generally in a solvent such as diethyl ether at about 0° C. to RT, followed by cyclisation to a compound of formula IF, for example by heating to 50° C. in acidic MeOH solution.

Alternatively, compounds of formula IA can be prepared by hydrolysis of a compound of formula IG.

(IG)

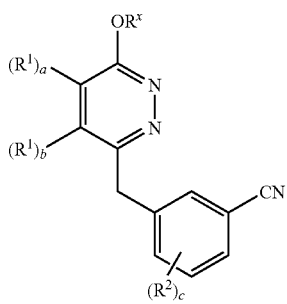

wherein a, b, c, $R^1$ and $R^2$ are as defined above and $R^x$ is $C_{1-6}$alkyl, for example methyl. Standard hydrolysis conditions can be used, such as the presence of an acid such as HCl, a solvent such as dioxane at about 120° C.

Compounds of formula IG can be prepared by coupling a compound of formula IH with a compound of formula IJ:

(IH)

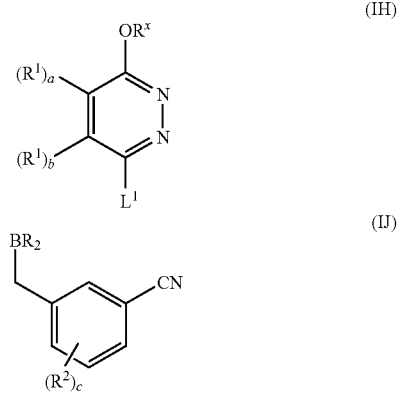

(IJ)

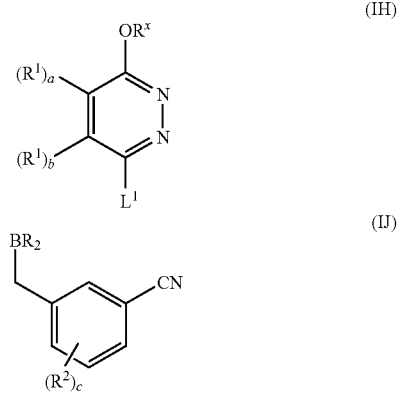

wherein a, b, c, $R^1$, $R^2$, $R^x$ and $L^1$ are as defined above and $BR_2$ is a boron derivative such as tetramethyldioxaborolanyl or boronic acid. The reaction is generally carried out under Suzuki coupling conditions such as in the presence of a palladium catalyst such as $Pd(OAc)_2$, a ligand such as dicyclohexyl(2',4',6'-triisopropylbiphenyl-2-yl)phosphine, a base such as $K_2CO_3$, in solvents such as THF and water at about 50 to 56° C.

Compounds of formula IH can be prepared by reacting a compound of formula ID with a compound of formula $NaOR^x$, generally in a solvent such as MeOH at about 0° C. to RT.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc protecting group is present, it may be removed by the addition of TFA in solvents such as DCM and/or MeCN at about room temperature. EtOAc in the presence of HCl and 1,4-dioxane may alternatively be used, at about room temperature. The benzylcarbonyl protecting group can be removed by hydrogenation using standard methods, such as treating with a catalyst such as Pd/C, in a solvent such as methanol under a hydrogen atmosphere.

The compounds of this invention were prepared according to the following schemes. All variables within the formulae are as defined above.

Scheme 1

Compounds described in this invention can be prepared using the methods described below. For instance, 3,6-dichloro-4-alkylpyridazine and 3,6-dichloro-4,5-dialkylpyridazines can be obtained by radical addition to the dichloropyridazine, the appropriate radicals are generated by decarboxylation of the appropriate alkanoic acid with ammonium peroxodisulfate in presence of Ag(I), as described in

*Org. Prep.+Proc. Int.* 1988, 20, 117. The reaction of the substituted 3,6-dichloropyridazine derivatives with the appropriate phenyl derivative bearing an activated methylene group, activated by an electron withdrawing group such as an ester or nitrile, in the presence of base allows displacement of the chlorine groups to give a mixture of the two regio isomeric 3-((benzyl)pyridazines. Hydrolysis of this isomeric mixture, with concurrent decarboxylation and hydrolysis of the imino chloride group, followed by coupling with the appropriate amine results in the formation of the desired inhibitor. The mixture of isomers may be separated at this stage or at previous steps in the synthetic sequence (Scheme 1).

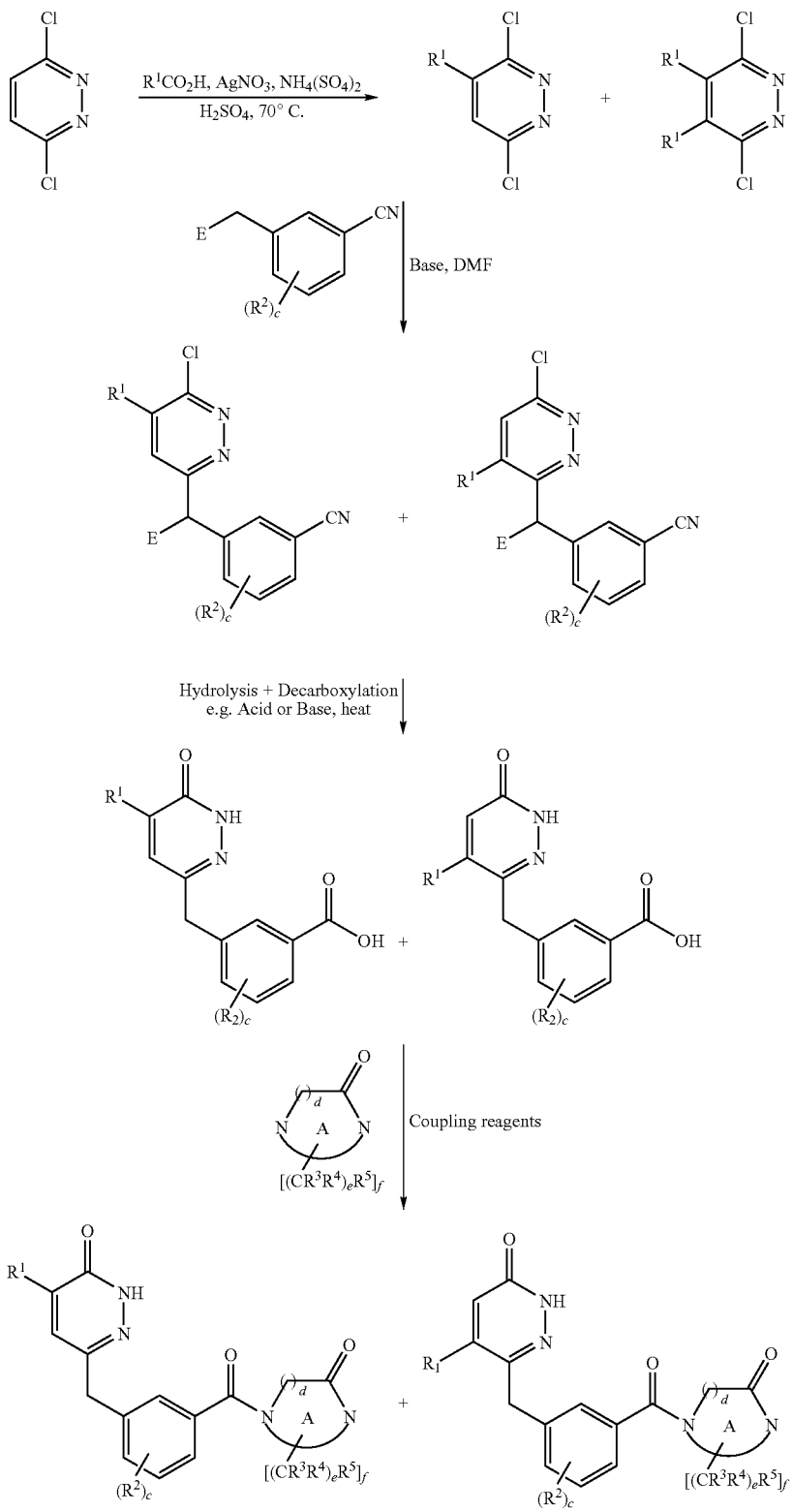

-continued

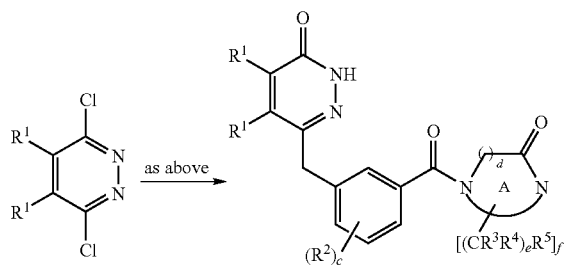

wherein:
E is an electron withdrawing group e.g.——CO$_2$Alkyl,——CN; R$^1$ is C$_{1-6}$alkyl or haloC$_{1-6}$alkyl; and all other variables are as defined above The inhibitors of the present invention can be transformed into other related derivatives by standard transformations known to those skilled in the art. For instance: coupling reactions of amino groups with: carboxylic acids using coupling reagents like HBTU, HATU, TBTU and PyBoP, or with activated acyl groups; sulfonylations reactions using sulfonyl chlorides; or reductive aminations using a carbonyl derivative and an amino group, using a reducing agent like sodium cyanoborohydride.

Scheme 2

Asymmetric 3,6-dichloro-4-alkyl-5-alkyl*-pyridazines can be formed by reacting 3,6-dichloro-4-alkylpyridazine with a second alkyl or haloalkyl radical by decarboxylation of the appropriate alkanoic acid with ammonium peroxodisulfate in presence of Ag(I), as described in *Org. Prep.+Proc. Int.* 1988, 20, 117. The reaction sequences as described above allow the elaboration of the desired PARP inhibitors (Scheme 2). As described previously the isomers can be separated as final compounds or as synthetic intermediates at any steps in the synthetic sequence.

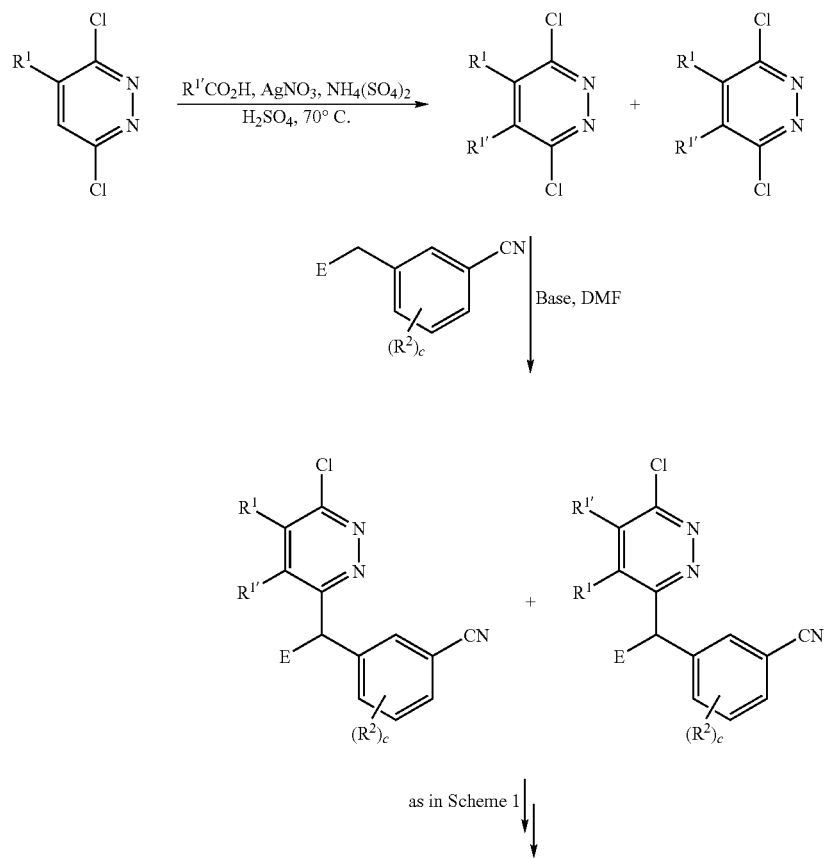

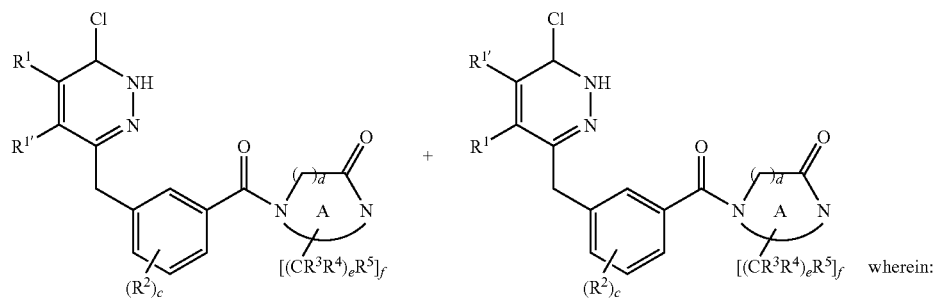

E is an electron withdrawing group e.g. —CO₂Alkyl, —CN;
R¹ is C₁₋₆alkyl; R¹' is C₁₋₆alkyl or haloC₁₋₆alkyl; and
all other variables are as defined above

Scheme 3

A method for the synthesis of compounds with different R² groups is to carry out a nucleophilic aromatic substitution reaction on the phenyl ring. For example, a halogen group, for instance a fluoride, on the phenyl ring can be displaced with an alkoxide ion or an amino group. Treatment with a sodium alkoxide in a refluxing alcohol solvent allows an alkoxy group to be introduced on the phenyl ring. Alternatively, vigorous heating of the substrate in a solution of the amine in a polar solvent like DMF, in a sealed reaction vessel, allows the formation of alkylamino and dialkylamino groups on the phenyl ring. Subsequent functional group manipulations such as the hydrolysis of nitrile groups in strong basic media at reflux and coupling, gives the desired PARP inhibitors (Scheme 3).

Scheme 3

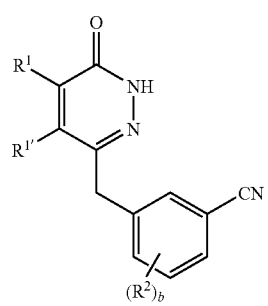

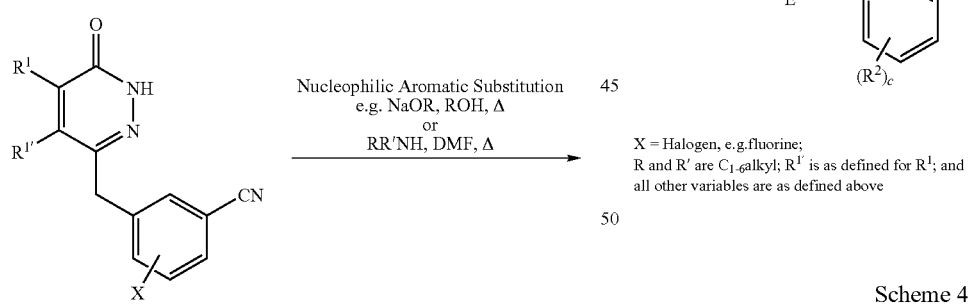

X = Halogen, e.g. fluorine;
R and R' are C₁₋₆alkyl; R¹' is as defined for R¹; and
all other variables are as defined above

Scheme 4

Alternatively, when the required substituted 3,6-dichloropyridazines are not available they can be readily prepared from the corresponding maleic anhydrides. For instance, an appropriately substituted maleic anhydride can be opened with tert-butyl carbazate at room temperature to give an isomeric mixture of hydrazides. These can be cyclised upon treatment with a mineral acid at 50° C. to give the pyridazinedione. Chlorination with phosphorous oxychloride with microwave irradiation yields the desired substituted dichloropyridazine which can be manipulated further as described above.

Scheme 4

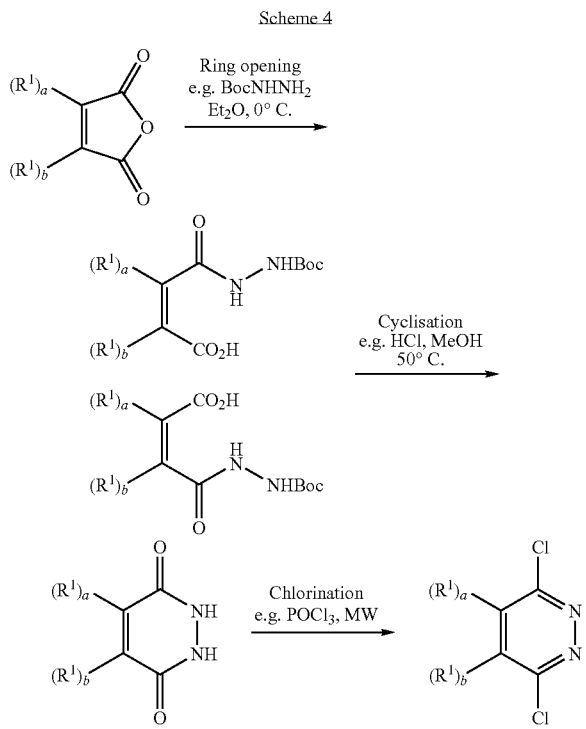

Scheme 5

Various procedures are described in the literature for preparing N-alkyl and N-aryl piperazinone and related derivatives. For instance, N-alkyl piperazinones can be prepared using a modification of the procedure reported in *Bioorg. Med. Chem.* 2007, 15, 2092-2105. For instance, methyl N-(tert-butoxycarbonyl)-N-(2-oxoethyl)glycinate can be treated with the appropriate amine or amine-HCl salt (plus base e.g. DIPEA) in MeOH and a reductive amination can be performed using $NaBH_3(CN)$ and AcOH. Irradiation with microwave accelerates ring closure to the desired piperazinone, which can in turn be deprotected, e.g. Using acidic conditions, TFA/DCM.

Similarly substituted piperazinones can be prepared as described in *Helv. Chim. Acta* 2000, 83, 1825 from the corresponding N-(2-oxoalkyl)glycinate derivatives, by firstly conducting a reductive amination reaction, and then cyclising to the desired substituted piperazines ring with a coupling reaction, for instance using HATU in the presence of DIPEA with microwave irradiation. With unreactive amines/anilines it may be necessary to use more forcing conditions for the reductive amination, such as condensation of the amine and carbonyl groups in the presence of $Ti(O^iPr)_4$, and subsequently reduction with $NaBH_3(CN)$.

Similar chemistry can also be performed on the fully formed scaffold, whereby methyl N-(2,2-diethoxyethyl)glycinate (described in *Synthesis* 2002, 2, 242-252) or a related species can be coupled to the required scaffold. Upon hydrolysis of the ester functionality, e.g. using LiOH, and subsequent acid hydrolysis of the carbonyl protecting group, for instance with TFA in $CHCl_3/H_2O$, an advanced intermediate is obtained. Reductive amination and lactamisation, then yields the desired final compounds.

Scheme 5

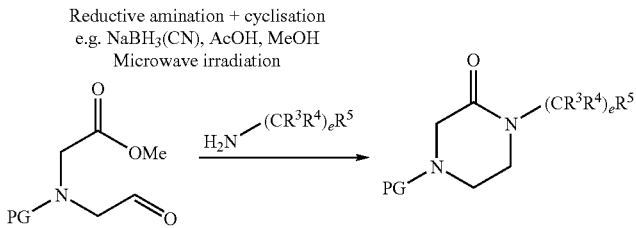

PG = protecting group, e.g. Boc

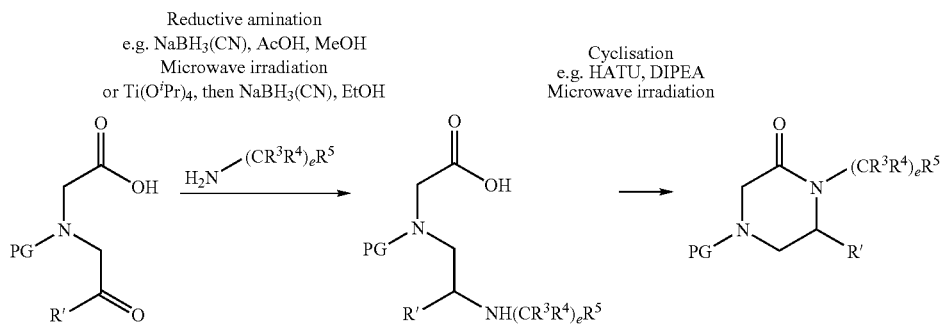

PG = protecting group, e.g. Boc
R' = -$(CR^3R^4)_eR^5$

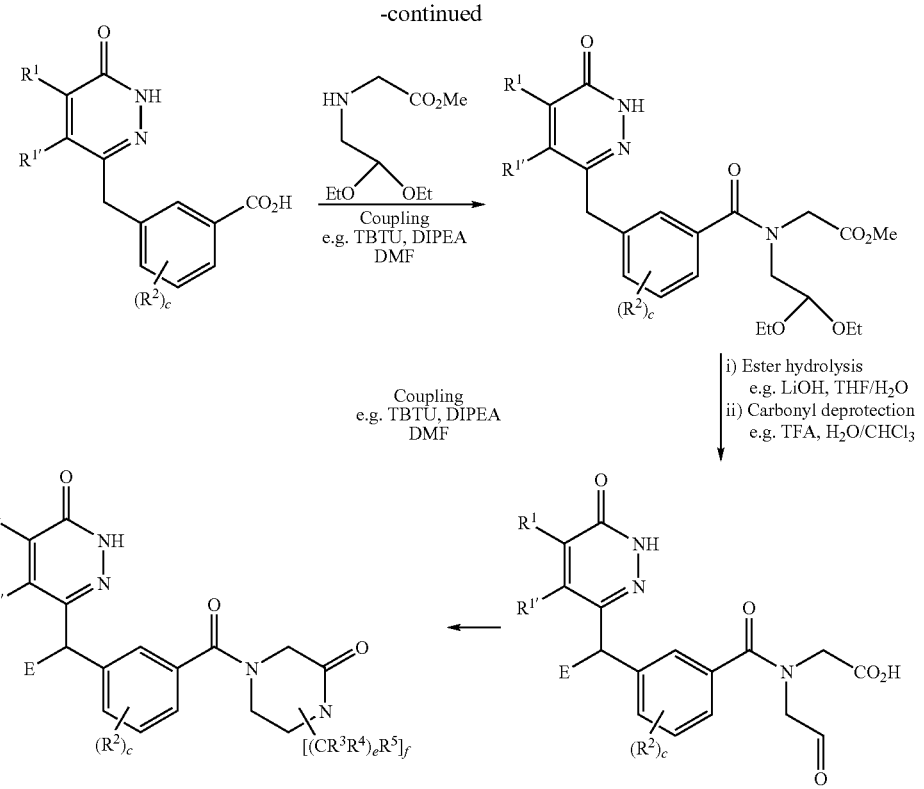

wherein:
X = Halogen, e.g. fluorine;
R and R' are C$_{1-6}$alkyl; R$^{1'}$ is as defined for R$^1$; and
all other variables are as defined above Scheme 6

Alternatively, N-aryl and N-heteroaryl derivatives can be prepared from the protected piperazinone using methods described in *J. Am. Chem. Soc.* 2002, 124, 7421 using copper catalysis, for instance using CuI, K$_3$PO$_4$ and N,N'-dimethylethylendiamine in 1,4-Dioxane with either thermal or microwave heating. Alternatively, a similar coupling can be performed using palladium catalysis as described in *J. Am. Chem. Soc.* 2002, 124, 6043-6048 using Pd(OAc)$_2$, Xantphos and Cs$_2$CO$_3$ in 1,4-Dioxane at 110° C.

A related protocol, allows the alkylation of the lactam derivatives by cross-coupling with the corresponding boronic acid, using copper (II) acetate in the presence of organic bases such pyridine and triethylamine with microwave heating at 140° C.

Scheme 6

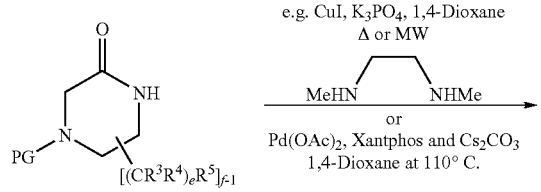

N-Arylation or Heteroarylation
R$_5$—X
e.g. CuI, K$_3$PO$_4$, 1,4-Dioxane
Δ or MW
MeHN NHMe
or
Pd(OAc)$_2$, Xantphos and Cs$_2$CO$_3$
1,4-Dioxane at 110° C.

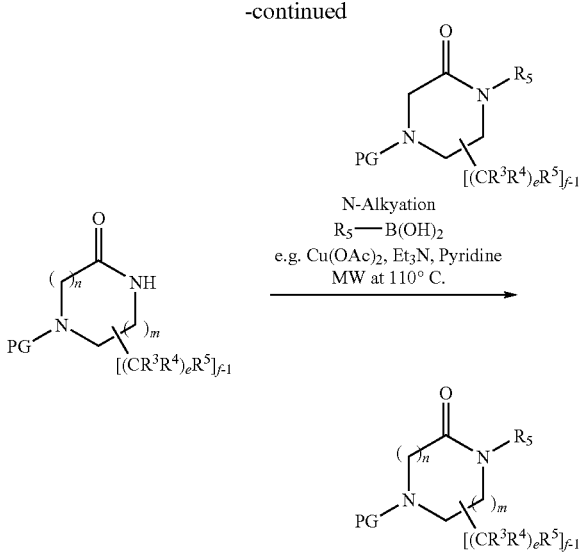

PG = protecting group, e.g Boc;
X = Cl, Br or I;
R$^5$ is an unsaturated ring
n = 1 or 2
m = 0, 1 or 2

Scheme 7

Preparation of More Highly Substituted Derivatives can be Performed Either by Elaboration of the preformed piperazinone, homopiperazinone and related ring systems or they can be synthesized by alternative routes. For instance, alkylation adjacent to the lactam carbonyl group can be achieved by deprotonation with a strong base, like LiHMDS, followed by quenching on an electrophile, such as methyl iodide.

Whilst another preparative procedure, which also allows for groups to be introduced adjacent to the carbonyl involves the cyclisation of more elaborated derivative. Monoprotected diamines can readily be prepared by a reductive amination and the unprotected amino group can be acylated with α-halo acyl halides. After removal of the protecting group from the other nitrogen atom, the resulting compounds can be cyclised to the desired lactam upon treatment with a base, such as using potassium carbonate in an alcohol solvent. Alternative the compounds can be cyclised prior to deprotection using NaH in DMF, followed by deprotection.

Alternatively, monoprotected substituted diamines can be prepared, for instance by reduction of amino-amides with LiAlH$_4$, followed by selective protection of the less sterically crowded amino group. Acetylation with a haloacetyl halide, such as chloroacetyl chloride, followed by basic cyclisation, for instance using NaH in DMF, gives the desired lactam derivatives. These in turn can be deprotected and coupled to the scaffold to yield the required inhibitors.

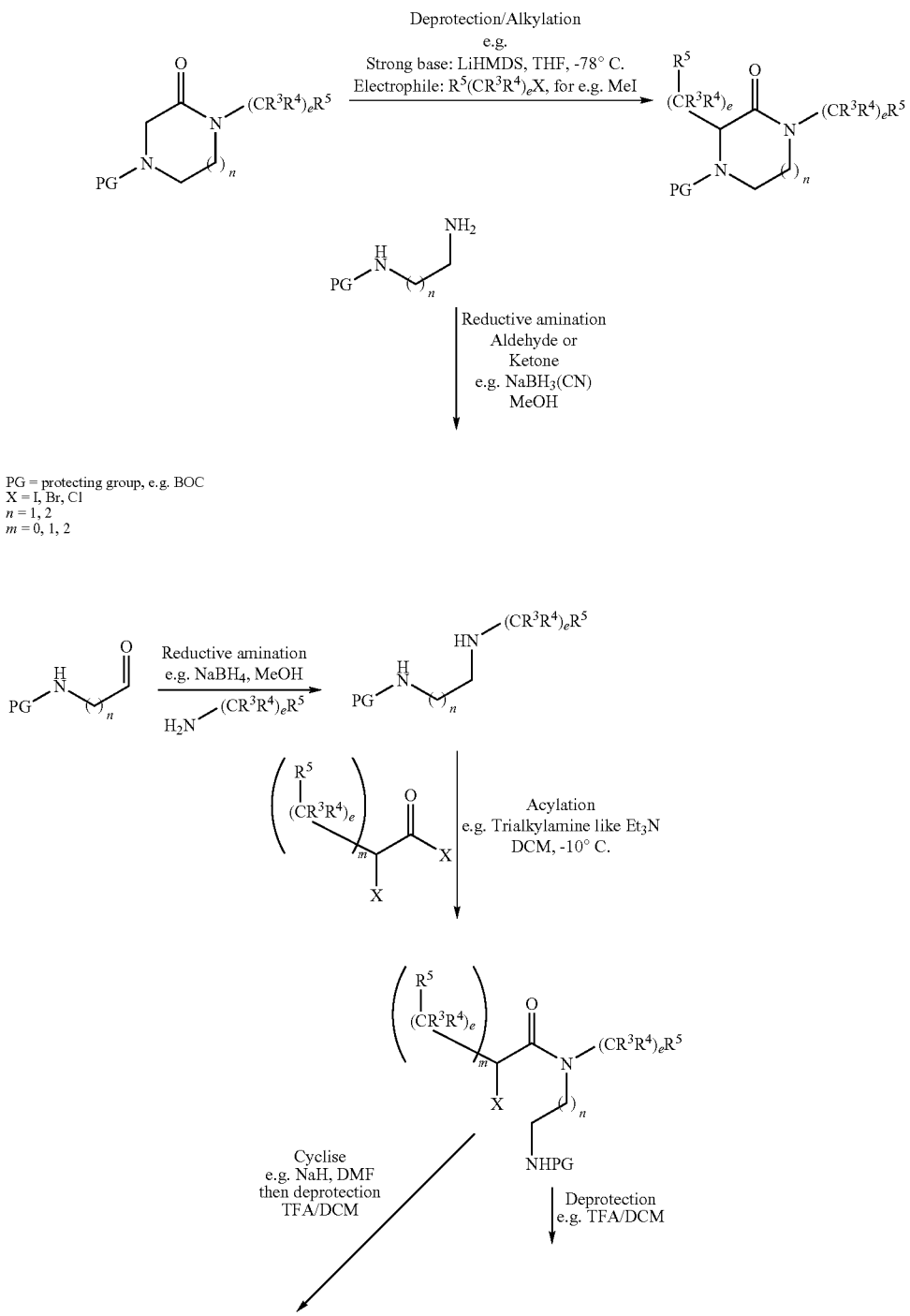

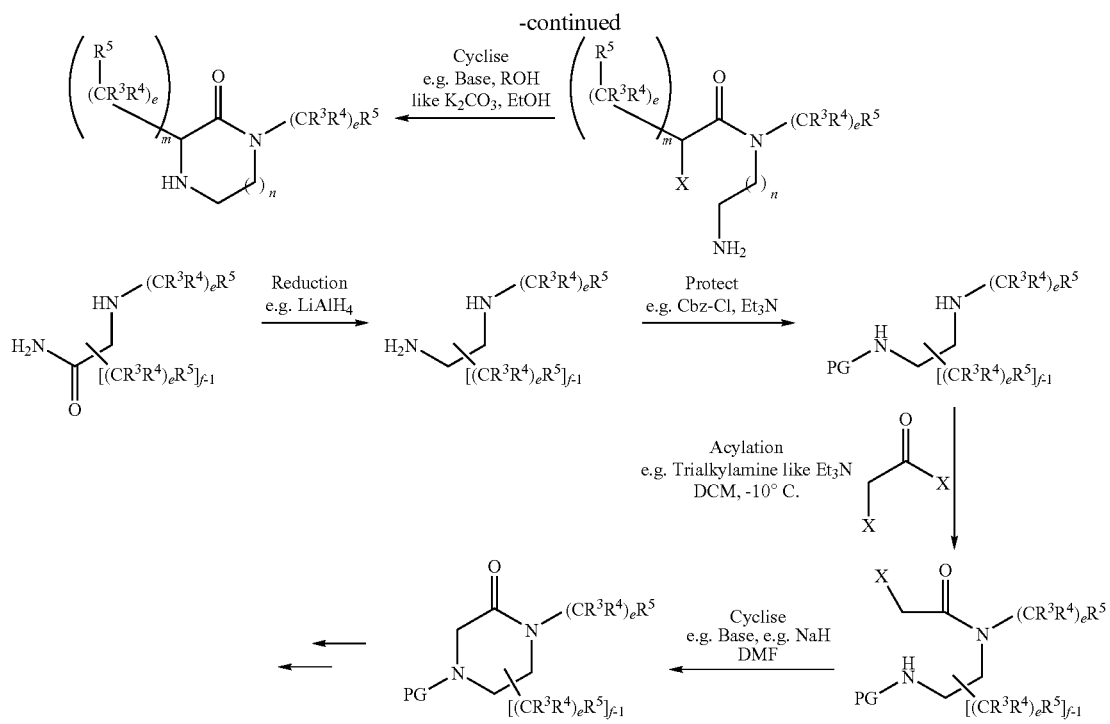

PG = protecting group, e.g. Boc or Cbz
X = I, Br or Cl
f = 1, 2, 3 or 4

Scheme 8

Similar procedures can be utilized with cyclic diamines, enabling bicyclic lactams to be synthesized. For instance, reaction of a piperidine, homopiperidine or morpholine derivative bearing a protected pendant aminomethylene group allows the internal secondary amine to be acylated with a haloacetyl halide. Deprotection of the secondary amine, and alkylation gives the required bicyclic lactam, ready for coupling to the scaffold.

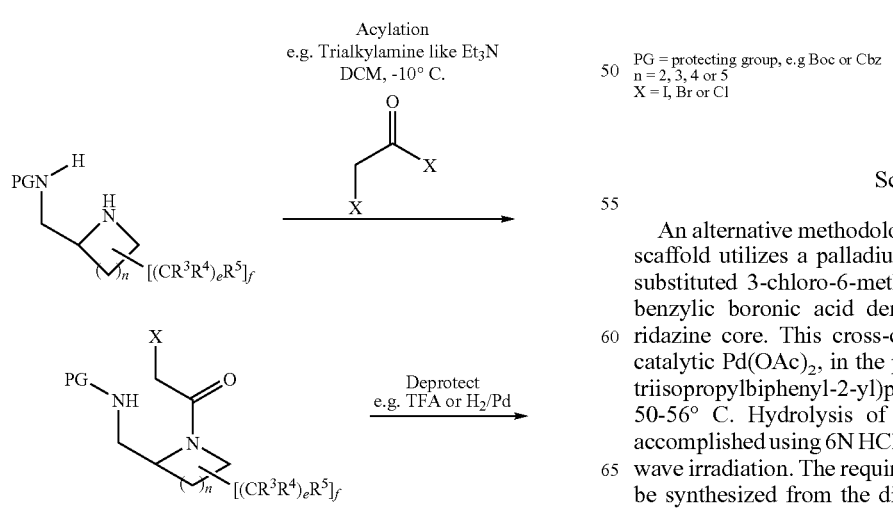

PG = protecting group, e.g Boc or Cbz
n = 2, 3, 4 or 5
X = I, Br or Cl

Scheme 9

An alternative methodology to synthesize the desired core scaffold utilizes a palladium catalyzed cross coupling of a substituted 3-chloro-6-methoxypyridazine derivative and a benzylic boronic acid derivative, to yield the benzylpyridazine core. This cross-coupling is carried out utilizing catalytic $Pd(OAc)_2$, in the presence of dicyclohexyl(2',4',6'-triisopropylbiphenyl-2-yl)phosphine and $K_2CO_3$ as base at 50-56° C. Hydrolysis of the methoxypyridazine can be accomplished using 6N HCl in dioxane at 120° C. with microwave irradiation. The required chloromethoxypyridazine can be synthesized from the dichloropyridazine by simple displacement with sodium methoxide.

Scheme 9

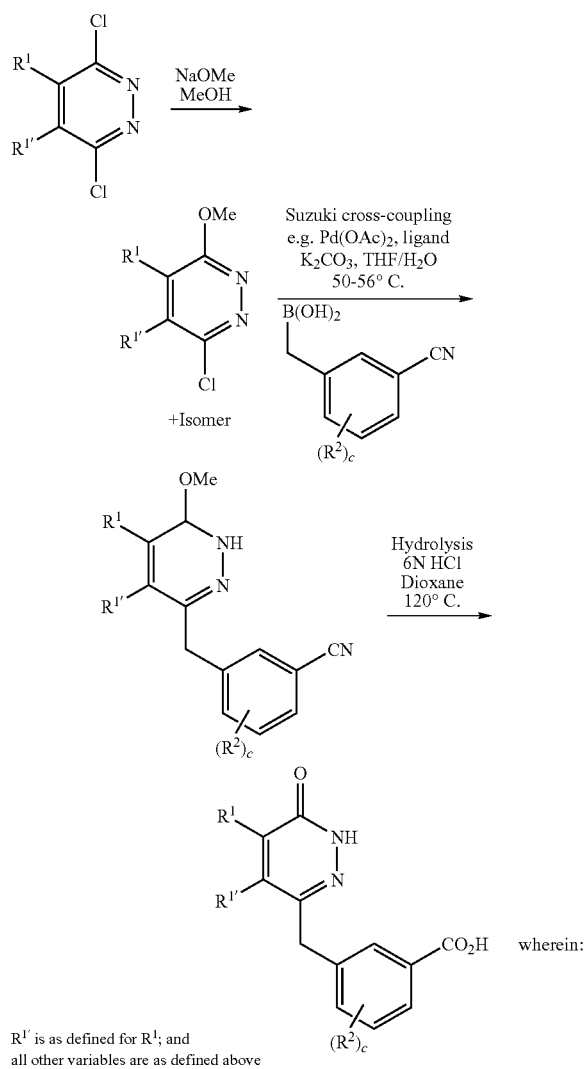

wherein:
$R^{1'}$ is as defined for $R^1$; and
all other variables are as defined above The exemplified compounds described herein were tested by the assays described below and were found to have an $IC_{50}$ value of less than 500 nM, particularly less than 200 nM.

PARP-1 Spa Assay
Working Reagents
Assay buffer: 100 mM Tris pH 8, 4 mM $MgCl_2$, 4 mM Spermine, 200 mM KCl, 0.04% Nonidet P-40.
Enzyme Mix: Assay buffer (12.5 ul), 100 mM DTT (0.5 ul), PARP-1 (5 nM, Trevigen 4668-500-01), $H_2O$ (to 35 ul).
Nicotinamide-adenine dinucleotide (NAD)/DNA Mix: [$^3$H-NAD] (250 uCi/ml, 0.4 ul, Perkin-Elmer NET-443H), NAD (1.5 mM, 0.05 ul, SIGMA N-1511), Biotinylated-NAD (250 uM, 0.03 ul, Trevigen 4670-500-01), Activated calf thymus (1 mg/ml, 0.05 ul, Amersham Biosciences 27-4575), $H_2O$ (to 10 ul).
Developing Mix: Streptavidin SPA beads (5 mg/ml, Amersham Biosciences RPNQ 0007) dissolved in 500 mM EDTA.
Experimental Design
The reaction is performed in 96-well microplate with a final volume of 50 uL/well. Add 5 ul 5% DMSO/compound solution, add enzyme mix (35 ul), start the reaction by adding NAD/DNA mix (10 uL) and incubate for 2 hrs at RT. Stop the reaction by adding developing mix (25 ul) and incubate 15 min at RT. Measure using a Packard TOP COUNT instrument.
The Examples of the present application were tested in the above assay and found to have the following biological activities.
Examples 1-6, 8-23, 25-30, 33, 38, 39, 42-47, 49, 54, 59, 60, 62-66, 68-71, 73, 74, 76, 77, 78 (LL4 and LL4B), 79, 80, 83-86, 88, 90, 92 (ZZ1), 94, 95, 98-112, 116-119, 121-123, 126-132, 136, 142, 144, 148, 150, 153-155, 161-169, 171, 173-175, 177-180, 182-184, 186-206 and 208-211 showed $IC_{50}$ values of less than 5 nM. Examples 7, 24, 31, 32, 34-36, 40, 48, 50-53, 55-58, 61, 67, 72, 78 (LL4A), 81, 87, 91, 92 (ZZ2), 96, 97, 113-115, 120, 124, 125, 133-135, 137-141, 143, 145-147, 149, 151, 152, 170, 172, 176, 181, 207 and 212 showed $IC_{50}$ values of between 5-25 nM. Examples 37, 41, 82, 93 and 185 showed $IC_{50}$ values of between 25-150 nM.

Comparative Data

The following Table 1 compares the biological activities of compounds of the present application with the compounds of International Patent Application PCT/GB07/050,295. The presence of a carbonyl group on the piperazine ring (when A is piperazine in formula I) significantly improved the $IC_{50}$ value in the PARP-1 TCA assay and the $CC_{50}$ values in the BRCA-1 silenced assay. These assays are described below.

TABLE 1

Enzyme and cellular data for N-substituted piperazinones, N-substituted piperazines and 4- substituted-tetrahydropyridines

| Compound | PARP-1 TCA $IC_{50}$ (nM) | BRCA1- $CC_{50}$ (nM) |
|---|---|---|
|  | 1.0 | 18 |

TABLE 1-continued
Enzyme and cellular data for N-substituted piperazinones, N-substituted piperazines and 4- substituted-tetrahydropyridines
| Compound | PARP-1 TCA IC$_{50}$ (nM) | BRCA1- CC$_{50}$ (nM) |
|---|---|---|
| 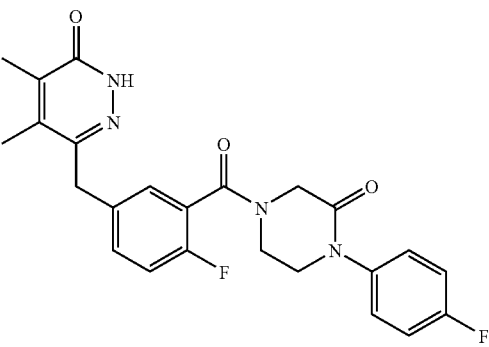 | 0.87 | 96 |
| 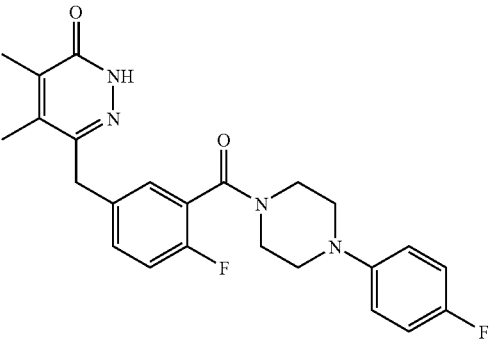 | 20 | 52% inh @ 5 uM |
| 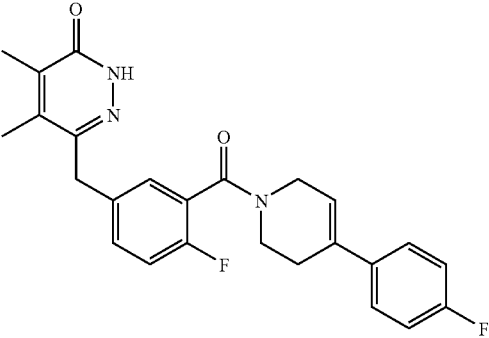 | 20 | 45% inh @ 5 uM |
| 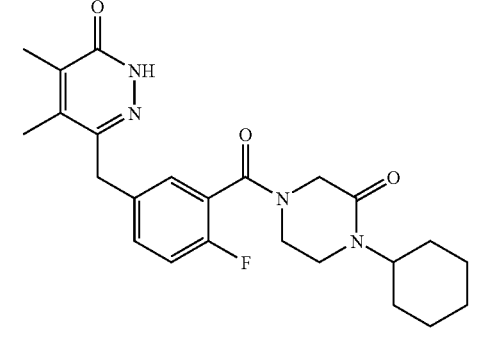 | 0.36 | 7 |

TABLE 1-continued

Enzyme and cellular data for N-substituted piperazinones, N-substituted piperazines and 4-substituted-tetrahydropyridines

| Compound | PARP-1 TCA IC$_{50}$ (nM) | BRCA1- CC$_{50}$ (nM) |
|---|---|---|
| 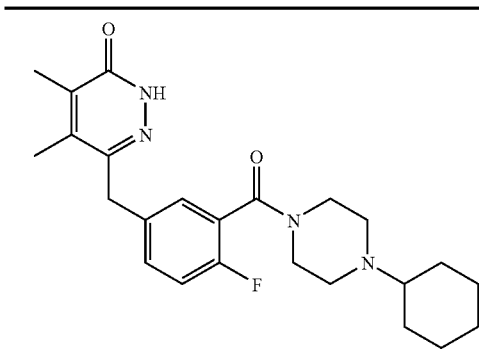 | 7.4 | 400 |

PARP-1 TCA Assay

Inhibitory Activity on Human PARP-1

Rationale

The study was designed to determine the potency of compounds for inhibiting poly(ADP-ribosylation) by hPARP1 upon presentation of a nicked DNA (i.e. Activated Calf Thymus). The IC$_{50}$ was determined in a TCA assay looking at the incorporation of [$^3$H]-NAD into the growing Poly-ADP-ribose (PAR) polymers and detection of the radioactivity incorporated in a polymer by scintillation counting.

Material and Methods

A 96 wells polypropylene microplate was prepared with serial dilutions of compounds (10 point over a 0.1 nM-50 nM concentration range 5% DMSO, 5 uL) or 5% DMSO. The enzymatic reaction was conducted in the presence of 25 mM Tris-HCl pH8.0, 1 mM MgCl$_2$, 50 mM KCl, 1 mM Spermine, 0.01% Nonidet P-40, 1 mM DTT, 1 ug/ml activated Calf Thymus DNA (Amersham Biosciences 27-4575) and 1 nM of human PARP-1 enzyme (Trevigen 4668-500-01). The reaction was initiated by adding 1 ug/ml Activated Calf Thymus DNA (Amersham Biosciences 27-4575), 0.4 ul (2.2×10$^5$DPM) of [$^3$H]-NAD (250uCi/ml, Perkin Elmer NET-443H) and 1.5 uM NAD (Sigma #N-1511) in a total reaction volume of 50 ul. After 2 hours incubation at room temperature, the reaction was stopped by the addition of TCA (50 uL, 20%) and NaPPi (20 mM) and incubated for 10 min over ice. The resulting precipitate was filtered on Unifilter GF/B microplate (Perkin Elmer) and washed four times with 2.5% TCA using Harvester Filtermate 196 (Perkin Elmer). After addition of 50 ul of Microscint 20 (Perkin Elmer) the amount of radioactivity incorporated into the PARP polymers was read for each well on Perkin Elmer Top Count. IC$_{50}$ was calculated using 4P logistic fitting with ADA software based on the residual enzyme activity in the presence of increasing concentrations of compounds.

Proliferation Assay in BRCA-1 Silenced HeLa Cells

Abbreviations:

IMDM (Iscove's Modified Dulbecco's Media); RPMI (Roswell Park Memorial Institute Media); MOI (multiplicity of infection); GFP (green fluorescent protein); PBS (Phosphate Buffered Saline); FCS (fetal calf serum); and DMEM (Dulbecco's Modified Eagle's Medium).

Compounds of the present invention were also tested in an anti-proliferative assay in matched pair BRCA1 wt and BRCA1-(shRNA) HeLa cells. The assay shows that PARP inhibitors are able to show selectivity with growth inhibition of the BRCA deficient cells. The majority of compounds showed CC$_{50}$'s less than 5 μM in BRCA1 deficient cells and a greater than 50 fold selectivity over the BRCA proficient cells. Some compounds showed CC$_{50}$ values in BRCA1 deficient cells of less than 1 μM.

The assay is based on the ability of living cells to convert a redox dye (resazurin) into a fluorescent end product (resofurin). The amount of resofurin produced is directly proportional to the cell number.

Cell Lines:

HeLa shBRCA1-GFP—These are HeLa cells transduced at an MOI of 100 with a Lentivirus containing a shRNA against BRCA-1 and an expression cassette for GFP. BRCA-1 silencing is more than 80% as assessed by Taqman analysis and the cells stably express GFP.

HeLa THM-GFP—These are HeLa cells transduced at an MOI of 100 with a control vector not expressing any shRNA.

Protocol

Seed 300 cell/well in 96 wells viewplate black in 90 ul culture Medium*:

Incubate 4 hours at 37° C., 5% CO$_2$

Add 10 ul/well of 10× compound (5% DMSO in H$_2$O)

Incubate for 168 hours at 37° C., 5% CO$_2$

Add 10 ul of Celltiter Blue solution (Promega, G8081) pre-diluted 1:1 in PBS1×

Incubate the mixture for 45' at 37° C., 5% CO$_2$

Incubate 15' at RT in the dark

Read plate at fluorimeter ex: 550 nm; em: 590 nm

*Culture Medium: DMEM (GIBCO, 41966-029), 10% FCS (GIBCO, 10106-169), 0.1 mg/ml Penicillin-Streptomycin (GIBCO, 15140-114), 2 mM L-Glutamine (GIBCO, 3042190)

Specific CC$_{50}$ values in the BRCA1 silenced HeLa cells demonstrated by particular Examples are provided below.

Examples 1-4, 9-13, 15, 25-26, 29, 30, 32, 39, 42-44, 46, 49, 50, 60, 63, 68, 70, 73, 75 (II4B), 77, 78 (LL4 and LL4B), 79, 83, 85, 86 (TT1), 87, 88 (VV1), 90, 98-102, 104, 105, 108, 114, 119, 125-128, 131, 132, 135, 140-143, 146-147, 151, 155, 156, 159, 161-163, 165-168, 174, 175, 177, 178, 187-191, 193-203, 205, 206, 208 and 209 showed CC$_{50}$ values of less than 50 nM. Examples 5, 6, 14, 16-23, 27, 28, 33, 38, 40, 47, 48, 51-55, 57, 59, 61, 62, 65-67, 69, 71, 72, 74, 75 (II4A), 78 (LL4A), 80, 81, 86 (TT2), 88 (VV2), 91, 92 (ZZ2), 94, 95, 103, 106, 107, 113, 117, 118, 121-124, 129-130, 133, 136-139, 145, 148-150, 153, 157, 158, 160, 164, 184, 192 and 204 showed $CC_{50}$ values of between 50-500 nM. Examples 8, 31, 35, 36, 45, 56, 64, 76, 89, 92 (ZZ1), 96, 97, 109, 110, 112, 115, 120, 134, 144, 152, 154, 169-173, 176, 179, 180, 181, 185, 186 and 207 showed $CC_{50}$ values of less than 5 uM.

PREPARATIVE EXAMPLE 1

4-{5-[(5-Ethyl-6-oxo-1,6-dihydropyridazin-3-yl)methyl]-2-fluorobenzoyl}-1,4-diazepan-1-ium trifluoroacetate (A4)

Step 1: 5-[(6-chloro-5-ethylpyridazin-3-yl)(cyano)methyl]-2-fluorobenzonitrile (A1) and 5-[(6-chloro-4-ethylpyridazin-3-yl)(cyano)methyl]-2-fluorobenzonitrile (A2)

To an ice-cold solution of 5-(cyanomethyl)-2-fluorobenzonitrile (1 eq) and 3,6-dichloro-4-ethylpyridazine (1.9 eq) (Reference: *Org. Prep.+Proc. Int.* 1988, 20, 117 and U.S. Pat. No. 4,628,088, 1986) in DMF was added portionwise NaH (2.1 eq). The reaction was stirred at 0° C. for 15 min and then warmed to RT and stirred for 2 hrs. The reaction was quenched with a sat. aq. $NaHCO_3$ and extracted with EtOAc. The combined organic fractions were washed with brine, dried ($Na_2SO_4$) and concentrated under reduced pressure. An isomeric mixture of 4- and 5-ethylpyridazine was separated by silica gel chromatography, eluting with 9:1 Hexanes:EtOAc to afford first the 5-substituted isomer (A1) and subsequently the 4-substituted isomer (A2).

5-[(6-chloro-5-ethylpyridazin-3-yl)(cyano)methyl]-2-fluorobenzonitrile (A1): $^1H$ NMR (300 MHz, $CDCl_3$) δ: 7.80-7.78 (2H, m), 7.48 (1H, s), 7.31-7.29 (1H, m), 5.63 (1H, s), 2.81 (2H, qd, J=7.6 and 3.1 Hz), 1.31 (3H, t, J=7.6 Hz). MS (ES) $C_{15}H_{10}ClFN_4$ requires: 300/302, found: 301/303 $(M+H)^+$.

5-[(6-chloro-4-ethylpyridazin-3-yl)(cyano)methyl]-2-fluorobenzonitrile (A2): $^1H$ NMR (400 MHz, $CDCl_3$) δ: 7.75-7.67 (2H, m), 7.45 (1H, s), 7.30 (1H, t, J=8.6 Hz), 5.74 (1H, s), 2.80-2.70 (1H, m), 2.60-2.50 (1H, m), 1.26 (3H, t, J=7.3 Hz). MS (ES) $C_{15}H_{10}ClFN_4$ required: 300/302, found: 301/303 (M+H)+.

Step 2: 5-[(5-ethyl-6-oxo-1,6-dihydropyridazin-3-yl)methyl]-2-fluorobenzoic acid (A3)

A mixture of A1 (1 eq) in AcOH, conc. HCl and $H_2O$ (1:2:1, 0.065 M) was heated at reflux overnight, then cooled to RT and diluted with $H_2O$ and EtOAc and separated. The aqueous phase was washed with EtOAc and the combined extracts were washed with brine, dried ($Na_2SO_4$), and concentrated under reduced pressure. The crude was dissolved in AcOH and NaOAc (2 eq) was added. The resulting solution was heated at reflux for 1 hr. The reaction mixture was cooled and the mixture was extracted with EtOAc. The organic phase was washed twice with brine, dried ($Na_2SO_4$) and the solvent removed under reduced pressure. The residue was taken up in $H_2O$ and to the resulting suspension was added an aqueous solution of 23 M NaOH (8 eq) and heated to 90° C. for 30 min. The reaction solution was cooled then acidified to pH 4 with 2 M HCl. The mixture stirred for 10 min and filtered. The resulting solid was washed sequentially with $H_2O$, hexanes, $Et_2O$, EtOAc and dried under high vacuum to give the title compound as a pale orange powder.

$^1H$ NMR (300 MHz, DMSO-d6) δ: 13.30 (0.5H, br. s), 12.74 (1H, s), 7.78-7.75 (1H, m), 7.53 (1H, m), 7.31-7.25 (1H, m), 7.72 (1H, s), 3.94 (2H, s), 2.45 (2H, J=7.5 Hz), 1.11 (3H, t, J=7.5 Hz). MS (ES) $C_{14}H_{13}FN_2O_3$ required: 276, found: 277 $(M+H)^+$.

Step 3: 4-{5-[(5-Ethyl-6-oxo-1,6-dihydropyridazin-3-yl)methyl]-2-fluorobenzoyl}-1,4-diazepan-1-ium trifluoroacetate (A4)

To a solution of A3 (1 eq) in DMA was added HBTU (2 eq), tert-butyl 1-homo-piperazinecarboxylate (1.9 eq), and DIPEA (3.4 eq). The mixture was stirred overnight at RT and then the reaction mixture was concentrated, the crude was dissolved in DCM, and washed twice with $H_2O$, dried ($Na_2SO_4$) and concentrated under reduced pressure. The resulting orange oil was dissolved in a mixture of 6 M HCl/EtOH (2:1) and the mixture stirred at RT for 1 h. The solution was concentrated, basified with conc. $NH_3$ aq. solution to pH 9, and then the organics were extracted with DCM. The combined organic fractions were washed with $H_2O$, brine, dried ($Na_2SO_4$) and the solvent removed under reduced pressure. The residue was purified by preparative RP-HPLC, using $H_2O$ (0.1% TFA) and MeCN (0.1% TFA) as eluents (column: Water X-Terra C18) and the pooled product fractions were lyophilized to give the title compound as a colourless powder. $^1H$ NMR (300 MHz, DMSO-d6) δ: 12.76 (1H, s), 8.79 (2H, br. s), 7.45-7.27 (3H, m), 7.19 (1H, s), 3.93 (2H, s), 3.85-3.74 (2H, m), 3.56 (1H, m), 3.39-3.20 (5H, m), 2.45 (2H, J=7.5 Hz), 2.08-1.91 (2H, m), 1.11 (3H, t, J=7.5 Hz). MS (ES) $C_{19}H_{23}FN_4O_2$ required: 358, found: 359 $(M+H)^+$.

PREPARATIVE EXAMPLE 2

5-[(4,5-Dimethyl-6-oxo-1,6-dihydropyridazin-3-yl)methyl]-2-fluorobenzoic acid (B4)

Step 1: 5-[(6-Chloro-4,5-dimethylpyridazin-3-yl)(cyano)methyl]-2-fluorobenzonitrile (B1)

The procedure followed the one described in Preparative Example 1 step 1, starting from 3,6-dichloro-4,5-dimethylpyridazinone (prepared according *J. Org. Chem.* 1955, 20, 707-13). $^1H$ NMR (300 MHz, DMSO-$d_6$) δ: 8.05-7.96 (1H, m), 7.95-7.82 (1H, m), 7.70-7.61 (1H, m), 6.48 (1H, s), 2.41 (3H, s), 2.29 (3H, s). MS (ES) $C_{15}H_{10}ClFN_4$ required: 300, found: 301 $(M+H)^+$.

Step 2: 5-[(6-Chloro-4,5-dimethylpyridazin-3-yl)methyl]-2-fluorobenzonitrile (B2)

Intermediate B1 was suspended in a mixture of acetic acid, conc. aq. HCl and water (1:1:2, 0.07M). The suspension was stirred and heated at reflux for 75 min. The reaction mixture was cooled to RT and the solvents were removed under reduced pressure. To the residue was added saturated aq. $NaHCO_3$ and the mixture was extracted with EtOAc. The organic phase was dried ($Na_2SO_4$), filtered and concentrated to dryness. The residue was purified by column chromatography on silica gel, eluting with PE-EtOAc (10-80% EtOAc) to afford the title compound as a yellow solid. MS (ES) $C_{14}H_{11}ClFN_3$ required: 275, found: 276 $(M+H)^+$.

Step 3: 5-[(4,5-Dimethyl-6-oxo-1,6-dihydropyridazin-3-yl)methyl]-2-fluorobenzonitrile (B3)

To a solution of intermediate B2 in acetic acid (0.16 M) was added NaOAc (2 eq.) and the mixture was stirred and heated to reflux for 1 h. The solution was cooled to RT and the solvent was removed under reduced pressure. The residue was suspended in water and triturated until a fine suspension was obtained. The solid material was filtered off, washed with water, dried by air stream and then under high vacuum. MS (ES) $C_{14}H_{12}FN_3O$ required: 257, found: 258 (M+H)$^+$.

Step 4: 5-[(4,5-Dimethyl-6-oxo-1,6-dihydropyridazin-3-yl)methyl]-2-fluorobenzoic acid (B4)

To a suspension of intermediate B3 in water (0.35 M) was added NaOH (8 eq.) and the resulting mixture was stirred and heated to 100° C. for 60 min. The mixture was cooled with an ice bath and slowly acidified to pH 2-3 with 6N HCl. The formed light yellow precipitate was filtered off, dried under air stream and then under high vacuum. MS (ES) $C_{14}H_{13}FN_2O_3$ required: 276, found: 277 (M+H)$^+$.

PREPARATIVE EXAMPLE 3

2-Fluoro-5-{[6-oxo-5-(trifluoromethyl)-1,6-dihydropyridazin-3-yl]methyl}-benzoic acid (C7) and
2-Fluoro-5-{[6-oxo-4-(trifluoromethyl)-1,6-dihydropyridazin-3-yl]methyl}benzoic acid (C8)

Step 1: (2E)-3-{[2-(tert-Butoxycarbonyl)hydrazino]carbonyl}-4,4,4-trifluorobut-2-enoic acid (C1) and
(2E)-4-[2-(tert-Butoxycarbonyl)hydrazino]-4-oxo-2-(trifluoromethyl)but-2-enoic acid (C2)

To a stirred solution of trifluoromethylmaleic anhydride (1.0 eq) in Et$_2$O (0.32 M) cooled to 0° C. a solution of tert-butyl carbazate (1.0 eq) in Et$_2$O (0.32 M) charged in a dropping funnel was slowly added and then the reaction mixture was then stirred at RT for 1 h during which time a white precipitate was formed. After completion of the reaction, solvent was evaporated under reduced pressure affording the mixture of C1+C2 as a white solid which was used in the next step without further purification (quantitative yield). The two isomers were obtained in a ratio of 9:1 based on the NMR analysis. $^1$H NMR (300 MHz, DMSO-d6, 300K) δ 14.0 (1H, bs, OH both isomers), 10.22 (1H, bs, NH, major isomer), 9.67 (1H, bs, NH, minor isomer), 9.08 (1H, bs, NH, major isomer), 8.38 (1H, bs, NH, minor isomer), 6.95 (1H, s, CH, minor isomer), 6.77 (1H, s, CH, major isomer), 1.40 (9H, s, C(CH$_3$)$_3$, both isomer). MS (ES) $C_{10}H_{13}F_3N_2O_5$ requires: 298, found: 299 (M+H)$^+$.

Step 2: 4-(Trifluoromethyl)-1,2-dihydropyridazine-3,6-dione (C3)

A solution of intermediates C1 and C2 (1.0 eq.) in 1.25 M HCl/MeOH solution (4.0 eq.) was stirred for 2 hr at 50° C. After completion of the reaction, solvent was evaporated under reduced pressure and the crude material was crystallized from water. The desired C3 was obtained as a pale yellow crystalline solid (44% yield). $^1$H-NMR (400 MHz, DMSO-d6, 300K) δ 12.58 (1H, bs), 11.44 (1H, bs), 7.51 (1H, bs). MS (ES) $C_5H_3F_3N_2O_2$ requires: 180, found: 181 (M+H)$^+$.

Step 3: 3,6-Dichloro-4-(trifluoromethyl)pyridazine (C4)

A solution of intermediate C3 (1.0 eq) in phosphorus oxychloride (22.0 eq) was stirred for 90 min at 120° C. under MW irradiation. After completion of the reaction, solvent was evaporated under reduced pressure and the crude material was purified by flash column chromatography on silica gel using 2-10% Et$_2$O/Petroleum ether, the desired C4 was obtained as a white solid (76% yield). $^1$H-NMR (400 MHz, CDCl$_3$, 300K) δ 7.79 (1H, s).

Step 4: 5-[[6-Chloro-5-(trifluoromethyl)pyridazin-3-yl](cyano)methyl]-2-fluoro-benzonitrile (C5) and
5-[[6-Chloro-4-(trifluoromethyl)pyridazin-3-yl](cyano)methyl]-2-fluorobenzonitrile (C6)

To an ice-cold solution of 5-(cyanomethyl)-2-fluorobenzonitrile (1 eq.) and intermediate C4 (1.85 eq.) in dry THF (0.1 M) was added portionwise NaH (60 wt % in mineral oil, 2 eq.). The mixture was stirred 15 min at 0° C. and then 2 h at RT. The solution was quenched with sat. aq. NaHCO$_3$ solution and extracted with EtOAc (2x). The combined organic phases were dried (Na$_2$SO$_4$), filtered and concentrated to dryness under reduced pressure. The oily residue was purified by column chromatography on silica gel, eluting with 2-30% EtOAc/Petroleum ether to give the title compounds as a red oil. The two isomers C5 and C6 were obtained in a ratio of 2:1. MS (ES) $C_{14}H_5ClF_4N_4$ requires: 340, found: 341 (M+H)$^+$.

Step 5 2-Fluoro-5-{[6-oxo-5-(trifluoromethyl)-1,6-dihydropyridazin-3-yl]methyl}-benzoic acid (C7) and 2-Fluoro-5-{[6-oxo-4-(trifluoromethyl)-1,6-dihydropyridazin-3-yl]methyl}benzoic acid (C8)

The mixture of intermediates C5 and C6 were stirred in a mixture of AcOH/conc. aq. HCl/H$_2$O (2:1:1, 0.35 M) under heating in a microwave oven to 140° C. for 30 min. After cooling to RT the solvents were removed under reduced pressure and the residue was lyophilized from water/MeCN to afford a mixture (2:1 ratio) of the title compounds C7+C8 as a light yellow solid. MS (ES) $C_{13}H_8F_4N_2O_3$ requires: 316, found: 317 (M+H)$^+$.

PREPARATIVE EXAMPLE 4

2-Fluoro-5-{[4-methyl-6-oxo-5-(trifluoromethyl)-1,6-dihydropyridazin-3-yl]methyl}benzoic acid (D3)

Step 1: 3,6-Dichloro-4-methyl-5-(trifluoromethyl)pyridazine (D1)

To a stirred suspension of Preparative Example 3, C4 (1.0 eq) and AgNO$_3$ (0.5 eq.) in H$_2$O (0.15M) was added acetic acid (2.0 eq.). The mixture was heated to 50° C. and then a solution of conc. H$_2$SO$_4$ (3.0 eq.) in H$_2$O (0.5M) was added to the mixture. The temperature was then raised to 70° C. and a solution of ammonium persulfate (3.0 eq.) in H$_2$O (0.5M) was added dropwise over 10 min. The reaction mixture was heated at 70-75° C. for a further 30 min. After cooling, the reaction mixture was adjusted to pH=7 with 32% ammonium hydroxide solution, and extracted with Et$_2$O. The extracts were washed with brine, dried (Na$_2$SO$_4$) and the solvent was removed under reduced pressure. Crude product was purified by flash column chromatography on silica gel using 2-10% Et$_2$O/Petroleum ether, the desired D1 as a yellow oil (87% yield). $^1$H-NMR (300 MHz, CDCl$_3$, 300K) δ 2.66 (3H, s). MS (ES) $C_6H_3Cl_2F_3N_2$ requires: 231; 233, found: 232; 234 (M+H)$^+$.

Step 2: 5-[[6-Chloro-4-methyl-5-(trifluoromethyl)pyridazin-3-yl](cyano)methyl]-2-fluorobenzonitrile (D2) and 5-[[6-chloro-5-methyl-4-(trifluoromethyl)pyridazin-3-yl](cyano)methyl]-2-fluorobenzonitrile (D2a)

The procedure followed the one described in Preparative Example 1 step 1, starting from 5-(cyanomethyl)-2-fluorobenzonitrile (1.0 eq.), intermediate D1 (1.05 eq.) and NaH (2.0 eq.) in dry THF (0.1 M). Reaction mixture was purified by flash column chromatography on silica gel (Petroleum ether:EtOAc=95:5 to 3:2) to afford first the 5-methyl-4-trifluoromethyl isomer D2a (pale red solid, 30% yield) and then the desired 4-methyl-5-trifluoromethyl isomer D2 (yellow solid, 20% yield).

5-[[6-chloro-4-methyl-5-(trifluoromethyl)pyridazin-3-yl](cyano)methyl]-2-fluorobenzonitrile (D2): $^1$H-NMR (400 MHz, CDCl$_3$, 300K) δ: 7.97-7.87 (2H, m), 7.62 (1H, t, J=9.0 Hz), 6.59 (1H, s), 2.39-2.34 (3H, m). MS (ES) $C_{15}H_7ClF_4N_4$ required: 354; 356 found: 355; 357 (M+H)$^+$.

5-[[6-chloro-5-methyl-4-(trifluoromethyl)pyridazin-3-yl](cyano)methyl]-2-fluorobenzonitrile (D2a): $^1$H-NMR (400 MHz, CDCl$_3$, 300K) δ: 7.89-7.82 (2H, m), 7.63 (1H, t, J=9.0 Hz), 6.55 (1H, s), 2.56-2.52 (3H, m). MS (ES) $C_{15}H_7ClF_4N_4$ required: 354; 356 found: 355; 357 (M+H)$^+$.

Step 3: 2-Fluoro-5-{[4-methyl-6-oxo-5-(trifluoromethyl)-1,6-dihydropyridazin-3-yl]methyl}benzoic acid (D3)

The procedure followed the one described in Preparative Example 1, step 2 starting from D2. The titled compound D3 was obtained as pale brown solid (86% yield) after trituration with H$_2$O. $^1$H-NMR (400 MHz, CDCl$_3$, 300K) δ: 13.29 (1H, bs), 13.20 (1H, bs), 7.74-7.66 (1H, m), 7.49-7.40 (1H, m), 7.30-7.19 (1H, m), 4.08 (2H, s), 2.30-2.20 (3H, m). MS (ES) $C_{14}H_{10}F_4N_2O_3$ required: 330 found: 331 (M+H)$^+$.

PREPARATIVE EXAMPLE 5

5-{[4-Ethyl-6-oxo-5-(trifluoromethyl)-1,6-dihydropyridazin-3-yl]methyl}-2-fluorobenzoic acid (E1) and 5-{[5-Ethyl-6-oxo-4-(trifluoromethyl)-1,6-dihydropyridazin-3-yl]methyl}-2-fluorobenzoic acid (E2)

Compounds E1 and E2 ware prepared following the procedure described in Preparative Example 4, steps 1-3 but using propanoic acid in place of acetic acid. The two isomeric compounds were separated at the stage of the corresponding nitriles and carried through in separate reactions and the final product E1 and E2 were purified by flash column chromatography on silica gel 4-40% EtOAc/Petroleum ether. The two desired isomers were obtained as yellow solids (ratio E1:E2=1:3).

5-{[4-Ethyl-6-oxo-5-(trifluoromethyl)-1,6-dihydropyridazin-3-yl]methyl}-2-fluoro-benzoic acid (E1): $^1$H-NMR (400 MHz, DMSO-d$_6$, 300K) δ: 13.39 (1H, s), 13.22 (1H, br. s), 7.80-7.70 (1H, m), 7.50-7.40 (1H, s), 7.30-7.15 (1H, m), 4.10 (2H, s), 2.75-2.55 (2H, m), 1.15-0.90 (3H, m). MS (ES) $C_{15}H_{12}F_4N_2O_3$ required: 344, found: 345 (M+H)$^+$.

5-{[5-Ethyl-6-oxo-4-(trifluoromethyl)-1,6-dihydropyridazin-3-yl]methyl}-2-fluorobenzoic acid (E2): $^1$H-NMR (400 MHz, DMSO-d$_6$, 300K) δ: 13.41 (1H, s), 13.22 (1H, br. s), 7.70-7.76 (1H, m), 7.50-7.36 (1H, s), 7.30-7.20 (1H, m), 4.09 (2H, s), 2.78-2.57 (2H, m), 1.15-0.90 (3H, m). MS (ES) $C_{15}H_{12}F_4N_2O_3$ required: 344, found: 345 (M+H)$^+$.

PREPARATIVE EXAMPLE 6

5-[(4-Ethyl-5-methyl-6-oxo-1,6-dihydropyridazin-3-yl)methyl]-2-fluorobenzoic acid (F4) and 5-[(5-Ethyl-4-methyl-6-oxo-1,6-dihydropyridazin-3-yl)methyl]-2-fluorobenzoic acid (F5)

Step 1: 3,6-Dichloro-4-ethyl-5-methylpyridazine (F1)

F1 was prepared following the one described in Preparative Example 4, step 1 starting from 3,6-dichloro-4-methylpyridazine and using propionic acid instead of acetic acid. $^1$H-NMR (300 MHz, CDCl$_3$, 300K) δ 2.86 (2H, q, J=7.6 Hz), 2.45 (3H, s), 1.22 (3H, t, J=7.6 Hz). MS (ES) $C_7H_8Cl_2N_2$ requires: 190; 192, found: 191; 193 (M+H)$^+$.

Step 2: 5-[(6-chloro-4-ethyl-5-methylpyridazin-3-yl)(cyano)methyl]-2-fluorobenzonitrile (F2) and 5-[(6-chloro-5-ethyl-4-methylpyridazin-3-yl)(cyano)methyl]-2-fluorobenzonitrile (F3)

F2 and F3 were prepared following the one described in Preparative Example 4 step 2. The isomers were separated by RP-HPLC(YMC Hydrosphere C18, 20×150 mm; flow: 20 mL/min; isocratic: 60% H$_2$O (+0.1% TFA); 40% MeCN (+0.1% TFA). The combined fractions were basified with aq. sat. NaHCO$_3$ and partially concentrated under reduced pressure to remove MeCN. The aqueous was than extracted with EtOAc yielding the separated isomers after removal of the solvent under reduced pressure.

5-[(6-chloro-4-ethyl-5-methylpyridazin-3-yl)(cyano)methyl]-2-fluorobenzonitrile (F2): [First to elute] $^1$H-NMR (300 MHz, CDCl$_3$, 300K) δ: 7.78-7.65 (2H, m), 7.33-7.23 (1H, m), 5.73 (1H, s), 2.70 (2H, m), 2.44 (3H, s), 1.06 (3H, t, J=7.5 Hz). MS (ES) $C_{16}H_{12}ClFN_4$ required: 314; 316 found: 315; 317 (M+H)$^+$.

5-[(6-chloro-5-ethyl-4-methylpyridazin-3-yl)(cyano)methyl]-2-fluorobenzonitrile (F3): $^1$H-NMR (300 MHz, CDCl$_3$, 300K) δ: 7.74-7.64 (2H, m), 7.34-7.24 (1H, m), 5.76 (1H, s), 2.84 (2H, q, J=7.6 Hz), 2.31 (3H, s), 1.21 (3H, t, J=7.6 Hz). MS (ES) $C_{16}H_{12}ClFN_4$ required: 314; 316 found: 315; 317 (M+H)$^+$.

Step 3: 5-[(4-Ethyl-5-methyl-6-oxo-1,6-dihydropyridazin-3-yl)methyl]-2-fluorobenzoic acid (F4) and 5-[(5-Ethyl-4-methyl-6-oxo-1,6-dihydropyridazin-3-yl)methyl]-2-fluorobenzoic acid (F5)

F4 and F5 were prepared following the one described in Preparative Example 1, step 2 starting from F2 or F3 respectively. The titled compounds were obtained after trituration with H$_2$O.

5-[(4-Ethyl-5-methyl-6-oxo-1,6-dihydropyridazin-3-yl)methyl]-2-fluorobenzoic acid (F4): $^1$H-NMR (400 MHz, DMSO, 300K) δ: 13.22 (1H, br. s), 12.71 (1H, s), 7.70 (1H, m), 7.46 (1H, m), 7.24 (1H, m), 4.00 (2H, s), 2.43 (2H, m), 2.01 (3H, s), 0.89 (3H, t, J=6.8 Hz). MS (ES) $C_{15}H_{15}FN_2O_3$ required: 290 found: 291 (M+H)$^+$.

5-[(5-Ethyl-4-methyl-6-oxo-1,6-dihydropyridazin-3-yl)methyl]-2-fluorobenzoic acid (F5): $^1$H-NMR (400 MHz, DMSO, 300K) δ: 13.20 (1H, br.s), 12.64 (1H, s), 7.68 (1H, m), 7.43 (1H, m), 7.24 (1H, m), 3.97 (2H, s), 2.50 (2H, m), 2.05 (3H, s), 0.97 (3H, m). MS (ES) $C_{15}H_{15}FN_2O_3$ required: 290 found: 291 (M+H)$^+$.

PREPARATIVE EXAMPLE 7

4-(3,3-Dimethylcyclohexyl)-3-oxopiperazin-1-ium trifluoroacetate (G1)

To a solution (0.19 M) of methyl N-(tert-butoxycarbonyl)-N-(2-oxoethyl)glycinate (prepared as described in *Bioorg. Med. Chem.* 2007, 15, 2092-2105) in MeOH were added 3,3-dimethylcyclohexanamine hydrochloride (1.5 eq), DIPEA (1.5 eq), NaBH$_3$(CN) (1.5 eq) and AcOH (1.4 eq). After stirring for 2 hours at RT more NaBH$_3$(CN) (1.5 eq) was added and reaction mixture was irradiated at MW for 1 hour at 125° C. MeOH was removed under reduced pressure and the residue purified by filtration on silica with elution of the desired intermediate with EtOAc. Evaporation of the organic solvent yielded tert-butyl 4-(3,3-dimethylcyclohexyl)-3-oxopiperazine-1-carboxylate. MS (ES) $C_{17}H_{30}N_2O_3$ requires: 310, found: 311 (M+H)$^+$.

The residue was dissolved in a mixture of DCM and TFA (2:1) and after stirring at RT for 30 minutes removal of the solvent under reduced pressure afforded the titled compound (G1). MS (ES) $C_{12}H_{22}N_2O$ requires: 210, found: 211 (M+H)$^+$.

PREPARATIVE EXAMPLE 8

1-(3-Thienyl)piperazin-2-one (H2)

Step 1: tert-Butyl 3-oxo-4-(3-thienyl)piperazine-1-carboxylate (H1)

A mixture of 1-Boc-3-oxopiperazine (1.0 eq.), 3-bromothiophene (1.5 eq.), $K_3PO_4$ (2.0 eq.), CuI (0.4 eq.) and N,N'-dimethylethylendiamine (0.8 eq.) in 1,4-dioxane (0.5M) was put in a sealed vial and stirred at 110° C. for 18 hr. Reaction mixture was diluted with EtOAc and filtered through a pad of SolcaFloc® 200 FCC. After removal of the solvent, the crude product was purified by flash column chromatography on silica gel using 10-40% EtOAc/Petroleum ether as eluent to afford the desired product H1 as pink solid (80% yield). $^1$H NMR (400 MHz, CDCl$_3$, 300K) δ 7.32-7.28 (3H, m), 4.25 (2H, s), 3.82-3.75 (4H, m), 1.49 (9H, s). MS (ES) $C_{13}H_{18}N_2O_3S$ requires: 282, found: 283 (M+H)$^+$.

Step 2: 1-(3-Thienyl)piperazin-2-one (H2)

A solution of H1 (1.0 eq.) in DCM/TFA (4:1, 0.07M) was stirred for 1 hr at RT. After completion of the reaction, solvent was evaporated under reduced pressure and the crude product isolated as the free base by using an Isolute® SCX cartridge. The desired product G2 was obtained as a pale red solid (97% yield). $^1$H-NMR (400 MHz, DMSO-d$_6$, 300K) δ 7.62-7.56 (2H, m), 7.55-7.49 (1H, m), 3.76 (2H, t, J=5.4 Hz), 3.50 (2H, s), 3.11 (2H, t, J=5.4 Hz). MS (ES) $C_8H_{10}N_2OS$ requires: 182, found: 183 (M+H)$^+$.

PREPARATIVE EXAMPLE 9

1-[5-(Trifluoromethyl)pyridin-3-yl]piperazin-2-one (I2)

Step 1: tert-Butyl 3-oxo-4-[4-(trifluoromethyl)pyridin-2-yl]piperazine-1-carboxylate (I1)

A mixture of 1-Boc-3-oxopiperazine (1.0 eq.), 2-bromo-4-(trifluoromethyl)pyridine (1.5 eq.) and Cs$_2$CO$_3$ (1.5 eq.) in 1,4-dioxane (0.5M) was degassed under Argon flow for 30 min, then Pd(OAc)$_2$ (0.1 eq.) and Xantphos (0.15 eq.) were added, the vial was sealed and stirring was continued at 110° C. for 18 hr. Reaction mixture was diluted with EtOAc and filtered through a pad of SolcaFloc® 200 FCC. After removal of the solvent, the crude product was purified by flash column chromatography on silica gel using 10-40% EtOAc/Petroleum ether as eluent to afford the desired product I1 as yellow solid (92% yield). $^1$H NMR (400 MHz, CDCl$_3$, 300K) δ 8.57 (1H, d, J=4.8 Hz), 8.40 (1H, bs), 7.32 (1H, d, J=4.8 Hz), 4.31 (2H, s), 4.17 (2H, t, J=5.3 Hz), 3.76 (2H, t, J=5.3 Hz), 1.50 (9H, s). MS (ES) $C_{15}H_{18}F_3N_3O_3$ requires: 345, found: 346 (M+H)$^+$.

Step 2: 1-[4-(Trifluoromethyl)pyridin-2-yl]piperazin-2-one (I2)

A solution of I1 (1.0 eq.) in DCM/TFA (4:1, 0.07M) was stirred for 1 hr at RT. After completion of the reaction, solvent was evaporated under reduced pressure and the crude product was isolated as the free base by using an Isolute® SCX cartridge. The desired product 12 was obtained as a pale red solid (100% yield). $^1$H-NMR (400 MHz, DMSO-d$_6$, 300K) δ 8.72 (1H, d, J=5.0 Hz), 8.32 (1H, bs), 7.57 (1H, d, J=5.0 Hz), 3.89 (2H, t, J=5.0 Hz), 3.50 (2H, s), 3.05 (2H, t, J=5.0 Hz). MS (ES) $C_{10}H_{10}F_3N_3O$ requires: 245, found: 246 (M+H)$^+$.

EXAMPLE 1

6-{4-Fluoro-3-[(3-oxo-4-phenylpiperazin-1-yl)carbonyl]benzyl}-4,5-dimethyl-3-oxo-2,3-dihydropyridazin-1-ium trifluoroacetate (AA1)

A mixture of 5-[(4,5-dimethyl-6-oxo-1,6-dihydropyridazin-3-yl)methyl]-2-fluorobenzoic acid (Preparative Example 2) (1.0 eq), TBTU (1.5 eq) and DIPEA (1.5 eq) in DMF (0.1 M) was stirred at RT for 30 min then 1-phenylpiperazin-2-one (1.5 eq) was added and stirring was continued O/N at RT. The reaction mixture was diluted with EtOAc, washed sequentially with sat. aq. NaHCO$_3$ solution, 1N HCl, and brine. The solution was dried (Na$_2$SO$_4$), filtered and concentrated under reduced pressure. The crude product was purified by preparative RP-HPLC using H$_2$O (0.1% TFA) and MeCN (0.1% TFA) as eluents and the desired fractions were lyophilized to afford the titled compound AA1 as a white solid.

$^1$H-NMR (300 MHz, DMSO-d$_6$, 300K) δ: 12.67 (1H, s), 7.46-7.20 (8H, m), 4.33 (1H, m), 3.97 (4H, m), 3.81 (1H, m), 3.66 (1H, m), 3.60 (1H, m), 2.00 (6H, br. s). MS (ES) $C_{24}H_{23}FN_4O_3$ requires: 434, found: 435 (M+H)$^+$.

EXAMPLE 2

6-{3-[(4-Cyclohexyl-3-oxopiperazin-1-yl)carbonyl]-4-fluorobenzyl}-4,5-dimethyl-3-oxo-2,3-dihydropyridazin-1-ium trifluoroacetate (BB2)

BB2 was prepared as described for Example 1 using 1-cyclohexylpiperazin-2-one (1.5 eq). The crude product was purified by preparative RP-HPLC using H$_2$O (0.1% TFA) and MeCN (0.1% TFA) as eluents. The desired fractions were lyophilized to afford the titled compound BB2 as a white solid. $^1$H-NMR (300 MHz, DMSO-d$_6$, 300K) δ: 12.66 (1H, s), 7.35-7.14 (3H, m), 4.30-4.08 (2H, m), 3.94 (2H, br. s), 3.84-3.71 (2H, m), 3.39 (1H, m), 3.31 (1H, m), 3.19 (1H, m), 2.04 (6H, br. s), 1.8-0.9 (10H, m). MS (ES) $C_{24}H_{29}FN_4O_3$ requires: 440, found: 441 (M+H)$^+$.

EXAMPLE 3

6-{3-[(4-Cyclopentyl-3-oxopiperazin-1-yl)carbonyl]-4-fluorobenzyl}-4,5-dimethylpyridazin-3(2H)-one (CC3)

CC3 was prepared as described for Example 1 using 4-cyclopentyl-3-oxopiperazin-1-ium trifluoroacetate (1.5 eq). The crude product was purified by flash column chromatography on silica eluting with 1-10% MeOH/DCM to yield CC3 as a white solid. $^1$H-NMR (300 MHz, DMSO-d$_6$, 300K) δ: 12.71 (1H, s), 7.42-7.25 (3H, m), 4.80 (1H, m), 4.21 (1H, s), 4.02 (2H, s), 3.86 (2H, s), 3.52-3.24 (3H, m), 2.05 (6H, m), 1.81-1.49 (8H, m). MS (ES) $C_{23}H_{27}FN_4O_3$ requires: 426, found: 427 (M+H)$^+$.

The Examples in the following table were prepared according to the procedures described in the previous Examples.

| Example | Name | MWt | [M + H]$^+$ |
|---|---|---|---|
| 4 | 6-{4-Fluoro-3-[(3-oxo-4-phenylpiperazin-1-yl)carbonyl]benzyl}-4,5-dimethylpyridazin-3(2H)-one hydrochloride | 434 | 435 |
| 5 | 4-Ethyl-6-{4-fluoro-3-[(3-oxo-4-phenylpiperazin-1-yl)carbonyl]benzyl}pyridazin-3(2H)-one trifluoroacetate | 434 | 435 |
| 6 | 6-{3-[(4-Cyclohexyl-3-oxopiperazin-1-yl)carbonyl]-4-fluorobenzyl}-4-ethylpyridazin-3(2H)-one trifluoroacetate | 440 | 441 |
| 7 | 3-{4-Fluoro-3-[(4-methyl-3-oxopiperazin-1-yl)carbonyl]benzyl}-4,5-dimethyl-6-oxo-1,6-dihydropyridazin-1-ium trifluoroacetate | 372 | 373 |
| 8 | 3-(4-Fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate | 466 | 467 |
| 9 | 6-(3-{[4-(3-Chlorophenyl)-3-oxopiperazin-1-yl]carbonyl}-4-fluorobenzyl)-4,5-dimethyl-3-oxo-2,3-dihydropyridazin-1-ium trifluoroacetate | 468 | 469 |
| 10 | 6-(3-{[4-(3-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate | 486 | 487 |
| 11 | 6-(3-{[4-(3,4-Difluorophenyl)-3-oxopiperazin-1-yl]carbonyl}-4-fluorobenzyl)-4,5-dimethyl-3-oxo-2,3-dihydropyridazin-1-ium trifluoroacetate | 470 | 471 |
| 12 | 6-(3-{[4-(3,5-Difluorophenyl)-3-oxopiperazin-1-yl]carbonyl}-4-fluorobenzyl)-4,5-dimethyl-3-oxo-2,3-dihydropyridazin-1-ium trifluoroacetate | 470 | 471 |
| 13 | 6-(3-{[4-(4-Chlorophenyl)-3-oxopiperazin-1-yl]carbonyl}-4-fluorobenzyl)-4,5-dimethyl-3-oxo-2,3-dihydropyridazin-1-ium trifluoroacetate | 468 | 469 |
| 14 | 6-(3-{[4-(2-Chlorophenyl)-3-oxopiperazin-1-yl]carbonyl}-4-fluorobenzyl)-4,5-dimethyl-3-oxo-2,3-dihydropyridazin-1-ium trifluoroacetate | 468 | 469 |
| 15 | 6-[4-Fluoro-3-({3-oxo-4-[2-(trifluoromethyl)phenyl]piperazin-1-yl}carbonyl)benzyl]-4,5-dimethyl-3-oxo-2,3-dihydropyridazin-1-ium trifluoroacetate | 502 | 503 |
| 16 | 6-(3-{[4-(2-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate | 486 | 487 |
| 17 | 6-{3-[(4-Ethyl-3-oxopiperazin-1-yl)carbonyl]-4-fluorobenzyl}-4,5-dimethylpyridazin-3(2H)-one trifluoroacetate | 386 | 387 |
| 18 | 6-{3-[(4-Butyl-3-oxopiperazin-1-yl)carbonyl]-4-fluorobenzyl}-4,5-dimethylpyridazin-3(2H)-one trifluoroacetate | 414 | 415 |
| 19 | 6-(3-{[4-(3,5-Dimethylbenzyl)-3-oxopiperazin-1-yl]carbonyl}-4-fluorobenzyl)-4,5-dimethylpyridazin-3(2H)-one trifluoroacetate | 476 | 477 |
| 20 | 6-(4-Fluoro-3-{[4-(4-methoxybenzyl)-3-oxopiperazin-1-yl]carbonyl}benzyl)-4,5-dimethylpyridazin-3(2H)-one trifluoroacetate | 478 | 479 |
| 21 | 6-(4-Fluoro-3-{[3-oxo-4-(2-phenylethyl)piperazin-1-yl]carbonyl}benzyl)-4,5-dimethylpyridazin-3(2H)-one trifluoroacetate | 462 | 463 |
| 22 | 6-(4-Fluoro-3-{[4-(3-methoxyphenyl)-3-oxopiperazin-1-yl]carbonyl}benzyl)-4,5-dimethylpyridazin-3(2H)-one trifluoroacetate | 464 | 465 |
| 23 | 6-(3-{[4-(3,5-Dimethylphenyl)-3-oxopiperazin-1-yl]carbonyl}-4-fluorobenzyl)-4,5-dimethylpyridazin-3(2H)-one trifluoroacetate | 462 | 463 |
| 24 | Methyl (4-{5-[(4,5-dimethyl-6-oxo-1,6-dihydropyridazin-3-yl)methyl]-2-fluorobenzoyl}-2-oxopiperazin-1-yl)acetate trifluoroacetate | 430 | 431 |
| 25 | 3-{3-[(4-Cyclohexyl-3-oxopiperazin-1-yl)carbonyl]-4-fluorobenzyl}-4-methyl-6-oxo-5-(trifluoromethyl)-1,6-dihydropyridazin-1-ium trifluoroacetate | 494 | 495 |
| 26 | 3-(3-{[4-(3,4-Difluorophenyl)-3-oxopiperazin-1-yl]carbonyl}-4-fluorobenzyl)-4-methyl-6-oxo-5-(trifluoromethyl)-1,6-dihydropyridazin-1-ium trifluoroacetate | 524 | 525 |
| 27 | 6-{3-[(4-Cyclohexyl-3-oxopiperazin-1-yl)carbonyl]-4-fluorobenzyl}-3-oxo-4-(trifluoromethyl)-2,3-dihydropyridazin-1-ium trifluoroacetate | 480 | 481 |
| 28 | 3-{3-[(4-Cyclohexyl-3-oxopiperazin-1-yl)carbonyl]-4-fluorobenzyl}-4-ethyl-5-methyl-6-oxo-1,6-dihydropyridazin-1-ium trifluoroacetate | 454 | 455 |
| 29 | 3-{3-[(4-Cyclohexyl-3-oxopiperazin-1-yl)carbonyl]-4-fluorobenzyl}-5-ethyl-4-methyl-6-oxo-1,6-dihydropyridazin-1-ium trifluoroacetate | 454 | 455 |
| 30 | 3-{3-[(4-Cyclopentyl-3-oxopiperazin-1-yl)carbonyl]-4-fluorobenzyl}-5-ethyl-6-oxo-1,6-dihydropyridazin-1-ium trifluoroacetate | 426 | 427 |
| 31 | 3-{4-Fluoro-3-[(3-oxo-4-pyridin-2-ylpiperazin-1-yl)carbonyl]benzyl}-4,5-dimethyl-6-oxo-1,6-dihydropyridazin-1-ium trifluoroacetate | 435 | 436 |
| 32 | 6-{4-Fluoro-3-[(4-oxooctahydro-2H-pyrido[1,2-a]pyrazin-2-yl)carbonyl]benzyl}-4,5-dimethyl-3-oxo-2,3-dihydropyridazin-1-ium trifluoroacetate | 412 | 413 |

EXAMPLE 33

6-{3-[(4-Cyclopentyl-3-oxopiperazin-1-yl)carbonyl]-4-fluorobenzyl}-3-oxo-4-(trifluoromethyl)-2,3-dihydropyridazin-1-ium trifluoroacetate (DD1)

The mixture of Preparative Example 3, C7 and C8 was dissolved in DMF (0.1 M). TBTU (1 eq.) and TEA (2 eq.) were added, together with 4-cyclopentyl-3-oxopiperazin-1-ium trifluoroacetate (1 eq.). The mixture was stirred for 3 h at RT and the product was isolated by prep. RP-HPLC (using H$_2$O/MeCN, 0.1% TFA as eluents). The pooled product fractions were lyophilized to afford the title compound DD1 as a white solid. $^1$H-NMR (300 MHz, DMSO-d$_6$) δ: 13.53 (1H, bs), 7.90 (1H, s), 7.45-7.22 (3H, m), 4.75-4.61 (1H, m), 4.12 (1.2H, s), 4.02 (2H, s), 3.84-3.80 (1.6H, m), 3.45-3.40 (1.2H, m), 3.38-3.25 (0.8H, m), 3.21-3.17 (1.2H, m), 1.75-1.38 (8H, m). MS (ES) $C_{22}H_{22}F_4N_4O_3$ requires: 466, found: 467 (M+H)$^+$.

EXAMPLE 34

6-{3-[(4-Cyclohexyl-3-oxo-1,4-diazepan-1-yl)carbonyl]-4-fluorobenzyl}-4,5-dimethyl-3-oxo-2,3-dihydropyridazin-1-ium trifluoroacetate (EE4)

Step 1: tert-Butyl[3-(cyclohexylamino)propyl]carbamate (EE1)

A solution of cyclohexanone (6.0 eq) and tert-butyl (3-aminopropyl)carbamate (1.0 eq) in MeOH (1.5 M) was stirred at RT for 2 h and treated with NaBH$_3$(CN) (6.0 eq). TFA was added until pH 6, and stirring was continued for 24 h at RT. The reaction mixture was diluted with EtOAc, washed sequentially with sat. aq. NaHCO$_3$ solution and brine. The solution was dried (Na$_2$SO$_4$), filtered and concentrated under reduced pressure. The crude product was purified by column chromatography on silica gel, eluting with EtOAc to afford the title compound EE1 (46% yield). $^1$H-NMR (500 MHz, DMSO-d$_6$, 300K) δ: 8.12 (1H, br. s), 3.04-2.91 (3H, m), 2.91-2.82 (2H, m), 2.00-1.91 (1H, m), 1.78-1.53 (5H, m), 1.37 (9H, s), 1.24-1.12 (6H, m). MS (ES) C$_{14}$H$_{28}$N$_2$O$_2$ required: 256, found: 257 (M+H)$^+$.

Step 2: tert-butyl {3-[(chloroacetyl)(cyclohexyl)amino]propyl}carbamate (EE2)

Et$_3$N (3.3 eq) and chloroacetyl chloride (3.0 eq) were added to a solution of EE1 (1.0 eq) in THF (0.5 M) at −10° C. and the mixture was stirred at RT overnight. The reaction mixture was diluted with EtOAc, washed sequentially with sat. aq. NaHCO$_3$ solution and brine. The solution was dried (Na$_2$SO$_4$), filtered and concentrated under reduced pressure. The crude product was purified by column chromatography on silica gel, eluting with 8:2 DCM/Petroleum ether to afford the desired compound EE2 (46% yield). $^1$H-NMR (300 MHz, DMSO-d$_6$, 300K) δ: 7.00-6.85 (1H, m), 4.46 (1.3H, s), 4.34 (0.7H, s), 4.12-3.90 (0.35H, m), 3.70-3.53 (0.65H, m), 3.31-3.13 (2H, m), 3.06-2.84 (2H, m), 1.83-1.48 (8H, m), 1.43 (9H, s), 1.37-1.05 (4H, m). MS (ES) C$_{16}$H$_{29}$ClN$_2$O$_3$ required: 332, found: 333 (M+H)$^+$.

Step 3: tert-butyl 4-cyclohexyl-3-oxo-1,4-diazepane-1-carboxylate (EE3)

To intermediate EE2 (1.0 eq) in dry DMF (0.03 M) at 0° C. was slowly added a suspension of NaH (3.0 eq), dissolved in dry DMF (0.03 M). The reaction mixture was allowed to warm to RT and stirred for 3.5 h. The mixture was cooled again and quenched by addition of water. The reaction mixture was diluted with EtOAc. The organic phase was washed 0.5 N HCl (2×) and brine. The organic phase was dried (Na$_2$SO$_4$), filtered and concentrated under reduced pressure to afford the desired compound EE3 (80% yield). $^1$H-NMR (300 MHz, DMSO-d$_6$, 300K) δ: 4.18-4.03 (1H, m), 3.98 (2H, s), 3.48-3.37 (2H, m), 3.36-3.25 (2H, m), 1.80-1.10 (12H, m), 1.38 (9H, s). MS (ES) C$_{16}$H$_{28}$N$_2$O$_3$ required: 296, found: 297 (M+H)$^+$.

Step 4: 6-{3-[(4-cyclohexyl-3-oxo-1,4-diazepan-1-yl)carbonyl]-4-fluorobenzyl}-4,5-dimethyl-3-oxo-2,3-dihydropyridazin-1-ium trifluoroacetate (EE4)

Intermediate EE3 was solved in TFA/DCM (1:1) and the mixture was stirred for 3 h and solvent was removed under reduced pressure. The crude reaction mixture was then converted to the desired using the procedure described for Example 1. The crude was purified by preparative RP-HPLC using H$_2$O (0.1% TFA) and MeCN (0.1% TFA) as eluent and desired fractions were lyophilized to afford the titled compound EE4 as a white solid (35% yield). $^1$H-NMR (300 MHz, DMSO-d$_6$, 300K) δ: 12.60 (1H, s), 7.30-6.75 (3H, m), 4.24 (1H, s), 4.10-3.92 (1H, m), 3.92-3.83 (3H, m), 3.69-3.60 (1H, m), 3.35-3.18 (3H, m), 1.90 (6H, s), 1.60-0.98 (12H, m). MS (ES) C$_{25}$H$_{31}$FN$_4$O$_3$ required: 455, found: 456 (M+H)$^+$.

EXAMPLE 35

6-{3-[(4-Cyclohexyl-2-methyl-3-oxopiperazin-1-yl)carbonyl]-4-fluorobenzyl}-4,5-dimethyl-3-oxo-2,3-dihydropyridazin-1-ium trifluoroacetate (FF3)

Step 1: tert-butyl 4-cyclohexyl-3-oxopiperazine-1-carboxylate (FF1)

To a stirred solution of 4-cyclohexyl-3-oxopiperazin-1-ium trifluoroacetate (1 eq) in DCM (0.1 M) was added Et$_3$N (2 eq) and, after 5, min Boc$_2$O (1.3 eq). The mixture was stirred overnight at RT. NH$_3$ solution in MeOH (7N, 0.3 eq) was added and the reaction mixture was diluted with EtOAc. The organic phase was washed sat. aq. NaHCO$_3$ solution (2×) and brine. The solution was dried (Na$_2$SO$_4$), filtered and concentrated under reduced pressure to afford the desired compound FF1 (95% yield). $^1$H-NMR (300 MHz, DMSO-d$_6$, 300K) δ: 4.26-4.11 (1H, m), 3.85 (2H, s), 3.51-3.39 (2H, m), 3.27-3.18 (2H, m), 1.79-1.65 (2H, m), 1.40 (9H, s), 1.62-1.00 (8H, m).

MS (ES) C$_{15}$H$_{26}$N$_2$O$_3$ required: 282, found: 283 (M+H)$^+$.

Step 2: tert-butyl 4-cyclohexyl-2-methyl-3-oxopiperazine-1-carboxylate (FF2)

A solution of intermediate FF1 (1 eq) in THF (0.05 M) was cooled to −78° C. and LiHMDS (1.2 eq) was added, after 10 min, MeI (3 eq) was added and the mixture was stirred at −78° C. for 30 min. The mixture was quenched by addition of water, diluted with EtOAc and the organic phase was washed twice with sat. aq. NaHCO$_3$ solution and brine. The solution was dried (Na$_2$SO$_4$), filtered and concentrated under reduced pressure to afford the desired compound FF2. MS (ES) C$_{16}$H$_{28}$N$_2$O$_3$ required: 296, found: 297 (M+H)$^+$.

Step 3: 6-{3-[(4-Cyclohexyl-2-methyl-3-oxopiperazin-1-yl)carbonyl]-4-fluorobenzyl}-4,5-dimethyl-3-oxo-2,3-dihydropyridazin-1-ium trifluoroacetate (FF3)

Intermediate FF2 was solved in TFA/DCM (1:1) and the mixture was stirred for 3 h and concentrated under reduced pressure. The mixture was then converted to FF3 using the procedure described for Example 1. The crude was purified by preparative RP-HPLC using H$_2$O (0.1% TFA) and MeCN (0.1% TFA) as eluent and desired fractions were lyophilized to afford the titled compound FF3 as a white solid (35% yield). $^1$H-NMR (300 MHz, DMSO-d$_6$, 300K) δ: 12.64 (1H, s), 7.40-7.12 (3H, m), 4.80-4.62 (0.7H, m), 4.50-4.30 (0.3H, m), 4.30-4.12 (0.7H, m), 3.85-3.68 (0.3H, m), 3.96 (2H, s), 3.42-3.10 (4H, m), 2.00 (3H, m s), 1.96 (3H, s), 1.80-0.95 (10H, m), 1.34 (3H, d, J=6.9 Hz). MS (ES) C$_{25}$H$_{31}$FN$_4$O$_3$ required: 454, found: 455 (M+H)$^+$.

EXAMPLE 36

6-{4-Fluoro-3-[(4-isopropyl-5-oxo-1,4-diazepan-1-yl)carbonyl]benzyl}-4,5-dimethyl-3-oxo-2,3-dihydropyridazin-1-ium trifluoroacetate (GG1)

GG1 was prepared following the one described in Preparative Example 1 using 4-isopropyl-1,4-diazepan-5-one. The crude was purified by preparative RP-HPLC using $H_2O$ (0.1% TFA) and MeCN (0.1% TFA) as eluent and desired fractions were lyophilized to afford the titled compound GG1 as a white solid (66% yield). $^1$H-NMR (300 MHz, DMSO-d6, 300K) d: 12.65 (1H, s), 7.33-7.10 (3H, m), 4.70-4.50 (2H, m), 4.40-4.08 (2H, m), 3.92 (2H, s), 3.82-3.55 (2H, m), 3.50-3.35 (1H, m), 3.33-3.20 (2H, m), 1.99 (6H, br. s), 1.50 (3H, d, J=6.67 Hz), 1.42 (3H, d, J=6.7 Hz). MS (ES) $C_{22}H_{27}FN_4O_3$ required: 414, found: 415 $(M+H)^+$.

EXAMPLE 37

3-{3-[(4-Cyclohexyl-2,2-dimethyl-3-oxopiperazin-1-yl)carbonyl]-4-fluorobenzyl}-4,5-dimethyl-6-oxo-1,6-dihydropyridazin-1-ium trifluoroacetate (HH5)

Step 1: tert-Butyl[2-(cyclohexylamino)ethyl]carbamate (HH1)

To a stirred solution of tert-butyl N-(2-oxoethyl) carbamate in MeOH (0.2 M), was added cyclohexylamine (1.1 eq). After 30 min, the mixture was treated with $NaBH_4$ (1.2 eq) and stirring was continued for another 10 min. The mixture was quenched with water and concentrated under reduced pressure to remove the methanol. The aqueous slurry was saturated with NaCl and extracted with EtOAc (2×). The organic phase was dried ($Na_2SO_4$), filtered and concentrated under reduced pressure to yield HH1 a pale yellow oil which solidified upon standing. MS (ES) $C_{13}H_{26}N_2O_2$ requires: 242, found: 243 $(M+H)^+$.

Step 2: tert-Butyl {2-[(2-bromo-2-methylpropanoyl)(cyclohexyl)amino]ethyl}carbamate (HH2)

To a solution of 2-bromo-2-methylpropionyl bromide (1.1 eq) in DCM (0.38 M) at −10° C. a solution of intermediate x1 (1 eq) and TEA (1.1 eq) in DCM (0.38 M) was added dropwise. The mixture was stirred at −10° C. for 30 min and then left stirring at RT overnight. The residue was partitioned between EtOAc and water and separated. The aqueous phase was reextracted with EtOAc and then the combined organic layers were dried ($Na_2SO_4$), filtered and concentrated under reduced pressure to yield HH2. MS (ES) $C_{17}H_{31}BrN_2O_3$ requires: 390/392, found: 391/393 $(M+H)^+$.

Step 3: N-(2-Aminoethyl)-2-bromo-N-cyclohexyl-2-methylpropanamide (HH3)

A solution of intermediate HH2 (1 eq) in DCM/TFA (1:1, 0.128 M) was stirred at RT and then concentrated under reduced pressure. The resulting crude was partitioned between DCM and sat. aq. $NaHCO_3$ solution. The organic phase was dried ($Na_2SO_4$), filtered and concentrated under reduced pressure to yield HH3. MS (ES) $C_{12}H_{23}BrN_2O$ requires: 290/292, found: 291/293 $(M+H)^+$.

Step 4: 1-Cyclohexyl-3,3-dimethylpiperazin-2-one (HH4)

A solution of intermediate HH3 (1.0 eq) and $K_2CO_3$ (2 eq) in EtOH (0.1 M) was stirred for 10 min at 120° C. under MW irradiation. Solvent was evaporated under reduced pressure to yield HH3. MS (ES) $C_{12}H_{22}N_2O$ requires: 210, found: 211 $(M+H)^+$.

Step 5: 3-{3-[(4-Cyclohexyl-2,2-dimethyl-3-oxopiperazin-1-yl)carbonyl]-4-fluorobenzyl}-4,5-dimethyl-6-oxo-1,6-dihydropyridazin-1-ium trifluoroacetate (HH5)

A mixture of 5-[(4,5-dimethyl-6-oxo-1,6-dihydropyridazin-3-yl)methyl]-2-fluorobenzoic acid (Preparative Example 2) (1.0 eq), HATU (1.5 eq) and DMAP (1.5 eq) in DMF (0.25 M) was stirred at RT for 30 min then intermediate HH4 (1.1 eq) was added and stirring was continued overnight at RT. The crude product was purified by preparative RP-HPLC using $H_2O$ (0.1% TFA) and MeCN (0.1% TFA) as eluents and the desired fractions were lyophilized to afford the desired compound. $^1$H-NMR (400 MHz, DMSO-d$_6$, 300K) δ: 12.67 (1H, s), 7.29-7.18 (3H, m), 4.10 (1H, m), 3.97 (2H, m), 3.30 (2H, m), 3.23 (2H, m), 2.02 (3H, s), 2.00 (3H, s), 1.78-1.70 (2H, m), 1.68 (6H, s), 1.63-1.48 (3H, m), 1.43-1.21 (4H, m), 1.13-0.98 (1H, m). MS (ES) $C_{26}H_{33}FN_4O_3$ requires: 468, found: 469 $(M+H)^+$.

The Examples in the following table were prepared according to the procedures described in the previous Examples.

| Example | Name | Mwt | $[M + H]^+$ |
|---|---|---|---|
| 38 | 6-{4-Fluoro-3-[(3-oxo-4-pyridin-3-ylpiperazin-1-yl)carbonyl]benzyl}-4,5-dimethylpyridazin-3(2H)-one | 435.5 | 436 |
| 39 | 6-{3-[(4-Cyclohexyl-3-oxopiperazin-1-yl)carbonyl]-4-fluorobenzyl}-5-ethyl-4-(trifluoromethyl)pyridazin-3(2H)-one trifluoroacetate | 508.5 | 509 |
| 40 | 6-(4-Fluoro-3-{[4-(4-fluorophenyl)-3-oxopiperazin-1-yl]carbonyl}benzyl)-4,5-dimethyl-3-oxo-2,3-dihydropyridazin-1-ium trifluoroacetate | 452.5 | 453 |
| 41 | (1S,4S)-5-{5-[(4,5-Dimethyl-6-oxo-1,6-dihydropyridazin-3-yl)methyl]-2-fluorobenzoyl}-2-phenyl-2,5-diazabicyclo[2.2.1]heptan-3-one trifluoroacetate | 446.5 | 447 |
| 42 | 3-(3-{[4-(3,5-Dichlorophenyl)-3-oxopiperazin-1-yl]carbonyl}-4-fluorobenzyl)-4,5-dimethyl-6-oxo-1,6-dihydropyridazin-1-ium trifluoroacetate | 503.4 | 503; 505 |
| 43 | 3-(4-Fluoro-3-{[4-(1-naphthyl)-3-oxopiperazin-1-yl]carbonyl}benzyl)-4,5-dimethyl-6-oxo-1,6-dihydropyridazin-1-ium trifluoroacetate | 484.5 | 485 |
| 44 | 3-(4-Fluoro-3-{[3-oxo-4-(2-thienyl)piperazin-1-yl]carbonyl}benzyl)-4,5-dimethyl-6-oxo-1,6-dihydropyridazin-1-ium trifluoroacetate | 440.5 | 441 |
| 45 | 6-(4-Fluoro-3-{[3-oxo-4-(3,3,3-trifluoro-2-methylpropyl)piperazin-1-yl]carbonyl}benzyl)-4,5-dimethyl-3-oxo-2,3-dihydropyridazin-1-ium trifluoroacetate | 468.5 | 469 |
| 46 | 6-(3-{[4-(2,2-Difluoro-1-phenylethyl)-3-oxopiperazin-1-yl]carbonyl}-4-fluorobenzyl)-4,5-dimethyl-3-oxo-2,3-dihydropyridazin-1-ium trifluoroacetate | 498.5 | 499 |
| 47 | 6-(4-Fluoro-3-{[3-oxo-4-(tetrahydro-2H-pyran-3-yl)piperazin-1-yl]carbonyl}benzyl)-4,5-dimethyl-3- | 442.5 | 443 |

| Example | Name | Mwt | [M + H]+ |
|---|---|---|---|
| 48 | oxo-2,3-dihydropyridazin-1-ium trifluoroacetate<br>6-(3-{[4-(4,4-Difluorocyclohexyl)-3-oxopiperazin-1-yl]carbonyl}-4-fluorobenzyl)-4,5-dimethyl-3-oxo-2,3-dihydropyridazin-1-ium trifluoroacetate | 476.5 | 477 |
| 49 | 6-(3-{[4-(3,3-Difluorocyclopentyl)-3-oxopiperazin-1-yl]carbonyl}-4-fluorobenzyl)-4,5-dimethyl-3-oxo-2,3-dihydropyridazin-1-ium trifluoroacetate | 462.5 | 463 |
| 50 | 6-(3-{[4-(4,4-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate | 468.6 | 469 |
| 51 | 6-(3-{[4-(3,3-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate | 468.6 | 469 |
| 52 | 6-{3-[(4-Bicyclo[1.1.1]pent-1-yl-3-oxopiperazin-1-yl)carbonyl]-4-fluorobenzyl}-4,5-dimethyl-3-oxo-2,3-dihydropyridazin-1-ium trifluoroacetate | 424.5 | 425 |
| 53 | 6-(4-Fluoro-3-{[3-oxo-4-(1,2,3,4-tetrahydronaphthalen-1-ylmethyl)piperazin-1-yl]carbonyl}benzyl)-4,5-dimethyl-3-oxo-2,3-dihydropyridazin-1-ium trifluoroacetate | 502.6 | 503 |
| 54 | 6-[4-Fluoro-3-({4-[1-(3-isopropyl-1,2,4-oxadiazol-5-yl)ethyl]-3-oxopiperazin-1-yl}carbonyl)benzyl]-4,5-dimethyl-3-oxo-2,3-dihydropyridazin-1-ium trifluoroacetate | 496.5 | 497 |
| 55 | 6-(3-{[4-(3,3-Difluorocyclobutyl)-3-oxopiperazin-1-yl]carbonyl}-4-fluorobenzyl)-4,5-dimethyl-3-oxo-2,3-dihydropyridazin-1-ium trifluoroacetate | 448.4 | 449 |
| 56 | 6-[4-Fluoro-3-({3-oxo-4-[(4-phenyltetrahydro-2H-pyran-4-yl)methyl]piperazin-1-yl}carbonyl)benzyl]-4,5-dimethyl-3-oxo-2,3-dihydropyridazin-1-ium trifluoroacetate | 532.6 | 533 |
| 57 | 6-{3-[(4-Cyclobutyl-3-oxopiperazin-1-yl)carbonyl]-4-fluorobenzyl}-4,5-dimethyl-3-oxo-2,3-dihydropyridazin-1-ium trifluoroacetate | 412.5 | 413 |
| 58 | 6-(4-Fluoro-3-{[4-(2-fluoroethyl)-3-oxopiperazin-1-yl]carbonyl}benzyl)-4,5-dimethyl-3-oxo-2,3-dihydropyridazin-1-ium trifluoroacetate | 404.4 | 405 |
| 59 | 6-[4-Fluoro-3-({4-[2-(3-fluorophenyl)ethyl]-3-oxopiperazin-1-yl}carbonyl)benzyl]-4,5-dimethyl-3-oxo-2,3-dihydropyridazin-1-ium trifluoroacetate | 480.5 | 481 |
| 60 | 6-{4-Fluoro-3-[(3-oxo-4-quinolin-3-ylpiperazin-1-yl)carbonyl]benzyl}-4,5-dimethylpyridazin-3(2H)-one | 485.5 | 486 |
| 61 | 3-[4-Fluoro-3-({3-oxo-4-[4-(trifluoromethyl)pyridin-2-yl]piperazin-1-yl}carbonyl)benzyl]-4,5-dimethyl-6-oxo-1,6-dihydropyridazin-1-ium trifluoroacetate | 503.5 | 504 |
| 62 | 3-(3-{[4-(1-Benzothien-3-yl)-3-oxopiperazin-1-yl]carbonyl}-4-fluorobenzyl)-4,5-dimethyl-6-oxo-1,6-dihydropyridazin-1-ium trifluoroacetate | 490.6 | 491 |
| 63 | 3-(4-Fluoro-3-{[3-oxo-4-(1,3-thiazol-5-yl)piperazin-1-yl]benzyl)-4,5-dimethyl-6-oxo-1,6-dihydropyridazin-1-ium trifluoroacetate | 441.5 | 442 |
| 64 | 3-{4-Fluoro-3-[(3-oxo-4-pyrimidin-5-ylpiperazin-1-yl)carbonyl]benzyl}-4,5-dimethyl-6-oxo-1,6-dihydropyridazin-1-ium trifluoroacetate | 436.4 | 437 |
| 65 | 3-[4-Fluoro-3-({3-oxo-4-[5-(trifluoromethyl)pyridin-3-yl]piperazin-1-yl}carbonyl)benzyl]-4,5-dimethyl-6-oxo-1,6-dihydropyridazin-1-ium trifluoroacetate | 503.5 | 504 |
| 66 | 6-(4-Fluoro-3-{[3-oxo-4-(3-phenylcyclohexyl)piperazin-1-yl]carbonyl}benzyl)-4,5-dimethyl-3-oxo-2,3-dihydropyridazin-1-ium trifluoroacetate | 516.6 | 517 |
| 67 | 6-[4-Fluoro-3-({3-oxo-4-[(1R,2S)-2-phenylcyclohexyl]piperazin-1-yl}carbonyl)benzyl]-4,5-dimethyl-3-oxo-2,3-dihydropyridazin-1-ium trifluoroacetate | 516.6 | 517 |
| 68 | 6-(4-Fluoro-3-{[3-oxo-4-(4-phenylcyclohexyl)piperazin-1-yl]carbonyl}benzyl)-4,5-dimethyl-3-oxo-2,3-dihydropyridazin-1-ium trifluoroacetate | 516.6 | 517 |
| 69 | 6-(4-Fluoro-3-{[3-oxo-4-(tetrahydrofuran-3-yl)piperazin-1-yl]carbonyl}benzyl)-4,5-dimethyl-3-oxo-2,3-dihydropyridazin-1-ium trifluoroacetate | 428.5 | 429 |
| 70 | 6-(4-Fluoro-3-{[3-oxo-4-(1,2,3,4-tetrahydronaphthalen-2-yl)piperazin-1-yl]carbonyl}benzyl)-4,5-dimethyl-3-oxo-2,3-dihydropyridazin-1-ium trifluoroacetate | 488.6 | 489 |
| 71 | 6-(3-{[4-(2,3-Dihydro-1H-inden-2-yl)-3-oxopiperazin-1-yl]carbonyl}-4-fluorobenzyl)-4,5-dimethyl-3-oxo-2,3-dihydropyridazin-1-ium trifluoroacetate | 474.5 | 475 |
| 72 | 6-(4-Fluoro-3-{[3-oxo-4-(2,2,2-trifluoroethyl)piperazin-1-yl]carbonyl}benzyl)-4,5-dimethyl-3-oxo-2,3-dihydropyridazin-1-ium trifluoroacetate | 440.4 | 441 |
| 73 | 6-{3-[(4-Cycloheptyl-3-oxopiperazin-1-yl)carbonyl]-4-fluorobenzyl}-4,5-dimethyl-3-oxo-2,3-dihydropyridazin-1-ium trifluoroacetate | 454.5 | 455 |
| 74 | 3-(4-Fluoro-3-{[4-(3-thienyl)piperazin-1-yl]carbonyl}benzyl)-4,5-dimethyl-6-oxo-1,6-dihydropyridazin-1-ium trifluoroacetate | 440.5 | 441 |

EXAMPLE 75

6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one and 6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one (II4A and II4B)

Step 1: N-(tert-Butoxycarbonyl)-N-{2-[(3R)-tetrahydrofuran-3-ylamino]propyl}glycine (II1)

To a solution (0.56 M) of (3S)-tetrahydrofuran-3-amine. HCl (prepared as described in *Helv. Chim. Acta* 2000, 83, 1825-1845) in DCE were added N-(tert-butoxycarbonyl)-N-(2-oxopropyl)glycine (1.3 eq), DIPEA (1 eq), NaBH(OAc)$_3$ (2 eq), cat. AcOH and cat. NaOAc. Reaction mixture was irradiated at MW for 20 min at 120° C. DCE was removed under reduced pressure and the residue purified by filtration on silica gel eluting of the desired intermediate with EtOAc. Evaporation of the organic solvent yielded (II1). MS (ES) $C_{14}H_{26}N_2O_5$ requires: 302, found: 303 (M+H)$^+$.

Step 2: tert-Butyl 3-methyl-5-oxo-4-[(3S)-tetrahydrofuran-3-yl]piperazine-1-carboxylate (II2)

The residue II1 was dissolved in DMF (0.56 M) and HATU (2.5 eq) and DIPEA (3 eq) were added. Reaction mixture was irradiated at MW for 10 min at 110°. The reaction mixture was diluted with EtOAc, washed sequentially with 1N HCl, sat. aq. NaHCO$_3$ solution, and brine. The organic layer was dried (Na$_2$SO$_4$) and the solvent was removed under reduced pressure affording (II2). MS (ES) $C_{14}H_{24}N_2O_4$ requires: 284, found: 285 (M+H)$^+$.

Step 3: 6-Methyl-1-[(3S)-tetrahydrofuran-3-yl]piperazin-2-one hydrochloride (II3)

Crude II2 was dissolved in EtOAc, then 4M HCl in dioxane was added. The mixture was stirred at RT for 30 min. After the removal of the solvent under reduced pressure, the crude was scratched with Et$_2$O and the solvent decanted to afford the title compound (II3). MS (ES) $C_9H_{17}ClN_2O_2$ requires: 184, found: 185 (M+H)$^+$.

Step 4: 6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one and 6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one (II4A and II4B)

A mixture of 5-[(4,5-dimethyl-6-oxo-1,6-dihydropyridazin-3-yl)methyl]-2-fluorobenzoic acid (Preparative Example 2) (1.1 eq), TBTU (1.1 eq) and DIPEA (2.1 eq) in DMF (0.204 M) was stirred at RT for 30 min then II3 (1 eq) was added and stirring was continued O/N at RT. The reaction mixture was diluted with EtOAc, washed sequentially with sat. aq. NaHCO$_3$ solution, 1N HCl, and brine. The solution was dried (Na$_2$SO$_4$), filtered and concentrated under reduced pressure. The crude product was purified by preparative RP-HPLC using H$_2$O (0.1% TFA) and MeCN (0.1% TFA) as eluents and the desired fractions were evaporated under reduced pressure to afford the title compound (DB4) as racemate. MS (ES) $C_{23}H_{27}FN_4O_4$ required: 442.5, found: 443 (M+H)$^+$ DB4 was separated by chiral SFC (column: Chiralcel OJ-H, 1×25 mm, flow: 10 ml/min, T$_{col}$: 35° C., P$_{col}$: 100 bar, modifier: 13% (MeOH 0.2% Et$_2$NH)), using CO$_2$ as supercritic eluent, affording both pure diastereomers.

(Diasteroisomer-A, II4A): 1$^{st}$ eluted on SFC system, retention time=7.21 min, was obtained as a white powder $^1$H-NMR (300 MHz, DMSO-d6, 300K) δ: 7.40-7.10 (3H, m), 4.60-4.20 (2H, m), 4.05-3.43 (9H, m), 3.34-3.16 (1H, d), 2.15-1.85 (9H, m), 1.16 (1.2H, d, J=6.34 Hz), 1.04 (1.8H, d, J=6.34 Hz). MS (ES) $C_{23}H_{27}FN_4O_4$ required: 442.5, found: 443 (M+H)$^+$.

(Diasteroisomer-B, II4B): 2$^{nd}$ eluted on SFC system, retention time=8.76 min, was obtained as a white powder: $^1$H-NMR (300 MHz, DMSO-d6, 300K) δ: 7.49-7.10 (3H, m), 4.70-4.25 (2H, m), 4.10-3.80 (4H, m), 3.78-3.40 (5H, m), 3.35-3.15 (1H, m), 2.15-1.75 (9H, m), 1.18 (1.2H, d, J=6.04 Hz), 1.02 (1.8H, d, J=6.04 Hz). MS (ES) $C_{23}H_{27}FN_4O_4$ required: 442.5, found: 443 (M+H)$^+$.

EXAMPLE 76

6-(3-{[4-(2,2-Dimethyltetrahydro-2H-pyran-4-yl)-3-oxopiperazin-1-yl]carbonyl}-4-fluorobenzyl)-4,5-dimethylpyridazin-3(2H)-one trifluoroacetate (JJ3)

Step 1: Methyl N-(2,2-diethoxyethyl)-N-{5-[(4,5-dimethyl-6-oxo-1,6-dihydropyridazin-3-yl)methyl]-2-fluorobenzoyl}glycinate (JJ1)

To a solution of 5-[(4,5-dimethyl-6-oxo-1,6-dihydropyridazin-3-yl)methyl]-2-fluorobenzoic acid (Preparative Example 2) (1 eq), TBTU (1.2 eq), and DIPEA (1.5 eq) in DMF (0.18M) was added methyl N-(2,2-diethoxyethyl)glycinate (1 eq) (prepared as described in *Synthesis* 2002, 2, 242-252), and the mixture was stirred at RT for 2 h. The reaction was diluted with EtOAc, washed sequentially with 1N HCl, sat. aq. NaHCO$_3$ solution, and then with brine. The organic layers were dried (Na$_2$SO$_4$), filtered and concentrated and concentrated under reduced pressure. MS (ES) $C_{23}H_{30}FN_3O_6$ required: 463, found: 464 (M+H)$^+$; 486 (M+Na)$^+$.

Step 2: N-{5-[(4,5-Dimethyl-6-oxo-1,6-dihydropyridazin-3-yl)methyl]-2-fluorobenzoyl}-N-(2-oxoethyl)glycine (JJ2)

To a 0.1M solution of intermediate JJ1 (1 eq) in THF/H$_2$O (1:1) was added LiOH (2 eq), and the reaction was stirred at RT for 1 h. The mixture was acidified with 1 N HCl and extracted with EtOAc, dried (Na$_2$SO$_4$), filtered and concentrated under reduced pressure. The residue was dissolved in CHCl$_3$ and added to a cooled 0.1 M solution of TFA (20 eq) in CHCl$_3$/H$_2$O (1:1). The reaction was stirred at 0° C. for 8 h, then the volatiles were removed and concentrated under reduced pressure to afford the desired material as an amber oil. MS (ES) $C_{18}H_{18}FN_3O_5$ required: 375, found 376 (M+H)$^+$.

Step 3: 6-(3-{[4-(2,2-Dimethyltetrahydro-2h-pyran-4-yl)-3-oxopiperazin-1-yl]carbonyl}-4-fluoro benzyl)-4,5-dimethylpyridazin-3(2H)-one trifluoroacetate (JJ3)

To a 0.4 M solution containing the intermediate JJ2 (1 eq) and 2,2-dimethyltetrahydro-2H-pyran-4-amine (1.5 eq) in MeOH, were added NaBH$_3$(CN) (1.5 eq) and catalytic AcOH. The reaction was heated in a MW apparatus (100° C., 7 min). After evaporation of the solvent the crude intermediate was dissolved in DMF, then HATU (2 eq) and DIPEA (2 eq) were added and the mixture heated in MW apparatus (120° C., 10 min). The crude product was purified by preparative RP-HPLC using H$_2$O (0.1% TFA) and MeCN (0.1% TFA) as eluents and the combined fractions were evaporated under reduced pressure to afford the title compound (JJ3).

$^1$H-NMR (300 MHz, DMSO-d6, 300K) δ: 12.65 (1H, bs), 7.36-7.14 (3H, m), 4.79-4.54 (1H, m), 4.20-4.10 (1H, m), 3.95 (2H, s), 3.86-3.50 (4H, m), 3.46-3.14 (3H, m), 1.99 (6H, s), 1.69-1.35 (4H, m) 1.22-1.10 (6H, m). MS (ES). $C_{25}H_{31}FN_4O_4$ required: 470, found 471 (M+H)+.

EXAMPLE 77

6-{3-[(3,3-Dimethyl-5-oxo-4-phenylpiperazin-1-yl)carbonyl]-4-fluorobenzyl}-4,5-dimethylpyridazin-3(2H)-one (KK6)

Step 1: 2-Methyl-$N^2$-phenyl-propane-1,2-diamine (KK1)

A solution of 2-Methyl-2-phenylamino-propionamide (1 eq) in dry THF (0.2 M) was added dropwise to a stirred ice-cooled suspension of LiAlH$_4$(6 eq) in dry THF (1.2 M) under N$_2$. Upon completion of the addition, the reaction mixture was refluxed for 24 h. The mixture was cooled to 0° C., quenched with water and filtered through Celite. The filtrate was concentrated under reduced pressure and partitioned between water and DCM. The organic phase was separated and washed with brine, then dried (Na$_2$SO$_4$) and concentrated under reduced pressure to yield KK1 as reddish oil which was used as such in the next step. MS (ES) $C_{10}H_{16}N_2$ requires: 164, found: 165 (M+H)+.

Step 2: (2-Methyl-2-phenylamino-propyl)-carbamic acid benzyl ester (KK2)

To a solution of KK1 (1 eq) and Et$_3$N (1.3 eq) in DCM (0.1 M) at 0° C. was added Cbz-Cl (1.3 eq) and the reaction mixture was stirred at RT overnight. The mixture was diluted with DCM and washed with sat. aq. NaHCO$_3$ solution and brine, dried (Na$_2$SO$_4$) and concentrated under reduced pressure. The obtained crude product was purified by column chromatography on silica gel, eluting with 5% EtOAc/Petroleum ether to afford the desired compound KK2. MS (ES) $C_{18}H_{22}N_2O_2$ requires: 298, found: 299 (M+H)+. $^1$H-NMR (400 MHz, CDCl$_3$, 300K) δ: 7.42-7.28 (5H, m), 7.17 (2H, t, J=7.4 Hz), 6.80 (1H, t, J=7.2 Hz), 6.72 (2H, d, J=7.6 Hz), 5.21 (1H, br. s), 5.12 (1H, s), 3.39 (2H, d, J=5.4 Hz), 1.29 (6H, s).

Step 3: {2-[(2-Bromo-acetyl)-phenyl-amino]-2-methyl-propyl}-carbamic acid benzyl ester (KK3)

To a solution of bromoacetylbromide (1.2 eq) in DCM (0.44 M) at −10° C. was added dropwise a solution of KK2 (1 eq) and Et$_3$N (1.2 eq) in DCM (0.44 M). The mixture was stirred at −10° C. for 30 min and then left stirring at RT overnight. The residue was partitioned between EtOAc and water, and then separated. The organic phase was dried (Na$_2$SO$_4$) and concentrated under reduced pressure. The crude product was purified by column chromatography on silica gel, eluting with a gradient of 5-15% EtOAc/Petroleum ether to afford the desired compound KK3.
MS (ES) $C_{20}H_{23}BrN_2O_3$ requires: 418/420 found: 419/421 (M+H)+.

Step 4: 3,3-Dimethyl-5-oxo-4-phenyl-piperazine-1-carboxylic acid benzyl ester (KK4)

A suspension of NaH (60 wt %, 3 eq) in DMF (0.6 M) was added dropwise to a solution of KK3 (1 eq) in DMF (0.2 M) at −10° C., and the mixture was stirred at RT overnight. The residue was partitioned between EtOAc and sat. aq. NaHCO$_3$ solution and separated. The organic phase was dried (Na$_2$SO$_4$), filtered and concentrated under reduced pressure. The obtained crude product was purified by preparative TLC, eluting with 1:1 Petroleum ether/EtOAc to afford the desired compound KK4. MS (ES) $C_{20}H_{22}N_2O_3$ requires: 338 found: 339 (M+H)+. $^1$H-NMR (300 MHz, CDCl$_3$, 300K) δ: 7.38 (8H, m), 7.13-7.05 (2H, m), 5.21 (2H, s), 4.35 (2H, s), 3.70 (2H, br. s), 1.23 (6H, m).

Step 5: 6,6-Dimethyl-1-phenyl-piperazin-2-one (KK5)

A suspension of KK4 and Pd/C (10%) in MeOH (0.1M) was stirred under H$_2$ atmosphere for 1 h. The catalyst was filtered off and the filtrate was concentrated under reduced pressure. The obtained crude product (KK5) was used as such in the next step. MS (ES) $C_{12}H_{16}N_2O$ requires: 204 found: 205 (M+H)+.

Step 6: 6-{3-[(3,3-dimethyl-5-oxo-4-phenylpiperazin-1-yl)carbonyl]-4-fluorobenzyl}-4,5-dimethyl pyridazin-3(2H)-one (KK6)

KK6 was prepared as described for Example 1 using Preparative Example 2 and KK5 (1.5 eq). The crude product was purified by preparative RP-HPLC using H$_2$O and MeCN in the absence of TFA as eluents. The desired fractions were lyophilized to afford the titled compound KK6 as a white solid. MS (ES) $C_{26}H_{27}FN_4O_3$ requires: 462, found: 463 (M+H)+. $^1$H-NMR (400 MHz, DMSO-d6, 300K) δ: 12.68 (1H, s), 7.50-7.19 (6H, m), 7.18-7.10 (2H, m), 4.36 (1H, br. s), 4.07-3.91 (4H, m), 3.54 (1H, m), 2.06-1.95 (6H, m), 1.19 (3H, s), 0.99 (3H, s).

EXAMPLE 78

3-[4-Fluoro-3-(3-methyl-5-oxo-4-phenyl-piperazine-1-carbonyl)-benzyl]-4,5-dimethyl-6-oxo-1,6-dihydro-pyridazin-1-ium trifluoroacetate (LL4), and the corresponding enantiomers 6-(4-fluoro-3-{[(3S)-3-methyl-5-oxo-4-phenylpiperazin-1-yl]carbonyl}benzyl)-4,5-dimethylpyridazin-3(2H)-one and 6-(4-fluoro-3-{[(3R)-3-methyl-5-oxo-4-phenylpiperazin-1-yl]carbonyl}benzyl)-4,5-dimethylpyridazin-3(2H)-one (LL4A and LL4B)

Step 1: [tert-Butoxycarbonyl-(2-phenylamino-propyl)-amino]-acetic acid (LL1)

A mixture of [tert-Butoxycarbonyl-(2-oxo-propyl)-amino]-acetic acid (1 eq), aniline (1.2 eq) and Ti(O$^i$Pr)$_4$(1.25 eq) was stirred at RT for 30 min under N$_2$ flow. The mixture was diluted with dry EtOH (0.8 M) and NaBH$_3$(CN) (0.67 eq) was added. The reaction mixture was stirred for 24 h, after which water was added and the resulting white, inorganic precipitate was filtered, and washed with EtOH. The filtrate was concentrated under reduced pressure and the resulting crude was diluted with EtOAc. The solution was extracted with 1N NaOH and the aqueous phase was washed with EtOAc twice. The aqueous phase was acidified to pH 1 by addition of conc. HCl at 0° C. and washed with EtOAc. The pH of the collected aqueous phase was adjusted to pH 3-4 and product extracted with EtOAc (5×). The collected organic phases were dried (Na$_2$SO$_4$), filtered and evaporated to provide LL1 as a transparent oil. MS (ES) $C_{16}H_{24}N_2O_4$ requires: 308 found: 309 (M+H)+.

Step 2: 3-Oxo-4-phenyl-piperazine-1-carboxylic acid tert-butyl ester (LL2)

HATU (1.2 eq) and DIPEA (1.2 eq) were added to a solution of LL1 in DMF (0.1 M), and the reaction mixture was stirred for 15 min at RT and then diluted with EtOAc. The organic phase was washed with 1N HCl (3×), 1N NaOH (3×) and brine. The organic phase was dried ($Na_2SO_4$), filtered and evaporated to provide a yellow oil. MS (ES) $C_{16}H_{22}N_2O_3$ requires: 290 found: 291 $(M+H)^+$. $^1H$-NMR (400 MHz, $CDCl_3$, 300K) δ: 7.43 (2H, m), 7.32 (1H, m), 7.20 (2H, d, J=7.2 Hz), 4.62-4.30 (1H, m), 4.18-4.05 (1H, m), 3.93 (1H, m), 3.85 (1H, d, J=13.7 Hz), 3.66 (1H, d, J=13.1 Hz), 1.51 (9H, s), 1.17 (3H, d, J=5.8 Hz).

Step 3: 3-methyl-5-oxo-4-phenyl-piperazin-1-ium trifluoroacetate (LL3)

A solution of LL2 (1 eq) in DCM/TFA (1:1, 0.1 M) was stirred at RT for 30 min and then concentrated under reduced pressure. The resulting crude was used as such in the next step without further purification. MS (ES) $C_{11}H_{14}N_2O$ requires: 190 found: 191 $(M+H)^+$.

Step 4: 3-[4-fluoro-3-(3-methyl-5-oxo-4-phenyl-piperazine-1-carbonyl)-benzyl]-4,5-dimethyl-6-oxo-1,6-dihydro-pyridazin-1-ium trifluoroacetate (LL4), and the corresponding diastereomers (LL4A and LL4B)

LL4 was prepared as described for Example 1 using Preparative Example 2 and LL3 (1.5 eq). The crude product was purified by preparative RP-HPLC using $H_2O$ (0.1% TFA) and MeCN (0.1% TFA) as eluents. The desired fractions were lyophilized to afford the titled compound LL4 as a white solid, as a mixture of diastereomers. $^1H$-NMR (400 MHz, DMSO-d6+TFA, 300K) (mixture of diastereoisomers with a ratio: 0.6:0.4). δ: 12.68 (1H, br. s), 7.43 (2H, m), 7.38-7.21 (6H, m), 4.60 (0.6H, d, J=18.2 Hz), 4.26 (0.4H, d, J=13.1 Hz), 4.17-3.76 (5.4H, m), 3.42 (0.6H, d, J=12.8 Hz), 2.08-1.94 (6H, m), 1.08 (1.2H, d, J=5.6 Hz), 0.91 (1.8H, d, J=5.5 Hz). MS (ES) $C_{25}H_{25}FN_4O_3$ requires: 448, found: 449 $(M+H)^+$.

The mixture LL4 was separated by chiral SFC (column: chiralpak AS-H (1×25 cm)), flow: 10 ml/min, Tcol: 35° C., Pcol: 100 bar, modifier: 50% (MeOH, 0.2% $Et_2NH$)), using $CO_2$ as supercritic eluent, affording both pure diastereomers.

(Enantiomer-A, LL4A): $1^{st}$ eluted on SFC system, retention time (SFC)=3.5 min; was obtained as white powder (Enantiomer-B, LL4B): $2^{nd}$ eluted on SFC system, retention time (SFC)=4.9 min; was obtained as white powder

EXAMPLE 79

3-{4-Fluoro-3-[4-(4-fluoro-phenyl)-3-methyl-5-oxo-piperazine-1-carbonyl]-benzyl}-4,5-dimethyl-6-oxo-1,6-dihydro-pyridazin-1-ium trifluoroacetate (MM4), and the corresponding enantiomers: 6-(4-fluoro-3-{[(3S)-4-(4-fluorophenyl)-3-methyl-5-oxopiperazin-1-yl]carbonyl}benzyl)-4,5-dimethylpyridazin-3(2H)-one and 6-(4-fluoro-3-{[(3R)-4-(4-fluorophenyl)-3-methyl-5-oxopiperazin-1-yl]carbonyl}benzyl)-4,5-dimethylpyridazin-3(2H)-one (MM4A and MM4B)

Step 1: {tert-Butoxycarbonyl-[2-(4-fluoro-phenylamino)-propyl]-amino}-acetic acid (MM1)

MM1 was prepared following the one described in Preparative Example 78, step 1 starting from (MM1) and 4-fluorophenylamine. MS (ES) $C_{16}H_{23}FN_2O_4$ requires: 326; found: 327 $(M+H)^+$.

Step 2: 4-(4-Fluorophenyl)-3-methyl-5-oxo-piperazine-1-carboxylic acid tert-butyl ester (MM2)

ZZ2 was prepared following the one described in Preparative Example 78, step 2 starting from MM1. MS (ES) $C_{16}H_{21}FN_2O_3$ requires: 308; found: 309 $(M+H)^+$. $^1H$-NMR (300 MHz, $CDCl_3$, 300K) δ: 7.21-7.06 (4H, m), 4.55-4.28 (1H, m), 4.06 (1H, m), 3.95-3.78 (2H, m), 3.69 (1H, dd, $J_1$=13.4 Hz, $J_2$=3.5 Hz), 1.50 (9H, s), 1.16 (3H, d, J=6.4 Hz).

Step 3: 4-(4-Fluorophenyl)-3-methyl-5-oxo-piperazin-1-ium trifluoroacetate (MM3)

MM3 was prepared following the one described in Preparative Example 78, step 3 starting from MM2. MS (ES) $C_{11}H_{13}FN_2O$ requires: 208; found: 209 $(M+H)^+$.

Step 4: 3-{4-Fluoro-3-[4-(4-fluorophenyl)-3-methyl-5-oxo-piperazine-1-carbonyl]-benzyl}-4,5-dimethyl-6-oxo-1,6-dihydro-pyridazin-1-ium trifluoroacetate (MM4), and the corresponding diastereomers (MM4A and MM4B)

MM4 was prepared as described for Example 1 using Preparative Example 2 and MM3 (1.5 eq). The crude product was purified by preparative RP-HPLC using $H_2O$ (0.1% TFA) and MeCN (0.1% TFA) as eluents. The desired fractions were lyophilized to afford the titled compound MM4 as a white solid, as a mixture of diastereomers. MS (ES) $C_{25}H_{24}F_2N_4O_3$ requires: 466, found: 467 $(M+H)^+$. $^1H$-NMR (400 MHz, DMSO-d6+TFA, 300K) (mixture of diastereoisomers: 0.6: 0.4) δ: 12.68 (1H, br. s), 7.40-7.19 (7H, m), 4.57 (0.6H, d, J=18.4 Hz), 4.28-3.75 (5.8H, m), 3.41 (0.6H, d, J=10.9 Hz), 2.00 (6H, m), 1.07 (1.2H, d, J=6.2 Hz), 0.90 (1.8H, d, J=6.1 Hz). The mixture MM4 was separated by chiral SFC (column: chiralpak AS-H (1×25 cm)), flow: 10 ml/min, Tcol: 35° C., Pcol: 100 bar, modifier: 45% (MeOH 0.2% $Et_2NH$)), using $CO_2$ as supercritical eluent, affording both pure diastereomers.

(Enantiomer-A, MM4A): $1^{st}$ eluted on SFC system, retention time (SFC)=3.49 min was obtained as white powder (Enantiomer-B, MM4B): $2^{nd}$ eluted on SFC system, retention time (SFC)=4.77 min was obtained as white powder

EXAMPLE 80 cis-3-{4-Fluoro-3-[4-(3-fluoro-cyclopentyl)-3-oxo-piperazine-1-carbonyl]-benzyl}-4,5-dimethyl-6-oxo-1,6-dihydro-pyridazin-1-ium trifluoroacetate (NN4)

Step 1: cis-3-Fluorocyclopentanaminium trifluoroacetate (NN1)

To a solution of (3-hydroxycyclopentyl)-carbamic acid tert-butyl ester (prepared as described in Tetrahedron 1999, 55, 10815-10834) (1 eq) in DCM (1 M) at −10° C. was added [bis(2-methoxyethyl)amino]sulfur trifluoride (1 eq). The reaction mixture was stirred at −10° C. for 15 min, then the reaction mixture was diluted with DCM, washed with sat. aq. $NaHCO_3$ solution, and back-extracted with DCM (3×). The collected organic phases were dried ($Na_2SO_4$), and evaporated under reduced pressure. The crude product was purified by column chromatography on silica gel to afford tert-butyl cis-3-fluorocyclopentylcarbamate, MS (ES) $C_{10}H_{18}FNO_2$ requires: 203 found: 204 $(M+H)^+$. A solution of this intermediate in DCM/TFA (1:1, 0.24 M) was stirred at RT for 30 min and then concentrated under reduced pressure. The resulting crude was used as such in the next step without further purification. MS (ES) $C_5H_{10}FN$ requires: 103 found: 104 $(M+H)^+$.

Step 2: cis Benzyl 4-[3-fluorocyclopentyl]-3-oxopiperazine-1-carboxylate (NN2)

NN2 was prepared starting from NN1 and methyl N-[(benzyloxy)carbonyl]-N-(2,2-diethoxyethyl)glycinate, (prepared as described in *Synthesis* 2002, 2, 242-252), according to the procedure described in Example 75, steps 2 and 3. MS (ES) $C_{17}H_{21}FN_2O_3$ requires: 320 found: 321 $(M+H)^+$.

Step 3: c is 4-[3-Fluorocyclopentyl]-3-oxopiperazin-1-ium chloride (NN3)

A stirred solution of NN2 (1 eq) and Pd/C (10% w/w, 0.3 eq) in MeOH (0.1 M) was hydrogenated under an $H_2$ in presence of 6 M HCl (1 eq). After 16 h the catalyst was filtered off and volatiles were removed under reduced pressure. The resulting crude was again dissolved in MeOH (0.1 M) and new Pd/C catalyst (10% w/w, 0.3 eq) and 6 M HCl (1 eq) was added, and the reaction was hydrogenated for further 2 h. Then the catalyst was filtered off and volatiles evaporated, the resulting crude was used as such in the next step. MS (ES) $C_9H_{16}FN_2O$ requires: 187 found: 188 $(M+H)^+$.

Step 4: cis-3-{4-Fluoro-3-[4-(3-fluoro-cyclopentyl)-3-oxo-piperazine-1-carbonyl]-benzyl}-4,5-dimethyl-6-oxo-1,6-dihydro-pyridazin-1-ium trifluoroacetate (NN4)

NN4 was prepared as described for Example 1 using Preparative Example 2 and NN3 (1.5 eq). The crude product was purified by preparative RP-HPLC using $H_2O$ (0.1% TFA) and MeCN (0.1% TFA) as eluents. The desired fractions were lyophilized to afford the titled compound VV4 as a white solid. MS (ES) $C_{23}H_{26}F_2N_4O_3$ requires: 444, found: 445 (M+H). $^1$H-NMR (400 MHz, DMSO-d6, 300K) δ: 12.67 (1H, s), 7.37-7.21 (3H, m), 5.19 (0.5H, br. s), 5.09-4.86 (1.5H, m), 4.17 (1.25H, m), 3.97 (2H, s), 3.92-3.75 (1.5H, m), 3.46 (1H, m), 3.37 (0.75H, m), 3.25 (1.5H, m), 2.28-2.10 (1H, m), 2.05-1.95 (6H, m), 1.94-1.86 (1H, m), 1.80-1.58 (4H, m).

EXAMPLE 81

6-{3-[(4-Cyclopentyl-3-oxopiperazin-1-yl)carbonyl]-4-fluorobenzyl}-4-(pentafluoroethyl)pyridazin-3(2H)-one (OO8)

Step 1: Ethyl 3-cyano-4,4,5,5,5-pentafluoro-3-hydroxypentanoate (OO1)

A solution of KCN (1.4 eq.) in water (0.5 M) was added with stirring to an ice-cooled solution of ethyl 4,4,5,5,5-pentafluoro-3-oxopentanoate (1 eq.) in EtOH and water (40:60 vol). The mixture was stirred for 6 h at 0° C. and then acidified with 6N sulphuric acid and extracted with $Et_2O$. The organic phase was dried ($Na_2SO_4$), and the solvents were removed under reduced pressure. The residue was vacuum distilled. The product fraction was collected at 74-76° C./0.5 mbar. (400 MHz, $CDCl_3$) δ: 5.88 (1H, s), 4.40-4.23 (2H, m), 3.04 (1H, s), 1.33 (3H, t, J=7.1 Hz).

Step 2: 2-Hydroxy-2-(pentafluoroethyl)succinic acid (OO2)

A mixture of OO1 and conc. sulfuric acid (5.2 eq.) were stirred and heated to 110° C. for 1 h. After cooling to RT water was added and the mixture was extracted with $Et_2O$. The organic phase was concentrated under reduced pressure and 6 N sulfuric acid (17 eq.) was added. The mixture was stirred and heated to reflux for 17 h. After cooling to RT the mixture was extracted with $Et_2O$, dried ($Na_2SO_4$) and the solvent was removed under reduced pressure to afford the title compound as a light brown oil. MS (ES) $C_6H_5F_5O_5$ requires: 252, found: 251 $(M-H)^-$.

Step 3: Pentafluoroethyl maleic anhydride (OO3)

A mixture of OO2 and $P_2O_{10}$ were heated to 170° C. for 80 min, the formed product was distilled from the mixture under reduced pressure (b.p. 85° C. at 50 mbar) and obtained as a colourless solid. $^1$H-NMR (300 MHz, $CDCl_3$) δ: 7.37 (1H, s), $^{19}$F-NMR (300 MHz, $CDCl_3$) δ: −83.3 (3F, s), −115.4 (2F, s).

Step 4: 6-Chloro-3-methoxy-4-(pentafluoroethyl) pyridazine (OO5a) and 3-chloro-6-methoxy-4-(pentafluoroethyl)pyridazine (OO5b)

To a solution of 3,6-dichloro-4-(pentafluoroethyl)pyridazine (OO4) (obtained from OO3, following the procedure described for Preparative Example 3 for C4) in anhydrous MeOH (0.35 M) at 0° C. was added NaOMe (1.2 eq.). The cooling bath was removed and the mixture was stirred at RT for 40 min. The mixture was diluted with EtOAc, washed with water, dried ($Na_2SO_4$) and the solvent was evaporated under reduced pressure. The residue was purified by column chromatography on silica gel, eluting with $Et_2O$/petroleum ether to give the mixture of the title compounds as a colorless oil (ca. 1:3, 5a:5b). $^1$H-NMR (300 MHz, $CDCl_3$) δ: OO5a:7.59 (1H, s), 4.23 (3H, s), OO5b: 7.26 (1H, s), 4.21 (3H, s).

Step 5: Methyl 2-fluoro-5-{[6-methoxy-5-(pentafluoroethyl)pyridazin-3-yl]methyl}benzoate (OO6a) and methyl 2-fluoro-5-{[6-methoxy-4-(pentafluoroethyl)pyridazin-3-yl]methyl}benzoate (OO6b)

A mixture of Pd(OAc)$_2$ (0.2 eq.) and dicyclohexyl(2',4',6'-triisopropylbiphenyl-2-yl)phosphine (0.4 eq.) was stirred in degassed THF (0.4 M) under argon atmosphere at RT for 30 min. The catalyst THF solution was added to the mixture of OO5a/b (1 eq.), methyl 2-fluoro-5-[(4,4,5,5-tetramethyl-1,3,2-dioxaborolan-2-yl)methyl]benzoate (1.1 eq., prepared from methyl 5-(bromomethyl)-2-fluorobenzoate according to literature *Tetrahedron Lett.* 2002, 44, 233-235) and $K_2CO_3$ (4 eq.) under argon. Degassed water (20% vol of THF) was added and the mixture is warmed to 50-56° C. for 20 h. After cooling to RT the mixture was partitioned between EtOAc and sat. aq. NaHCO$_3$. The organic phase was separated, dried ($Na_2SO_4$), and concentrated to under reduced pressure to afford a dark green oil. The two isomeric products were isolated by column chromatography on silica gel, eluting with 3-25% EtOAc/petroleum ether to give the separated products as dark oils.

OO6a: $^1$H-NMR (300 MHz, $CDCl_3$) δ: 7.85-7.75 (1H, m), 7.42-7.39 (1H, m), 7.38 (1H, s), 7.10-7.00 (1H, m), 4.34 (2H, s), 4.22 (3H, s), 3.92 (3H, s), $^{19}$F-NMR (300 MHz, $CDCl_3$) δ: −83.3 (3F, s), −111.9 (1F, s), −115.6 (2F, s), MS (ES) $C_{16}H_{12}F_6N_2O_3$ requires: 394, found: 395 $(M+H)^+$.

OO6b: $^1$H-NMR (300 MHz, CDCl$_3$) δ: 7.85-7.72 (1H, m), 7.45-7.35 (1H, m), 7.12 (1H, s), 7.08-7.00 (1H, m), 4.37 (2H, s), 4.17 (3H, s), 3.88 (3H, s), $^{19}$F-NMR (300 MHz, CDCl$_3$) δ: −83.5 (3F, s), −112.5 (2F, s), −112.8 (1F, s), MS (ES) C$_{16}$H$_{12}$F$_6$N$_2$O$_3$ requires: 394, found: 395 (M+H)$^+$.

Step 6: 2-Fluoro-5-{[6-oxo-5-(pentafluoroethyl)-1,6-dihydropyridazin-3-yl]methyl}benzoic acid (OO7)

OO6a was heated in a 1:1-mixture of 1,4-dioxane and 6N HCl for 20 min to 120° C. in a microwave oven. After cooling to RT the solvents were removed under reduced pressure and the residue was partitioned between EtOAc and water. The organic phase was dried (Na$_2$SO$_4$), and concentrated under reduced pressure. The title compound was obtained as colourless oil. MS (ES) C$_{14}$H$_8$F$_6$N$_2$O$_3$ requires: 366, found: 367 (M+H)$^+$.

Step 7: 6-{3-[(4-Cyclopentyl-3-oxopiperazin-1-yl)carbonyl]-4-fluorobenzyl}-3-oxo-4-(pentafluoroethyl)-2,3-dihydropyridazin-1-ium trifluoroacetate (OO8)

OO7, 4-cyclopentyl-3-oxopiperazin-1-ium trifluoroacetate (1 eq.), TBTU (1 eq.) and N-methyl-morpholine (2.2 eq.) were stirred for 2 h in DMF. The product was purified by preparative HPLC (water/MeCN, 0.1% TFA as eluents) and desired pooled product fractions were lyophilized to afford a white powder. The powder was dissolved in DCM and washed with sat. aq. NaHCO$_3$. The organic phase was dried (Na$_2$SO$_4$), filtered and concentrated to dryness to afford the product as colourless oil. $^1$H-NMR (300 MHz, DMSO-d6) δ: 13.52 (1H, s), 7.90 (1H, s), 7.46-7.22 (3H, m), 4.82-4.65 (1H, m), 4.15 (1H, s), 4.03 (2H, s), 3.80 (2H, s), 3.42-3.20 (3H, m), 1.80-1.40 (8H, m). MS (ES) C$_{23}$H$_{22}$F$_6$N$_4$O$_3$ requires: 516, found: 517 (M+H)$^+$.

EXAMPLE 82

1-Cyclopropyl-4-{5-[(4,5-dimethyl-6-oxo-1,6-dihydropyridazin-3-yl)methyl]-2-fluorobenzoyl}-1,4-diazepan-2-one (PP2)

Step 1: Benzyl 4-cyclopropyl-3-oxo-1,4-diazepane-1-carboxylate (PP1)

A mixture of benzyl 3-oxo-1,4-diazepane-1-carboxylate (prepared according to *Polish J. Chem.* 1989, 63, 265-71), cyclopropylboronic acid (6 eq.), Et$_3$N (10 eq.), pyridine (16 eq.) and Cu(OAc)$_2$ (4 eq.) in dry THF (0.24 M) was heated for 10 min. to 140° C. in a microwave oven. After cooling to RT the mixture was filtered through celite, the solvents were removed under reduced pressure and the product was purified by chromatography on silica gel, eluenting with EtOAc/petroleum ether. The product was obtained as a white solid. $^1$H-NMR (300 MHz, CDCl$_3$) δ: 7.45-7.22 (5H, m), 5.15 (2H, s), 4.22-4.07 (2H, m), 3.70-3.37 (4H, m), 2.75-2.60 (1H, m), 1.90-1.65 (2H, m), 0.85-0.72 (2H, m), 0.60-0.41 (2H, m). MS (ES) C$_{16}$H$_{20}$N$_2$O$_3$ requires: 288, found: 289 (M+H)$^+$.

Step 2: 1-Cyclopropyl-4-{5-[(4,5-dimethyl-6-oxo-1,6-dihydropyridazin-3-yl)methyl]-2-fluorobenzoyl}-1,4-diazepan-2-one (PP2)

PP1 was dissolved in THF (0.01 M), Pd on carbon was added and the mixture was stirred for 4 h at RT under an H$_2$ atmosphere. The catalyst was filtered off and the solvent was removed under reduced pressure. The crude product was obtained as a colourless oil and used without further purification.

A mixture of Preparative Example 2, TBTU (1.3 eq.) and DIPEA (1.3 eq.) in DMF (0.03M) was stirred at RT for 30 min, and then the above intermediate was added and stirring was continued for 3 h at RT. The mixture was diluted with EtOAc, washed with sat. aq. NaHCO$_3$, 1N HCl, brine, dried (Na$_2$SO$_4$), and concentrated to dryness under reduced pressure. The product was purified by preparative HPLC (water/MeCN, 0.1% TFA as eluents) and pooled product fractions were lyophilized to afford the product as a white powder. $^1$H-NMR (400 MHz, DMSO-d6) δ: 12.73 (1H, s), 7.36-7.20 (2H, m), 7.18-7.02 (1H, m), 4.35 (1H, s), 4.06-3.95 (3H, m), 3.55-3.35 (4H, m), 2.74-2.57 (1H, m), 2.06 (6H, s), 1.88-1.60 (2H, m), 0.80-0.65 (2H, m), 0.60-0.48 (2H, m). MS (ES) C$_{22}$H$_{25}$FN$_4$O$_3$ requires: 412, found: 413 (M+H)$^+$.

EXAMPLE 83

6-{2-Bromo-5-[(4-cyclopentyl-3-oxopiperazin-1-yl)carbonyl]-4-fluorobenzyl}-4,5-dimethylpyridazin-3(2H)-one (QQ3)

Step 1: 4-Bromo-5-(cyanomethyl)-2-fluorobenzonitrile (QQ1)

A mixture of 4-bromo-2-fluoro-5-methylbenzonitrile, AIBN (0.1 eq.) and NBS (1 eq.) in CCl$_4$ (0.14 M) was stirred at 80° C. for 18 h. After cooling to RT the mixture was quenched with 1N aq. NaS$_2$O$_3$ and extracted with DCM. The organic phase was washed with brine, dried (Na$_2$SO$_4$), and concentrated to dryness under reduced pressure. The residue was dissolved in MeCN (0.2 M), then trimethylsilyl cyanide (1 eq.) was added, followed by TBAF (1M in THF, 1 eq.). The mixture was stirred for 2 h at RT, and then water was added and the solvents were removed under reduced pressure. The residue was diluted with DCM, washed with brine, dried (Na$_2$SO$_4$), and concentrated to dryness under reduced pressure. The crude product was purified by column chromatography on silica gel eluting with 5-50% EtOAc/petroleum ether to afford the product as a white solid. $^1$H-NMR (300 MHz, CDCl$_3$) δ: 7.78 (1H, d, J=6.3 Hz), 7.55 (1H, d, J=7.8 Hz), 3.82 (2H, s). MS (ES) C$_9$H$_4$BrFN$_2$ requires: 238/240, found: 237/239 (M−H)$^-$.

Step 2: 6-{2-Bromo-5-[(4-cyclopentyl-3-oxopiperazin-1-yl)carbonyl]-4-fluorobenzyl}-4,5-dimethyl pyridazin-3(2H)-one (QQ2)

The title compound was prepared following the procedures described for Preparative Example 3, and Example 1 starting from QQ1, and 3,6-dichloro-4,5-dimethylpyridazine. $^1$H-NMR (400 MHz, CDCl$_3$) δ: 10.90 (1H, bs), 7.39 (1H, d, J=8.8 Hz), 7.13 (1H, d, J=6.4 Hz), 4.89 (1H, s), 4.03 (2H, s), 4.00-3.80 (3H, m), 3.65-3.15 (3H, m), 2.17 (3H, s), 2.10 (3H, s), 1.95-1.35 (8H, m). MS (ES) C$_{23}$H$_{26}$BrFN$_4$O$_3$ requires: 504/506, found: 505/507 (M+H)$^+$.

EXAMPLE 84

6-{4-Fluoro-3-[(6-oxohexahydropyrazino[2,1-c][1,4]oxazin-8(1H)-yl)carbonyl]benzyl}-4,5-dimethyl-3-oxo-2,3-dihydropyridazin-1-ium trifluoroacetate (RR7)

Step 1: tert-Butyl 3-(aminomethyl)morpholine-4-carboxylate (RR1)

To a solution (0.3 M) of tert-butyl 3-cyano-4-morpholinecarboxylate (prepared as described in the *J. Med. Chem.* 2007, 50, 4953-4975) in MeOH was added $PtO_2$ (0.1 eq) and the mixture was stirred O/N under an $H_2$ atmosphere at 50 psi. The reaction mixture was filtered and concentrated under reduced pressure to afford the title compound RR1. MS (ES) $C_{10}H_{20}N_2O_3$ required: 216, found: 217 $(M+H)^+$.

Step 2: tert-Butyl 3-({[(benzyloxy)carbonyl]amino}methyl)morpholine-4-carboxylate (RR2)

A solution (0.15 M) of Cbz-Cl (1.7 eq) in DCM was added dropwise to an ice cold-solution (0.15 M) of RR1 (1 eq) and $Et_3N$ (1.8 eq) in DCM and the mixture was stirred at RT for 2 h. The solvent was evaporated under reduced pressure and the crude product was purified by column chromatography on silica gel, eluting with 10-30% EtOAc/Petroleum ether to afford the title compound RR2. $^1$H-NMR (300 MHz, DMSO-$d_6$, 300K) δ: 7.33 (5H, br. s), 4.99 (2H, s), 4.10-3.89 (1H, m), 3.78-3.55 (3H, m), 3.45-3.00 (6H, m), 1.37 (9H, s). MS (ES) $C_{18}H_{26}N_2O_5$ required: 350, found: 373 $(M+Na)^+$.

Step 3: Benzyl (morpholin-3-ylmethyl)carbamate (RR3)

Intermediate RR2 was solved in TFA/DCM (1:1, 0.2 M) and the mixture was stirred at RT for 2 h. The solvent was removed under reduced pressure and the crude product RR3 isolated as the free base by using an Isolute SCX cartridge. MS (ES) $C_{13}H_{18}N_2O_3$ required: 250, found: 251 $(M+H)^+$.

Step 4: Benzyl {[4-(chloroacetyl)morpholin-3-yl]methyl}carbamate (RR4)

$Et_3N$ (1.2 eq) and chloroacetyl chloride (1.2 eq) were added to an ice cold-solution of RR3 in THF (0.1 M) and the mixture was stirred at 0° C. for 3 h. The reaction mixture was diluted with EtOAc, washed sequentially with sat. aq. $NaHCO_3$ solution and brine. The solution was dried ($NaSO_4$), filtered and concentrated under reduced pressure to afford the desired compound RR4. MS (ES) $C_{15}H_{19}ClN_2O_4$ required: 326, found: 327 $(M+H)^+$.

Step 5: Benzyl 6-oxohexahydropyrazino[2,1-c][1,4]oxazine-8(1H)-carboxylate (RR5)

RR5 was prepared following the procedure described in Example 34, step 3. The crude product was purified by column chromatography on silica gel, eluting with PE-EtOAc (0-50% EtOAc) to afford the desired compound RR5. $^1$H-NMR (300 MHz, DMSO-$d_6$, 400K) δ: 7.35 (5H, br. s), 5.15 (2H, s), 4.50-4.38 (2H, m), 4.02-3.80 (3H, m), 3.71-3.60 (1H, m), 3.46 (1H, t, J=11.30), 3.17 (1H, t, J=11.30), 3.08-2.78 (3H, m). MS (ES) $C_{15}H_{18}N_2O_4$ required: 290, found: 291 $(M+H)^+$.

Step 6: Hexahydropyrazino[2,1-c][1,4]oxazin-6(1H)-one (RR6)

To a solution (0.15 M) of RR5 (1 eq) in MeOH was added 10% Pd/C (0.2 eq) and the mixture was stirred for 3 h under an $H_2$ atmosphere. The reaction mixture was filtered and concentrated at reduced pressure to afford the desired compound RR6 (pale yellow oil). MS (ES) $C_7H_{12}N_2O_2$ required: 156, found: 157 $(M+H)^+$.

Step 7: 6-{4-Fluoro-3-[(6-oxohexahydropyrazino[2,1-c][1,4]oxazin-8(1H)-yl)carbonyl]benzyl}-4,5-dimethyl-3-oxo-2,3-dihydropyridazin-1-ium trifluoroacetate (RR7)

RR7 was prepared as described for example 1 using RR6 (1 eq). The crude product was purified by preparative RP-HPLC using $H_2O$ (0.1% TFA) and MeCN (0.1% TFA) as eluents. The desired fractions were lyophilized to afford the titled compound RR7 (white solid). $^1$H-NMR (400 MHz, DMSO-$d_6$, 300K) δ: 12.66 (1H, s), 7.37-7.20 (3H, m), 4.58-4.46 (1H, m), 4.33-4.14 (1H, m), 4.01-3.46 (7H, m), 3.36-2.93 (3H, m), 2.83-2.59 (1H, m), 1.99 (6H, s). MS (ES) $C_{21}H_{23}FN_4O_4$ required: 414, found: 415 $(M+H)^+$.

EXAMPLE 85

6-{4-Fluoro-3-[(cis-6-methyl-4-oxooctahydro-2H-pyrido[1,2-a]pyrazin-2-yl)carbonyl]benzyl}-4,5-dimethyl-3-oxo-2,3-dihydropyridazin-1-ium trifluoroacetate (SS6)

Step 1: 1-(cis-6-Methylpiperidin-2-yl)methanamine (SS1)

To a solution (4.0 M) of 6-methyl-2-pyridinecarbonitrile in TFA was added $PtO_2$ (0.1 eq) and the mixture was stirred for 50 h under $H_2$ atmosphere at 50 psi. The reaction mixture was filtered and concentrated at reduced pressure to afford the title compound SS1. MS (ES) $C_7H_{16}N_2$ required: 128, found: 129 $(M+H)^+$.

Step 2: tert-Butyl[(cis-6-methylpiperidin-2-yl)methyl]carbamate (SS2)

To a solution of SS1 (1.2 eq) in DCM (0.4 M) was added $Et_3N$ until pH 8 and the solution was cooled at −78° C., then $Boc_2O$ (1 eq) in DCM was added dropwise and the mixture was stirred for 4 h at −78° C. and O/N at RT. The reaction mixture was diluted with EtOAc, washed sequentially with sat. aq. $NaHCO_3$ solution and brine. The organic phase was dried ($Na_2SO_4$), filtered and concentrated under reduced pressure. The crude product was purified by column chromatography on silica gel, eluting with PE-EtOAc (1:9) to afford the desired compound SS2.

$^1$H-NMR (300 MHz, DMSO-$d_6$, 300K) δ: 6.78 (1H, br. s), 2.98-2.78 (2H, m), 2.64-2.50 (3H, m), 1.74-1.63 (1H, m), 1.56-1.48 (2H, m), 1.31 (9H, m), 1.30-1.09 (1H, m), 0.99 (3H, J=6.0), 1.0-0.9 (2H, m). MS (ES) $C_{12}H_{24}N_2O_2$ required: 228, found: 229 $(M+H)^+$.

Step 3: tert-Butyl {[1-(bromoacetyl)-cis-6-methylpiperidin-2-yl]methyl}carbamate (SS3)

SS3 was prepared following the procedure described in Example 84, step 4, using bromoacetyl bromide instead of chloroacetyl chloride. The crude product was purified by column chromatography on silica gel, eluting with PE-EtOAc (1:9) to afford the desired compound SS3.

MS (ES) $C_{15}H_{25}BrN_2O_3$ required: 349, found: 350 (M+H)$^+$.

Step 4: tert-Butyl cis-6-methyl-4-oxooctahydro-2H-pyrido[1,2-a]pyrazine-2-carboxylate (SS4)

SS4 was prepared following the procedure described in Example 34, step 4. MS (ES) $C_{14}H_{24}N_2O_3$ required: 268, found: 269 (M+H)$^+$.

Step 5: cis-6-Methyloctahydro-4H-pyrido[1,2-a]pyrazin-4-one (SS5)

SS5 was prepared following the procedure described in preparative example 9, step 2. The desired compound was isolated as racemic mixture of cis-diastereomers (pale yellow oil). $^1$H-NMR (400 MHz, DMSO-d$_6$, 300K) δ: 4.05-3.97 (1H, m), 3.54-3.45 (1H, m), 3.19 (2H, br s), 2.95-2.87 (1H, m), 2.37-2.28 (1H, m), 1.90-1.36 (7H, m), 1.18 (3H, d, J=6.3). MS (ES) $C_9H_{16}N_2O$ required: 168, found: 169 (M+H)$^+$.

Step 6: 6-{4-Fluoro-3-[(cis-6-methyl-4-oxooctahydro-2H-pyrido[1,2-a]pyrazin-2-yl)carbonyl]benzyl}-4,5-dimethyl-3-oxo-2,3-dihydropyridazin-1-ium trifluoroacetate (SS6)

SS6 was prepared as described for example 1 using 6-methyloctahydro-4H-pyrido[1,2-a]pyrazin-4-one (1 eq). The crude product was purified by preparative RP-HPLC using H$_2$O (0.1% TFA) and MeCN (0.1% TFA) as eluents. The desired fractions were lyophilized to afford the titled compound SS6 (white solid) as racemic mixture of cis-diastereomers. $^1$H-NMR (400 MHz, DMSO-d$_6$, 300K) δ: 12.66 (1H, s), 7.40-7.16 (3H, m), 4.53-4.23 (1H, m), 4.10-3.79 (4H, m), 3.75-3.33 (2H, m), 3.17-2.92 (1H, m), 1.99 (6H, s), 1.93-1.26 (6H, m), 1.21 (3H, d, J=6.5). MS (ES) $C_{23}H_{27}FN_4O_3$ required: 426, found: 427 (M+H)$^+$.

EXAMPLE 86

(6S,9aS)-2-{5-[(4,5-Dimethyl-6-oxo-1,6-dihydropyridazin-3-yl)methyl]-2-fluorobenzoyl}-6-methyloctahydro-4H-pyrido[1,2-a]pyrazin-4-one and (6R,9aR)-2-{5-[(4,5-Dimethyl-6-oxo-1,6-dihydropyridazin-3-yl)methyl]-2-fluorobenzoyl}-6-methyloctahydro-4H-pyrido[1,2-a]pyrazin-4-one (TT1 and TT2)

The chiral separation of compound SS6 (Example 85, step 6) was performed by critical SFC (column: chiralpak IB (1×25 cm)), flow: 10 ml/min, Tcol: 35° C., Pcol: 100 bar, modifier: 60% (i-PrOH 0.4% Et$_2$NH)), using CO$_2$ as supercritic eluent, obtaining the pure enantiomers TT1 and TT2.

Enantiomer-A, TT1: 1$^{st}$ eluted on SFC system, retention time (SFC)=4.17 min was obtained as white powder. $^1$H-NMR (400 MHz, DMSO-d$_6$, 300K) δ: 12.66 (1H, s), 7.40-7.16 (3H, m), 4.53-4.23 (1H, m), 4.10-3.79 (4H, m), 3.75-3.33 (2H, m), 3.17-2.92 (1H, m), 1.99 (6H, s), 1.93-1.26 (6H, m), 1.21 (3H, d, J=6.5). MS (ES) $C_{23}H_{27}FN_4O_3$ required: 426, found: 427 (M+H)$^+$.

Enantiomer-B, TT2: 2$^{nd}$ eluted on SFC system, retention time (SFC)=(6.41 min) min was obtained as white powder.

EXAMPLE 87

6-{4-Fluoro-3-[(cis-6-methyl-4-oxooctahydro-2H-pyrido[1,2-a]pyrazin-2-yl)carbonyl]benzyl}-3-oxo-4-(trifluoromethyl)-2,3-dihydropyridazin-1-ium trifluoroacetate (UU1)

UU1 was prepared as described for Example 85, step 6 using 2-fluoro-{[6-oxo-5-(trifluoromethyl)-1,6-dihydropyridazin-3-yl]methyl}-benzoic acid (C7, Preparative Example 3) and SS5 to afford the titled compound (white solid, 21% yield). $^1$H-NMR (300 MHz, DMSO-d$_6$, 300K) δ: 13.54 (1H, s), 7.90 (1H, d, J=4.6), 7.52-7.20 (3H, m), 4.50-4.29 (1H, m), 3.89 (2H, s), 3.90-3.40 (4H, m), 3.16-2.90 (1H, m), 1.95-1.30 (6H, m), 1.22 (3H, d, J=6.9). MS (ES) $C_{22}H_{22}F_4N_4O_3$ required: 466, found: 467

EXAMPLE 88

(6S,9aS)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one and (6R,9aR)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one (VV1 and VV2)

The chiral separation of compound UU1 (Example 87) was performed by critical SFC (column: chiralpak IA (1×25 cm)), flow: 10 ml/min, Tcol: 35° C., Pcol: 100 bar, modifier: 35% (MeOH 0.2% Et$_2$NH)), using CO$_2$ as supercritic eluent, obtaining the pure enantiomers VV1 and VV2.

Enantiomer-A, VV1: 1$^{st}$ eluted on SFC system, retention time (SFC)=4.17 min was obtained as white powder. $^1$H-NMR (300 MHz, DMSO-d$_6$, 300K) δ: 13.54 (1H, s), 7.90 (1H, d, J=4.6), 7.52-7.20 (3H, m), 4.50-4.29 (1H, m), 3.89 (2H, s), 3.90-3.40 (4H, m), 3.16-2.90 (1H, m), 1.95-1.30 (6H, m), 1.22 (3H, d, J=6.9). MS (ES) $C_{22}H_{22}F_4N_4O_3$ required: 466, found: 467.

Enantiomer-B, VV2: 2$^{nd}$ eluted on SFC system, retention time (SFC)=6.08 min was obtained as white powder.

EXAMPLE 89

(9aS)-2-{5-[(4,5-Dimethyl-6-oxo-1,6-dihydropyridazin-3-yl)methyl]-2-fluorobenzoyl}octahydro-4H-pyrido[1,2-a]pyrazin-4-one trifluoroacetate (WW8)

Step 1: Benzyl (2S)-2-(aminocarbonyl)piperidine-1-carboxylate (WW1)

A mixture of (2S)-1-[(benzyloxy)carbonyl]hexahydro-2-pyridinecarboxylic acid (1 eq), TBTU (1.3 eq), DIPEA (1.3 eq), in DMF (2 M) was stirred at R.T. for 30 min then ammonia in dioxane (4 M, 3 eq) was added and stirring was continued for 2 h. The reaction mixture was diluted with EtOAc, washed sequentially with sat. aq. NaHCO$_3$ solution and brine. The solution was dried (Na$_2$SO$_4$), filtered and concentrated under reduced pressure. The crude was purified by crystallization from Et$_2$O giving a white solid. MS (ES) $C_{14}H_{18}N_2O_3$ required: 262, found: 263 (M+H)$^+$.

Step 2: Benzyl (2S)-2-(aminomethyl)piperidine-1-carboxylate (WW2)

A solution of BH$_3$-THF complex (1 M, 1.8 eq) was added to a solution of WW1 (1 eq) in THF (0.2 M) and the mixture was stirred for 24 h. The reaction was quenched by H$_2$O and the THF was removed under reduced pressure. To remaining water solution was added TFA until pH 3. The product WW2 was isolated as the free base by using an Isolute SCX cartridge. MS (ES) C$_{14}$H$_{20}$N$_2$O$_2$ required: 248, found: 249 (M+H)$^+$.

Step 3: Benzyl (2S)-2-{[(tert-butoxycarbonyl)amino] methyl}piperidine-1-carboxylate (WW3)

A solution of Boc$_2$O (1.1 eq) in MeCN was added to an ice-cold solution of WW2 (1 eq) and Et$_3$N (1 eq) in MeCN (0.1 M) and the mixture was stirred for 2 h at 0° C. The reaction mixture was diluted with EtOAc, washed sequentially with sat. aq. NaHCO$_3$ solution and brine. The organic phase was dried (Na$_2$SO$_4$), and concentrated under reduced pressure. The crude product was purified by column chromatography on silica gel, eluting with 10-30% EtOAc/Petroleum ether to afford the desired compound WW3. $^1$H-NMR (300 MHz, CDCl$_3$, 300K) δ: 7.35 (5H, br s), 5.13 (2H, s), 4.72-4.58 (1H, br s), 4.40-4.30 (1H, m), 4.09-3.98 (1H, m), 3.64-3.47 (1H, m), 3.18-3.05 (1H, m), 3.00-2.85 (1H, m), 1.69-1.50 (6H, m), 1.37 (9H, s). MS (ES) C$_{19}$H$_{28}$N$_2$O$_4$ required: 371, found: 349 (M+Na)$^+$.

Step 4: tert-Butyl[(2S)-piperidin-2-ylmethyl]carbamate (WW4)

WW4 was prepared following the procedure described in Example 84, step 6 to afford the desired compound. MS (ES) C$_{11}$H$_{22}$N$_2$O$_2$ required: 214, found: 215 (M+H)$^+$.

Step 5: tert-Butyl {[(2S)-1-(chloroacetyl)piperidin-2-yl]methyl}carbamate (WW5)

WW5 was prepared following the procedure described in Example 84, step 4. MS (ES) C$_{13}$H$_{23}$ClN$_2$O$_3$ required: 290, found: 291 (M+H)$^+$.

Step 6: tert-Butyl (9aS)-4-oxooctahydro-2H-pyrido[1,2-a]pyrazine-2-carboxylate (WW6)

WW6 was prepared following the procedure described in Example 34, step 3. The crude product was purified by column chromatography on silica gel, eluting with 10-40% EtOAc/Petroleum ether to afford the desired compound WW6. $^1$H-NMR (300 MHz, DMSO, 300K) δ: 4.49-4.40 (1H, m), 3.94 (1H, d, J=18.2), 3.85 (1H, d, J=18.2), 3.77-3.68 (1H, m), 3.40-3.28 (1H, m), 3.27-3.15 (2H, m), 1.83-1.56 (3H, m), 1.40 (9H, s), 1.30-1.10 (3H, m). MS (ES) C$_{13}$H$_{22}$N$_2$O$_3$ required: 254, found: 255 (M+H)$^+$.

Step 7: (9aS)-Octahydro-4H-pyrido[1,2-a]pyrazin-4-one (WW7)

WW7 was prepared following the procedure described in Preparative Example 9, step 2 to yield pale orange oil). MS (ES) C$_8$H$_{14}$N$_2$O required: 154, found: 155 (M+H)$^+$.

Step 8: (9aS)-2-{5-[(4,5-dimethyl-6-oxo-1,6-dihydropyridazin-3-yl)methyl]-2-fluorobenzoyl}-octahydro-4H-pyrido[1,2-a]pyrazin-4-one trifluoroacetate (WW8)

WW8 was prepared as described for Example 1 using WW7 (1 eq) to yield the desired product as a white solid, 99% e.e.) $^1$H-NMR (400 MHz, DMSO-d$_6$, 300K) δ: 12.68 (1H, s), 7.38-7.16 (3H, m), 4.53-4.02 (3H, m), 3.92 (2H, s), 3.90-3.71 (1H, m), 3.69-3.39 (2H, m), 3.30-3.18 (1H, m), 2.00 (6H, s), 1.90-1.10 (6H, m). MS (ES) C$_{22}$H$_{25}$FN$_4$O$_3$ required: 412, found: 413

EXAMPLE 90

(9aR)-2-{5-[(4,5-Dimethyl-6-oxo-1,6-dihydropyridazin-3-yl)methyl]-2-fluorobenzoyl}octahydro-4H-pyrido[1,2-a]pyrazin-4-one trifluoroacetate (XX4)

Step 1: tert-Butyl {[1-(chloroacetyl)piperidin-2-yl]methyl}carbamate (XX1)

XX1 was prepared from tert-butyl (piperidin-2-ylmethyl)carbamate following the procedure described in Example 84, step 4. MS (ES) C$_{13}$H$_{23}$ClN$_2$O$_3$ required: 290, found: 291 (M+H)$^+$.

Step 2: tert-Butyl-4-oxooctahydro-2H-pyrido[1,2-a]pyrazine-2-carboxylate (XX2)

XX2 was prepared following the procedure described in Example 34, step 3. $^1$H-NMR (300 MHz, DMSO, 300K) δ: 4.49-4.40 (1H, m), 3.94 (1H, d, J=18.2), 3.85 (1H, d, J=18.2), 3.77-3.68 (1H, m), 3.40-3.28 (1H, m), 3.27-3.15 (2H, m), 1.83-1.56 (3H, m), 1.40 (9H, s), 1.30-1.10 (3H, m). MS (ES) C$_{13}$H$_{22}$N$_2$O$_3$ required: 254, found: 255 (M+H)$^+$.

Step 3: Octahydro-4H-pyrido[1,2-a]pyrazin-4-one (XX3)

XX3 was prepared following the procedure described in Example 34, step 4. MS (ES) C$_8$H$_{14}$N$_2$O required: 154, found: 155 (M+H)$^+$.

Step 4: (9aR)-2-{5-[(4,5-dimethyl-6-oxo-1,6-dihydropyridazin-3-yl)methyl]-2-fluorobenzoyl}octahydro-4H-pyrido[1,2-a]pyrazin-4-one trifluoroacetate (XX4)

XX4 was prepared as described for Example 1 using the racemic XX3 (1 eq). The crude product was purified by column chromatography on silica gel, eluting with 3% MeOH/EtOAc to afford the racemic product. The chiral separation was carried out by SFC (column: chiralpak OJ-H (1×25 cm)), flow: 10 ml/min, Tcol: 35° C., Pcol: 100 bar, modifier: 13% (MeOH 0.2% Et$_2$NH)), using CO$_2$ as supercritical eluent, and the desired enantiomer R(XX4) was recovered as white solid with 99% e.e., determined by comparison with the enantiopure compound WW8.

Enantiomer-R, XX4: 1$^{st}$ eluted on SFC system, retention time (SFC)=6.09 min min was obtained as white powder. $^1$H-NMR (400 MHz, DMSO-d$_6$, 300K) δ: 12.68 (1H, s), 7.38-7.16 (3H, m), 4.53-4.02 (3H, m), 3.92 (2H, s), 3.90-3.71 (1H, m), 3.69-3.39 (2H, m), 3.30-3.18 (1H, m), 2.00 (6H, s), 1.90-1.10 (6H, m). MS (ES) C$_{22}$H$_{25}$FN$_4$O$_3$ required: 412, found: 413.

Enantiomer-S, WW8: 2$^{nd}$ eluted on SFC system, retention time (SFC)=7.13 min was obtained as white powder.

EXAMPLE 91

2-(2-Fluoro-5-{[6-oxo-5-(trifluoromethyl)-1,6-dihydropyridazin-3-yl]methyl}benzoyl)octahydro-4H-pyrido[1,2-a]pyrazin-4-one (YY1)

The racemic mixture YY1 was prepared as described for example 1 using 2-fluoro-{[6-oxo-5-(trifluoromethyl)-1,6-dihydropyridazin-3-yl]methyl}-benzoic acid (C7, Preparative Example 3) instead and XX3 to afford the racemic product as a white powder. $^1$H-NMR (400 MHz, DMSO-d$_6$, 300K) δ: 13.54 (1H, s), 7.90 (1H, d, J=7.6), 7.48-7.22 (3H, m), 4.52-4.05 (3H, m), 4.02 (2H, s), 3.89-3.73 (1H, m), 3.67-3.50 (1H, m), 3.49-3.38 (1H, m), 3.32-3.18 (1H, m), 1.86-1.08 (6H, m). MS (ES) C$_{21}$H$_{20}$F$_4$N$_4$O$_3$ required: 452, found: 453.

EXAMPLE 92

(9aS)-2-(2-Fluoro-5-{[6-oxo-5-(trifluoromethyl)-1,6-dihydropyridazin-3-yl]methyl}benzoyl)octahydro-4H-pyrido[1,2-a]pyrazin-4-one and (9aR)-2-(2-fluoro-5-{[6-oxo-5-(trifluoromethyl)-1,6-dihydropyridazin-3-yl]methyl}benzoyl)octahydro-4H-pyrido[1,2-a]pyrazin-4-one (ZZ1 and ZZ2)

The chiral separation of compound YY1 was carried out by was carried out by SFC (column: chiralpak AD-H (1×25 cm)), flow: 10 ml/min, Tcol: 35° C., Pcol: 100 bar, modifier: 50% (MeOH 0.2% Et$_2$NH)), using CO$_2$ as supercritical eluent, to afford the desired enantiomers ZZ1 and ZZ2, first and second eluted enantiomer respectively.

Enantiomer-A, ZZ1: 1$^{st}$ eluted on SFC system, retention time (SFC)=2.98 min was obtained as white powder. H-NMR (400 MHz, DMSO-d$_6$, 300K) δ: 13.54 (1H, s), 7.90 (1H, d, J=7.6), 7.48-7.22 (3H, m), 4.52-4.05 (3H, m), 4.02 (2H, s), 3.89-3.73 (1H, m), 3.67-3.50 (1H, m), 3.49-3.38 (1H, m), 3.32-3.18 (1H, m), 1.86-1.08 (6H, m). MS (ES) C$_{21}$H$_{20}$F$_4$N$_4$O$_3$ required: 452, found: 453.

Enantiomer-B, ZZ2: 2$^{nd}$ eluted on SFC system, retention time (SFC)=3.98 min min was obtained as white powder.

The Examples in the following table were prepared according to the procedure described in the previous Examples.

| Example | Name | MWt expected | MWt observed | Procedure of Example |
|---|---|---|---|---|
| 93 | 3-{3-[(4-Cyclohexyl-2,2-dimethyl-5-oxopiperazin-1-yl)carbonyl]-4-fluorobenzyl}-4,5-dimethyl-6-oxo-1,6-dihydropyridazin-1-ium trifluoroacetate | 468.6 | 469 | 37 |
| 94 | 3-(3-{[4-(4-Cyanophenyl)-3-oxopiperazin-1-yl]carbonyl}-4-fluorobenzyl)-4,5-dimethyl-6-oxo-1,6-dihydropyridazin-1-ium trifluoroacetate | 459.5 | 460.3 | 1 |
| 95 | 3-[4-Fluoro-3-({4-[4-(methylsulfonyl)phenyl]-3-oxopiperazin-1-yl}carbonyl)benzyl]-4,5-dimethyl-6-oxo-1,6-dihydropyridazin-1-ium trifluoroacetate | 512.6 | 513.3 | 1 |
| 96 | 6-(3-{[4-(2,2-difluoro-1-pyridin-3-ylethyl)-3-oxopiperazin-1-yl]carbonyl}-4-fluorobenzyl)-4,5-dimethyl-3-oxo-2,3-dihydropyridazin-1-ium trifluoroacetate | 499.5 | 500 | 1 |
| 97 | 6-[4-fluoro-3-({4-[(2-methyltetrahydrofuran-2-yl)methyl]-3-oxopiperazin-1-yl}carbonyl)benzyl]-4,5-dimethyl-3-oxo-2,3-dihydropyridazin-1-ium trifluoroacetate | 456.5 | 457 | 1 |
| 98 | 6-(3-{[4-(3,4-dihydro-2H-chromen-3-yl)-3-oxopiperazin-1-yl]carbonyl}-4-fluorobenzyl)-4,5-dimethyl-3-oxo-2,3-dihydropyridazin-1-ium trifluoroacetate | 490.5 | 491 | 1 |
| 99 | 6-(4-fluoro-3-{[3-oxo-4-(1,2,3,4-tetrahydronaphthalen-1-yl)piperazin-1-yl]carbonyl}benzyl)-4,5-dimethyl-3-oxo-2,3-dihydropyridazin-1-ium trifluoroacetate | 488.6 | 489 | 1 |
| 100 | 6-(3-{[4-(2,3-dihydro-1H-inden-1-yl)-3-oxopiperazin-1-yl]carbonyl}-4-fluorobenzyl)-4,5-dimethyl-3-oxo-2,3-dihydropyridazin-1-ium trifluoroacetate | 474.5 | 475 | 1 |
| 101 | 6-[3-({4-[(1R,2R,4S)-Bicyclo[2.2.1]hept-2-yl]-3-oxopiperazin-1-yl}carbonyl)-4-fluorobenzyl]-4,5-dimethyl-3-oxo-2,3-dihydropyridazin-1-ium trifluoroacetate | 452.5 | 453 | 75 |
| 102 | 6-{3-[(4-cyclopentyl-3-methyl-5-oxopiperazin-1-yl)carbonyl]-4-fluorobenzyl}-4,5-dimethyl-3-oxo-2,3-dihydropyridazin-1-ium trifluoroacetate | 440.5 | 441 | 75 |
| 103 | 6-[4-fluoro-3-({3-oxo-4-[(3S)-tetrahydro-2H-pyran-3-yl]piperazin-1-yl}carbonyl)benzyl]-4,5-dimethylpyridazin-3(2H)-one | 442.5 | 443 | 1 |
| 104 | 6-[4-fluoro-3-({3-oxo-4-[(3R)-tetrahydro-2H-pyran-3-yl]piperazin-1-yl}carbonyl)benzyl]-4,5-dimethylpyridazin-3(2H)-one | 442.5 | 443 | 1 |

-continued

| Example | Name | MWt expected | MWt observed | Procedure of Example |
|---|---|---|---|---|
| 105 | 3-{3-[(4-Ethyl-3-oxopiperazin-1-yl]carbonyl]-4-fluorobenzyl}-4-methyl-6-oxo-5-(trifluoromethyl)-1,6-dihydropyridazin-1-ium trifluoroacetate | 440.4 | 441 | 1 |
| 106 | 6-(4-Fluoro-3-{[4-(1-oxaspiro[4.4]non-3-yl)-3-oxopiperazin-1-yl]carbonyl}benzyl)-4,5-dimethylpyridazin-3(2H)-one trifluoroacetate | 482.6 | 483 | 1 |
| 107 | 6-(4-Fluoro-3-{[4-(1-oxaspiro[4.5]dec-3-yl)-3-oxopiperazin-1-yl]carbonyl}benzyl)-4,5-dimethylpyridazin-3(2H)-one trifluoroacetate | 496.6 | 497 | 1 |
| 108 | (9aR)-2-{5-[(4,5-Dimethyl-6-oxo-1,6-dihydropyridazin-3-yl)methyl]-2-fluorobenzoyl}octahydro-4H-pyrido[1,2-a]pyrazin-4-one | 412.5 | 413 | 90 |
| 109 | (9aS)-2-{5-[(4,5-Dimethyl-6-oxo-1,6-Dihydropyridazin-3-yl)methyl]-2-fluorobenzoyl}octahydro-4H-pyrido[1,2-a]pyrazin-4-one | 412.5 | 413 | 89 |
| 110 | 6-(4-fluoro-3-{[4-(1-methylcyclohexyl)-3-oxopiperazin-1-yl]carbonyl}benzyl)-4,5-dimethyl-3-oxo-2,3-dihydropyridazin-1-ium trifluoroacetate | 454.5 | 455.2 | 76 |
| 111 | 6-[4-fluoro-3-({4-[1-(methylsulfonyl)piperidin-4-yl]-3-oxopiperazin-1-yl}carbonyl)benzyl]-4,5-dimethyl-3-oxo-2,3-dihydropyridazin-1-ium trifluoroacetate | 519.6 | 520.2 | 76 |
| 112 | 6-[4-Fluoro-3-({3-oxo-4-[(3R)-tetrahydrofuran-3-yl]piperazin-1-yl}carbonyl)benzyl]-4,5-dimethylpyridazin-3(2H)-one | 428.5 | 429 | 1 |
| 113 | 6-[4-Fluoro-3-({3-oxo-4-[(3S)-tetrahydrofuran-3-yl]piperazin-1-yl}carbonyl)benzyl]-4,5-dimethylpyridazin-3(2H)-one | 428.5 | 429 | 1 |
| 114 | 6-(3-{[(3S)-4-cyclopentyl-3-methyl-5-oxopiperazin-1-yl]carbonyl}-4-fluorobenzyl)-4,5-dimethylpyridazin-3(2H)-one | 440.5 | 441 | 75 |
| 115 | 6-(3-{[(3R)-4-cyclopentyl-3-methyl-5-oxopiperazin-1-yl]carbonyl}-4-fluorobenzyl)-4,5-dimethylpyridazin-3(2H)-one | 440.5 | 441 | 75 |
| 116 | 3-(4-Fluoro-3-{[4-(1-methyl-1H-imidazol-5-yl)-3-oxopiperazin-1-yl]carbonyl}benzyl)-4,5-dimethyl-6-oxo-1,6-dihydropyridazin-1-ium trifluoroacetate | 438.5 | 439 | 1 |
| 117 | 3-(3-{[4-(2,4-Dimethyl-1,3-thiazol-5-yl)-3-oxopiperazin-1-yl]carbonyl}-4-fluorobenzyl)-4,5-dimethyl-6-oxo-1,6-dihydropyridazin-1-ium trifluoroacetate | 469.5 | 470 | 1 |
| 118 | 6-[3-({4-[2,2-difluoro-1-(4-fluorophenyl)ethyl]-3-oxopiperazin-1-yl}carbonyl)-4-fluorobenzyl]-4,5-dimethyl-3-oxo-2,3-dihydropyridazin-1-ium trifluoroacetate | 516.5 | 517 | 1 |
| 119 | 6-(4-fluoro-3-{[3-oxo-4-(3-phenylcyclopentyl)piperazin-1-yl]carbonyl}benzyl)-4,5-dimethyl-3-oxo-2,3-dihydropyridazin-1-ium trifluoroacetate | 502.6 | 503 | 1 |
| 120 | 6-(4-fluoro-3-{[3-oxo-4-(tetrahydro-2H-pyran-4-yl)piperazin-1-yl]carbonyl}benzyl)-4,5-dimethyl-3-oxo-2,3-dihydropyridazin-1-ium trifluoroacetate | 442.5 | 443 | 1 |
| 121 | 6-[4-fluoro-3-({3-oxo-4-[(1R)-1-phenylethyl]piperazin-1-yl}carbonyl)benzyl]-4,5-dimethyl-3-oxo-2,3-dihydropyridazin-1-ium trifluoroacetate | 462.5 | 463 | 1 |

-continued

| Example | Name | MWt expected | MWt observed | Procedure of Example |
|---|---|---|---|---|
| 122 | 6-[4-fluoro-3-({3-oxo-4-[(1S)-1-phenylethyl]piperazin-1-yl}carbonyl)benzyl]-4,5-dimethyl-3-oxo-2,3-dihydropyridazin-1-ium trifluoroacetate | 462.5 | 463 | 1 |
| 123 | 6-(3-{[4-(2,2-difluoro-1R-phenylethyl)-3-oxopiperazin-1-yl]carbonyl}-4-fluorobenzyl)-4,5-dimethyl-3-oxo-2,3-dihydropyridazin-1-ium trifluoroacetate | 498.5 | 499 | 1 |
| 124 | 6-(3-{[4-(2,2-difluoro-1S-phenylethyl)-3-oxopiperazin-1-yl]carbonyl}-4-fluorobenzyl)-4,5-dimethyl-3-oxo-2,3-dihydropyridazin-1-ium trifluoroacetate | 498.5 | 499 | 1 |
| 125 | 3-{3-[(4-Cyclohexyl-3-methyl-5-oxopiperazin-1-yl)carbonyl]-4-fluorobenzyl}-4,5-dimethyl-6-oxo-1,6-dihydropyridazin-1-ium trifluoroacetate | 454.5 | 455 | 75 |
| 126 | 6-(3-{[4-(4,4-Difluorocyclohexyl)-3-methyl-5-oxopiperazin-1-yl]carbonyl}-4-fluorobenzyl)-4,5-dimethylpyridazin-3(2H)-one trifluoroacetate | 490.5 | 491 | 75 |
| 127 | 6-(3-{[4-(3,3-Difluorocyclopentyl)-3-methyl-5-oxopiperazin-1-yl]carbonyl}-4-fluorobenzyl)-4,5-dimethylpyridazin-3(2H)-one trifluoroacetate | 476.5 | 477 | 75 |
| 128 | 6-(3-{[4-(4,4-Dimethylcyclohexyl)-3-methyl-5-oxopiperazin-1-yl]carbonyl}-4-fluorobenzyl)-4,5-dimethylpyridazin-3(2H)-one trifluoroacetate | 482.6 | 483 | 75 |
| 129 | 6-(4-Fluoro-3-{[3-methyl-5-oxo-4-(tetrahydro-2h-pyran-3-yl)piperazin-1-yl]carbonyl}benzyl)-4,5-dimethylpyridazin-3(2H)-one trifluoroacetate | 456.5 | 457 | 75 |
| 130 | 6-(4-Fluoro-3-{[3-methyl-5-oxo-4-(tetrahydrofuran-3-yl)piperazin-1-yl]carbonyl}benzyl)-4,5-dimethylpyridazin-3(2H)-one trifluoroacetate | 442.5 | 443 | 75 |
| 131 | 6-(3-{[4-(2,2-Difluoro-1-phenylethyl)-3-methyl-5-oxopiperazin-1-yl]carbonyl}-4-fluorobenzyl)-4,5-dimethylpyridazin-3(2H)-one trifluoroacetate | 512.5 | 513 | 75 |
| 132 | 6-(3-{[4-(3,4-Dihydro-2H-chromen-3-yl)-3-methyl-5-oxopiperazin-1-yl]carbonyl}-4-fluorobenzyl)-4,5-dimethylpyridazin-3(2H)-one trifluoroacetate | 504.6 | 505 | 75 |
| 133 | 4-ethyl-6-(4-fluoro-3-{[3-oxo-4-(tetrahydro-2H-pyran-3-yl)piperazin-1-yl]carbonyl}benzyl)-3-oxo-2,3-dihydropyridazin-1-ium trifluoroacetate | 442.5 | 443 | 1 |
| 134 | 4-ethyl-6-(4-fluoro-3-{[3-oxo-4-(2,2,2-trifluoroethyl)piperazin-1-yl]carbonyl}benzyl)-3-oxo-2,3-dihydropyridazin-1-ium trifluoroacetate | 440.4 | 441 | 1 |
| 135 | 3-(4-Fluoro-3-{[(9aS)-4-oxooctahydro-2h-pyrido[1,2-a]pyrazin-2-yl]carbonyl}benzyl)-4-methyl-6-oxo-5-(trifluoromethyl)-1,6-dihydropyridazin-1-ium trifluoroacetate | 466.4 | 467.2 | 1 |
| 136 | 3-{4-Fluoro-3-[(6-oxohexahydropyrazino[2,1-c][1,4]oxazin-8(1H)-yl)carbonyl]benzyl}-4-methyl-6-oxo-5-(trifluoromethyl)-1,6-dihydropyridazin-1-ium trifluoroacetate | 468.4 | 469.2 | 1 |
| 137 | 6-{3-[(4-ethyl-3-methyl-5-oxopiperazin-1-yl)carbonyl]-4-fluorobenzyl}-4,5-dimethyl-3-oxo-2,3-dihydropyridazin-1-ium trifluoroacetate | 400.5 | 401 | 75 |
| 138 | 6-(4-fluoro-3-{[4-(4-methoxybenzyl)-3-methyl-5-oxopiperazin-1-yl]carbonyl}benzyl)-4,5-dimethyl-3-oxo-2,3-dihydropyridazin-1-ium trifluoroacetate | 492.6 | 493 | 75 |

-continued

| Example | Name | MWt expected | MWt observed | Procedure of Example |
|---|---|---|---|---|
| 139 | 6-(4-fluoro-3-{[3-methyl-5-oxo-4-(2,2,2-trifluoroethyl)piperazin-1-yl]carbonyl}benzyl)-4,5-dimethyl-3-oxo-2,3-dihydropyridazin-1-ium trifluoroacetate | 454.4 | 455 | 75 |
| 140 | 6-[3-({4-[(1R,4S)-bicyclo[2.2.1]hept-2-yl]-3-methyl-5-oxopiperazin-1-yl}carbonyl)-4-fluorobenzyl]-4,5-dimethyl-3-oxo-2,3-dihydropyridazin-1-ium trifluoroacetate | 466.6 | 467 | 75 |
| 141 | 3-(4-Fluoro-3-{[3-oxo-4-(tetrahydro-2H-pyran-3-yl)piperazin-1-yl]carbonyl}benzyl)-4-methyl-6-oxo-5-(trifluoromethyl)-1,6-dihydropyridazin-1-ium trifluoroacetate | 496.5 | 497 | 1 |
| 142 | 3-(4-Fluoro-3-{[3-oxo-4-(tetrahydrofuran-3-yl)piperazin-1-yl]carbonyl}benzyl)-4-methyl-6-oxo-5-(trifluoromethyl)-1,6-dihydropyridazin-1-ium trifluoroacetate | 482.4 | 483 | 1 |
| 143 | 6-{3-[(4-Ethyl-3-oxopiperazin-1-yl)carbonyl]-4-fluorobenzyl}-5-methyl-4-(trifluoromethyl)pyridazin-3(2H)-one | 440.4 | 441 | 1 |
| 144 | 4-ethyl-6-[4-fluoro-3-({3-oxo-4-[(3S)-tetrahydro-2H-pyran-3-yl]piperazin-1-yl}carbonyl)benzyl]pyridazin-3(2H)-one | 442.5 | 443 | 1 |
| 145 | 4-ethyl-6-[4-fluoro-3-({3-oxo-4-[(3R)-tetrahydro-2H-pyran-3-yl]piperazin-1-yl}carbonyl)benzyl]pyridazin-3(2H)-one | 442.5 | 443 | 1 |
| 146 | 3-(4-Fluoro-3-{[3-oxo-4-(tetrahydro-2H-pyran-4-yl)piperazin-1-yl]carbonyl}benzyl)-4-methyl-6-oxo-5-(trifluoromethyl)-1,6-dihydropyridazin-1-ium trifluoroacetate | 496.5 | 497 | 1 |
| 147 | 3-{3-[(4-Ethyl-3-methyl-5-oxopiperazin-1-yl)carbonyl]-4-fluorobenzyl}-4-methyl-6-oxo-5-(trifluoromethyl)-1,6-dihydropyridazin-1-ium trifluoroacetate | 454.4 | 455 | 1 |
| 148 | 4-Ethyl-6-(4-fluoro-3-{[3-oxo-4-(1,2,3,4-tetrahydronaphthalen-2-yl)piperazin-1-yl]carbonyl}benzyl)pyridazin-3(2H)-one | 488.6 | 489 | 1 |
| 149 | 6-{3-[(4-Cyclopentyl-3-oxopiperazin-1-yl)carbonyl]-4-fluorobenzyl}-3-oxo-4-(pentafluoroethyl)-2,3-dihydropyridazin-1-ium trifluoroacetate | 516.4 | 517 | 81 |
| 150 | 6-(4-Fluoro-3-{[4-(3-fluorocyclopentyl)-3-oxopiperazin-1-yl]carbonyl}benzyl)-4,5-dimethylpyridazin-3(2H)-one | 444.5 | 445 | 80 |
| 151 | 6-(3-{[(3R)-4-cyclopentyl-3-methyl-5-oxopiperazin-1-yl]carbonyl}-4-fluorobenzyl)-4-(trifluoromethyl)pyridazin-3(2H)-one | 480.5 | 481 | 75 |
| 152 | 6-(3-{[(3S)-4-cyclopentyl-3-methyl-5-oxopiperazin-1-yl]carbonyl}-4-fluorobenzyl)-4-(trifluoromethyl)pyridazin-3(2H)-one | 480.5 | 481 | 75 |
| 153 | 6-[4-fluoro-3-({3-oxo-4-[(3S)-tetrahydro-2H-pyran-3-yl]piperazin-1-yl}carbonyl)benzyl]-4-(trifluoromethyl)pyridazin-3(2H)-one | 482.4 | 483 | 1 |
| 154 | 6-[4-fluoro-3-({3-oxo-4-[(3R)-tetrahydro-2H-pyran-3-yl]piperazin-1-yl}carbonyl)benzyl]-4-(trifluoromethyl)pyridazin-3(2H)-one | 482.4 | 483 | 1 |
| 155 | 6-(3-{[(3S)-4-ethyl-3-methyl-5-oxopiperazin-1-yl]carbonyl}-4-fluorobenzyl)-5-methyl-4-(trifluoromethyl)pyridazin-3(2H)-one | 454.4 | 455 | 1 |

-continued

| Example | Name | MWt expected | MWt observed | Procedure of Example |
|---|---|---|---|---|
| 156 | 6-(3-{[(3R)-4-ethyl-3-methyl-5-oxopiperazin-1-yl]carbonyl}-4-fluorobenzyl)-5-methyl-4-(trifluoromethyl)pyridazin-3(2H)-one | 454.4 | 455 | 1 |
| 157 | 6-[4-fluoro-3-({(3S)-3-methyl-5-oxo-4-[(3R)-tetrahydrofuran-3-yl]piperazin-1-yl}carbonyl)benzyl]-4,5-dimethylpyridazin-3(2H)-one | 442.5 | 443 | 75 |
| 158 | 6-[4-fluoro-3-({(3R)-3-methyl-5-oxo-4-[(3R)-tetrahydrofuran-3-yl]piperazin-1-yl}carbonyl)benzyl]-4,5-dimethylpyridazin-3(2H)-one | 442.5 | 443 | 75 |
| 159 | 4-ethyl-6-[4-fluoro-3-({3-oxo-4-[(2S)-1,2,3,4-tetrahydronaphthalen-2-yl]piperazin-1-yl}carbonyl)benzyl]pyridazin-3(2H)-one | 488.6 | 489 | 1 |
| 160 | 4-ethyl-6-[4-fluoro-3-({3-oxo-4-[(2R)-1,2,3,4-tetrahydronaphthalen-2-yl]piperazin-1-yl}carbonyl)benzyl]pyridazin-3(2H)-one | 488.6 | 489 | 1 |

The Examples in the following table were prepared according to the procedures described in the previous examples

| Example | Name | MWt | M + H+ | Procedure of Example |
|---|---|---|---|---|
| 161 | 6-[4-Fluoro-3-({4-[(1S)-1-methylpropyl]-3-oxopiperazin-1-yl}carbonyl)benzyl]-4,5-dimethylpyridazin-3(2H)-one | 414.5 | 415 | 76 |
| 162 | 6-(4-Fluoro-3-{[4-(2-methoxy-1-methylethyl)-3-oxopiperazin-1-yl]carbonyl}benzyl)-4,5-dimethylpyridazin-3(2H)-one | 430.5 | 431 | 76 |
| 163 | 6-{3-[(4-Cyclobutyl-3-methyl-5-oxopiperazin-1-yl)carbonyl]-4-fluorobenzyl}-4,5-dimethylpyridazin-3(2H)-one | 426.5 | 427 | 75 |
| 164 | 6-{3-[(4-Cyclobutyl-3-ethyl-5-oxopiperazin-1-yl)carbonyl]-4-fluorobenzyl}-4,5-dimethylpyridazin-3(2H)-one | 440.5 | 441 | 75 |
| 165 | 6-(3-{[4-(3-Chlorophenyl)-3-methyl-5-oxopiperazin-1-yl]carbonyl}-4-fluorobenzyl)-4,5-dimethylpyridazin-3(2H)-one | 482.9 | 483 | 78 |
| 166 | 4-((2S)-4-{5-[(4,5-Dimethyl-6-oxo-1,6-dihydropyridazin-3-yl)methyl]-2-fluorobenzoyl}-2-methyl-6-oxopiperazin-1-yl)benzonitrile | 473.5 | 474 | 1 |
| 167 | 6-(3-{[4-(1-Ethylpropyl)-3-oxopiperazin-1-yl]carbonyl}-4-fluorobenzyl)-4,5-dimethylpyridazin-3(2H)-one | 428.5 | 429 | 76 |
| 168 | 6-[4-Fluoro-3-({4-[(1R)-1-methylpropyl]-3-oxopiperazin-1-yl}carbonyl)benzyl]-4,5-dimethylpyridazin-3(2H)-one | 414.5 | 415 | 76 |
| 169 | 6-[4-Fluoro-3-({4-[(1S)-2-methoxy-1-methylethyl]-3-oxopiperazin-1-yl}carbonyl)benzyl]-4,5-dimethylpyridazin-3(2H)-one | 430.5 | 431 | 76 |
| 170 | 6-(4-Fluoro-3-{[4-(2-methoxyethyl)-3-oxopiperazin-1-yl]carbonyl}benzyl)-4,5-dimethylpyridazin-3(2H)-one | 416.5 | 417 | 76 |
| 171 | 6-(3-{[4-(2-Ethoxyethyl)-3-oxopiperazin-1-yl]carbonyl}-4-fluorobenzyl)-4,5-dimethylpyridazin-3(2H)-one | 430.5 | 431 | 76 |

-continued

| Example | Name | MWt | M + H+ | Procedure of Example |
|---|---|---|---|---|
| 172 | 6-(4-Fluoro-3-{[4-(2-isopropoxyethyl)-3-oxopiperazin-1-yl]carbonyl}benzyl)-4,5-dimethylpyridazin-3(2H)-one | 444.5 | 445 | 76 |
| 173 | 6-(4-Fluoro-3-{[4-(2-hydroxy-2-methylpropyl)-3-oxopiperazin-1-yl]carbonyl}benzyl)-4,5-dimethylpyridazin-3(2H)-one | 430.5 | 431 | 76 |
| 174 | 4-((2S)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile | 491.5 | 492 | 1 |
| 175 | 6-(3-{[(3R)-4-Cyclobutyl-3-methyl-5-oxopiperazin-1-yl]carbonyl}-4-fluorobenzyl)-4,5-dimethylpyridazin-3(2H)-one | 426.5 | 427 | 75 |
| 176 | 6-(3-{[(3S)-4-Cyclobutyl-3-methyl-5-oxopiperazin-1-yl]carbonyl}-4-fluorobenzyl)-4,5-dimethylpyridazin-3(2H)-one | 426.5 | 427 | 75 |
| 177 | 6-(3-{[(3S)-4-(3-Chlorophenyl)-3-methyl-5-oxopiperazin-1-yl]carbonyl}-4-fluorobenzyl)-4,5-dimethylpyridazin-3(2H)-one | 482.9 | 483 | 78 |
| 178 | 6-(3-{[(3R)-4-(3-Chlorophenyl)-3-methyl-5-oxopiperazin-1-yl]carbonyl}-4-fluorobenzyl)-4,5-dimethylpyridazin-3(2H)-one | 482.9 | 483 | 78 |
| 179 | 6-[4-Fluoro-3-({4-[(1R)-2-methoxy-1-methylethyl]-3-oxopiperazin-1-yl}carbonyl)benzyl]-4,5-dimethylpyridazin-3(2H)-one | 430.5 | 431 | 76 |
| 180 | 6-(3-{[(3R)-4-Cyclobutyl-3-ethyl-5-oxopiperazin-1-yl]carbonyl}-4-fluorobenzyl)-4,5-dimethylpyridazin-3(2H)-one | 440.5 | 441 | 75 |
| 181 | 6-(3-{[(3S)-4-Cyclobutyl-3-ethyl-5-oxopiperazin-1-yl]carbonyl}-4-fluorobenzyl)-4,5-dimethylpyridazin-3(2H)-one | 440.5 | 441 | 75 |
| 182 | 6-[3-({4-[(1R)-1,2-Dimethylpropyl]-3-oxopiperazin-1-yl}carbonyl)-4-fluorobenzyl]-4,5-dimethylpyridazin-3(2H)-one | 428.5 | 429 | 76 |
| 183 | 6-[3-({4-[(1S)-1,2-Dimethylpropyl]-3-oxopiperazin-1-yl}carbonyl)-4-fluorobenzyl]-4,5-dimethylpyridazin-3(2H)-one | 428.5 | 429 | 76 |
| 184 | 6-{3-[(4-Cyclohexyl-3-ethyl-5-oxopiperazin-1-yl)carbonyl]-4-fluorobenzyl}-4,5-dimethylpyridazin-3(2H)-one | 468.6 | 469 | 75 |
| 185 | 6-{3-[(4-Cyclopentyl-3-isobutyl-5-oxopiperazin-1-yl)carbonyl]-4-fluorobenzyl}-4,5-dimethylpyridazin-3(2H)-one | 482.6 | 483 | 75 |
| 186 | 6-{3-[(4-Cyclopentyl-3-ethyl-5-oxopiperazin-1-yl)carbonyl]-4-fluorobenzyl}-4,5-dimethylpyridazin-3(2H)-one | 454.5 | 455 | 75 |
| 187 | 6-(3-{[(3R)-4-(4-Chloro-3-fluorophenyl)-3-methyl-5-oxopiperazin-1-yl]carbonyl}-4-fluorobenzyl)-4,5-dimethylpyridazin-3(2H)-one | 500.9 | 501 | 1 |
| 188 | 6-(3-{[4-(3,3-Difluorocyclobutyl)-3-methyl-5-oxopiperazin-1-yl]carbonyl}-4-fluorobenzyl)-4,5-dimethylpyridazin-3(2H)-one | 462.5 | 463 | 75 |
| 189 | 4-((2R)-4-{5-[(4,5-Dimethyl-6-oxo-1,6-dihydropyridazin-3-yl)methyl]-2-fluorobenzoyl}-2-methyl-6-oxopiperazin-1-yl)benzonitrile | 473.5 | 474 | 1 |
| 190 | 6-(3-{[(3R)-4-(3-Chlorophenyl)-3-methyl-5-oxopiperazin-1-yl]carbonyl}-4-fluorobenzyl)-4,5-dimethylpyridazin-3(2H)-one | 482.9 | 483 | 1 |
| 191 | 4-((2R)-4-{5-[(4,5-Dimethyl-6-oxo-1,6-dihydropyridazin-3-yl)methyl]-2- | 491.5 | 492 | 1 |

-continued

| Example | Name | MWt | M + H+ | Procedure of Example |
|---|---|---|---|---|
|  | fluorobenzoyl}-2-methyl-6-oxopiperazin-1-yl)-2-fluorobenzonitrile |  |  |  |
| 192 | 6-[4-Fluoro-3-({3-oxo-4-[(1S)-2,2,2-trifluoro-1-methylethyl]piperazin-1-yl}carbonyl)benzyl]-4,5-dimethylpyridazin-3(2H)-one | 454.4 | 455 | 76 |
| 193 | 6-(3-{[(3R)-4-(3,5-Difluorophenyl)-3-methyl-5-oxopiperazin-1-yl]carbonyl}-4-fluorobenzyl)-4,5-dimethylpyridazin-3(2H)-one | 484.5 | 485 | 1 |
| 194 | 6-(3-{[(3R)-4-(4-Chlorophenyl)-3-methyl-5-oxopiperazin-1-yl]carbonyl}-4-fluorobenzyl)-4,5-dimethylpyridazin-3(2H)-one | 482.9 | 483 | 1 |
| 195 | 6-(4-Fluoro-3-{[(3R)-3-methyl-5-oxo-4-(2-thienyl)piperazin-1-yl]carbonyl}benzyl)-4,5-dimethylpyridazin-3(2H)-one | 454.5 | 455 | 1 |
| 196 | 6-(3-{[(3R)-4-(4-Chloro-2-fluorophenyl)-3-methyl-5-oxopiperazin-1-yl]carbonyl}-4-fluorobenzyl)-4,5-dimethylpyridazin-3(2H)-one | 500.9 | 501 | 1 |
| 197 | 5-((2R)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile | 491.5 | 492 | 1 |
| 198 | 6-(3-{[(3R)-4-(3-Chloro-5-fluorophenyl)-3-methyl-5-oxopiperazin-1-yl]carbonyl}-4-fluorobenzyl)-4,5-dimethylpyridazin-3(2H)-one | 500.9 | 501 | 1 |
| 199 | 6-(3-{[(3R)-4-(3-Chloro-4-fluorophenyl)-3-methyl-5-oxopiperazin-1-yl]carbonyl}-4-fluorobenzyl)-4,5-dimethylpyridazin-3(2H)-one | 500.9 | 501 | 1 |
| 200 | 6-[4-Fluoro-3-({3-oxo-4-[(1R)-2,2,2-trifluoro-1-methylethyl]piperazin-1-yl}carbonyl)benzyl]-4,5-dimethylpyridazin-3(2H)-one | 454.4 | 455 | 76 |
| 201 | 4-((2R)-4-{5-[(4,5-Dimethyl-6-oxo-1,6-dihydropyridazin-3-yl)methyl]-2-fluorobenzoyl}-2-methyl-6-oxopiperazin-1-yl)-3-fluorobenzonitrile | 491.5 | 492 | 1 |
| 202 | 3-((2R)-4-{5-[(4,5-Dimethyl-6-oxo-1,6-dihydropyridazin-3-yl)methyl]-2-fluorobenzoyl}-2-methyl-6-oxopiperazin-1-yl)-5-fluorobenzonitrile | 491.5 | 492 | 1 |
| 203 | 6-(3-{[(3R)-4-(3,4-Difluorophenyl)-3-methyl-5-oxopiperazin-1-yl]carbonyl}-4-fluorobenzyl)-4,5-dimethylpyridazin-3(2H)-one | 484.5 | 485 | 1 |
| 204 | 6-(3-{[4-(1-Cyclopropylethyl)-3-oxopiperazin-1-yl]carbonyl}-4-fluorobenzyl)-4,5-dimethylpyridazin-3(2H)-one | 426.5 | 427 | 76 |
| 205 | 6-(3-{[(3R)-4-(5-Chloro-2-fluorophenyl)-3-methyl-5-oxopiperazin-1-yl]carbonyl}-4-fluorobenzyl)-4,5-dimethylpyridazin-3(2H)-one | 500.9 | 501 | 1 |
| 206 | 6-(3-{[(3R)-4-(3-Chloro-2-fluorophenyl)-3-methyl-5-oxopiperazin-1-yl]carbonyl}-4-fluorobenzyl)-4,5-dimethylpyridazin-3(2H)-one | 500.9 | 501 | 1 |
| 207 | 6-(3-{[(3R)-4-Cyclopentyl-3-isopropyl-5-oxopiperazin-1-yl]carbonyl}-4-fluorobenzyl)-4,5-dimethylpyridazin-3(2H)-one | 468.6 | 469 | 75 |
| 208 | 6-(3-{[(3S)-4-(4-Chloro-3-fluorophenyl)-3-methyl-5-oxopiperazin-1-yl]carbonyl}-4-fluorobenzyl)-4,5-dimethylpyridazin-3(2H)-one | 500.9 | 501 | 1 |
| 209 | 6-(3-{[(3S)-4-(3,3-Difluorocyclobutyl)-3-methyl-5-oxopiperazin-1-yl]carbonyl}-4-fluorobenzyl)-4,5-dimethylpyridazin-3(2H)-one | 462.5 | 463 | 75 |

-continued

| Example | Name | MWt | M + H+ | Procedure of Example |
|---|---|---|---|---|
| 210 | 6-(3-{[(3R)-4-(3,3-Difluorocyclobutyl)-3-methyl-5-oxopiperazin-1-yl]carbonyl}-4-fluorobenzyl)-4,5-dimethylpyridazin-3(2H)-one | 462.5 | 463 | 75 |
| 211 | 6-{4-Fluoro-3-[(4-isopropyl-3-oxopiperazin-1-yl)carbonyl]benzyl}-4,5-dimethylpyridazin-3(2H)-one | 400.5 | 401 | 76 |
| 212 | 6-[4-Fluoro-3-({4-[(trans)-3-fluorocyclopentyl]-3-oxopiperazin-1-yl}carbonyl)benzyl]-4,5-dimethylpyridazin-3(2H)-one | 444.5 | 445 | 80 |

The invention claimed is:

1. A compound of structural formula I:

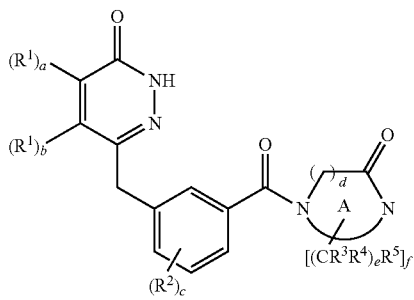

wherein:
a is 0 or 1;
b is 0 or 1;
c is 0, 1, 2, 3 or 4;
d is 1 or 2;
e is 0, 1, 2, 3 or 4;
f is 0, 1, 2, 3 or 4;
A is a 6 to 15 membered monocyclic, fused, bridged or spiro saturated heterocyclic ring containing two N atoms and zero or one O atom, substituted by one oxo group;
each $R^1$ is independently $C_{1-6}$alkyl, halo$C_{1-6}$alkyl, halogen or cyano;
each $R^2$ is independently hydroxy, halogen, cyano, $C_{1-6}$alkyl, halo$C_{1-6}$alkyl, $C_{1-6}$alkoxy, halo$C_{1-6}$alkoxy or $NR^aR^b$;
each of $R^3$ and $R^4$ is independently hydrogen, halogen, $C_{1-6}$alkyl or halo$C_{1-6}$alkyl;
each $R^5$ is independently cyano, halogen, hydroxy, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;

each $R^6$ is independently hydroxy, oxo, cyano, halogen, nitro, $C_{1-6}$alkyl, $C_{1-6}$alkoxy, $C_{2-10}$alkenyl, halo$C_{1-6}$alkyl, halo$C_{1-6}$alkoxy, —O(C=O)$C_{1-6}$alkyl, —(C=O)OC$_{1-6}$alkyl, $NR^aR^b$, $CONR^aR^b$, $NR^aCOR^b$, $S(O)_rNR^aR^b$, $S(O)_rR^c$, $NR^aS(O)_rR^c$ or a ring which is: $C_{3-10}$cycloalkyl, $C_{6-10}$aryl, $C_{6-10}$aryl$C_{1-6}$alkyl, $C_{6-10}$arylcarbonyl, $C_{6-10}$aryloxycarbonyl, $C_{6-10}$aryl$C_{1-6}$alkoxycarbonyl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 nitrogen atoms; any of which rings being optionally substituted by one, two or three groups independently selected from halogen, $C_{1-6}$alkyl or halo$C_{1-6}$alkyl;
r is 0, 1 or 2;
each of $R^a$ and $R^b$ is independently hydrogen, $C_{1-6}$alkyl or a ring which is: $C_{3-10}$cycloalkyl, $C_{6-10}$aryl, a 5 membered heteroaromatic ring containing 1, 2, 3 or 4 heteroatoms independently selected from N, O and S, not more than one heteroatom of which is O or S or a 6 membered heteroaromatic ring containing 1, 2 or 3 N atoms; any of which rings being optionally substituted by one, two or three groups independently selected from halogen, $C_{1-6}$alkyl or halo$C_{1-6}$alkyl;
$R^c$ is hydrogen or $C_{1-6}$alkyl;
or a pharmaceutically acceptable salt, stereoisomer or tautomer thereof.

2. A compound of claim 1 of formula II:

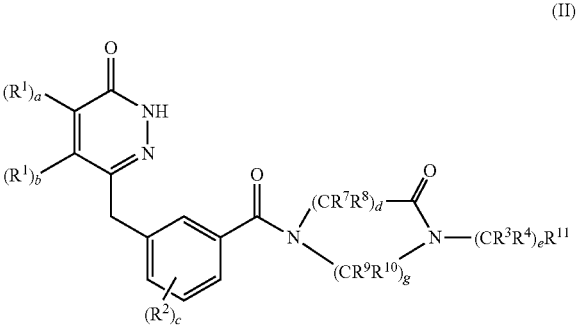

wherein:
a, b, c, d, e, $R^1$, $R^2$, $R^3$ and $R^4$ are as defined in claim 1;
g is 2 or 3;
each of $R^7$, $R^8$, $R^9$ and $R^{10}$ is independently hydrogen, halogen, $C_{1-6}$alkyl or halo$C_{1-6}$alkyl;
$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$ alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;

$R^6$ is as defined in claim 1;

or one $R^7$ together with one $R^9$ forms a bridge containing 1, 2, or 3 carbon atoms optionally substituted by one, two or three groups independently selected from halogen or $C_{1-6}$alkyl;

or one $R^9$ and one $R^{10}$ together with the carbon atom to which they are attached form a spiro ring containing 3, 4, 5 or 6 carbon atoms optionally substituted by one, two or three groups independently selected from halogen, $C_{1-6}$alkyl or halo$C_{1-6}$alkyl;

or $R^{11}(CR^3R^4)_e$ together with)N—$(CR^9R^{10})$ forms a 4 to 8 membered fused saturated heterocyclic ring containing one N atom, optionally substituted by one, two or three groups independently selected from halogen, $C_{1-6}$alkyl or halo$C_{1-6}$alkyl;

or a pharmaceutically acceptable salt, stereoisomer or tautomer thereof.

3. A compound of claim 1 of formula III:

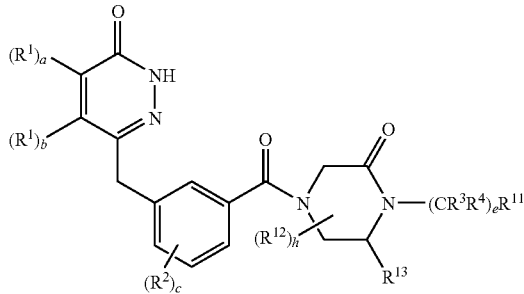

(III)

wherein:
a, b, c, $R^1$ and $R^2$ are as defined in claim 1;
h is 0, 1 or 2;
$R^{12}$ is $C_{1-6}$alkyl or halo$C_{1-6}$alkyl;
either:
$R^{13}$ is hydrogen or $R^{12}$;
e is 0, 1, 2, 3 or 4;
each $R^3$ and $R^4$ is independently hydrogen, halogen, $C_{1-6}$alkyl or halo$C_{1-6}$alkyl; and
each $R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$;

$R^6$ is as defined in claim 1;

or:
$R^{11}(CR^3R^4)_e$ and $R^{13}$ together with the N and C atoms to which they are attached form a fused 5, 6 or 7 membered saturated heterocyclic ring containing one N atom, optionally substituted by one, two or three groups independently selected from halogen, $C_{1-6}$alkyl or halo$C_{1-6}$alkyl;

or a pharmaceutically acceptable salt, stereoisomer or tautomer thereof.

4. A compound of claim 1 of formula IV:

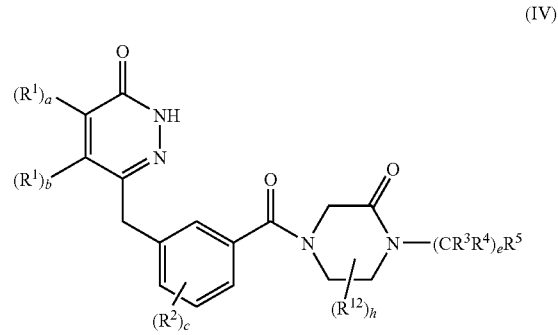

(IV)

wherein:
a, b, c, e, $R^1$, $R^2$, $R^3$, $R^4$ and $R^5$ are as defined in claim 1;
h is 0, 1 or 2;
$R^{12}$ is $C_{1-6}$alkyl or halo$C_{1-6}$alkyl;
or a pharmaceutically acceptable salt, stereoisomer or tautomer thereof.

5. A compound of claim 1 of formula V:

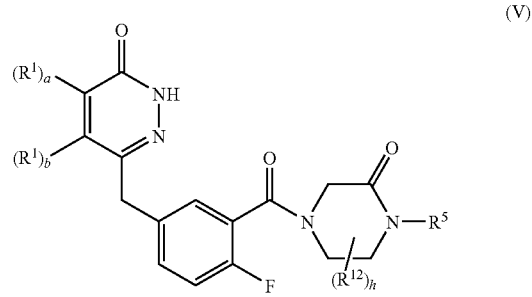

(V)

wherein:
a, b, and $R^1$ are as defined in claim 1;
h is 0 or 1;
$R^5$ is $C_{3-10}$cycloalkyl or $C_{6-10}$aryl, optionally substituted by one, two or three groups independently selected from fluorine, chlorine or cyano;
$R^{12}$ is methyl;
or a pharmaceutically acceptable salt, stereoisomer or tautomer thereof.

6. A compound of claim 1 wherein c is 1 and $R^2$ is halogen.

7. A compound of claim 4 wherein $R^5$ is halogen, hydroxy, $C_{1-4}$alkyl, halo$C_{1-4}$alkyl, $C_{1-6}$alkoxy, $C_{1-4}$alkoxycarbonyl or a ring which is: phenyl, cyclohexyl, cyclopentyl, pyridinyl, naphthyl, thienyl, tetrahydropyranyl, bicyclo[1.1.1]pentyl, tetrahydronaphthalenyl, oxadiazolyl, cyclobutyl, quinolinyl, benzothienyl, thiazolyl, pyrimidinyl, tetrahydrofuranyl, dihydroindenyl, cycloheptyl, cyclopropyl, dihydrochromenyl, bicyclo[2.2.1]heptyl, oxaspiro[4.4]nonyl, oxaspiro[4.5]decyl, piperidinyl or imidazolyl; any of which rings being optionally substituted by one, two or three groups independently selected from $R^6$.

8. A compound of claim 2 wherein:
each of $R^7$, $R^8$, $R^9$ and $R^{10}$ is independently hydrogen, halogen, $C_{1-6}$alkyl or halo$C_{1-6}$alkyl; and
$R^{11}$ is independently cyano, halogen, $C_{1-6}$alkyl, $C_{1-6}$alkoxy, $C_{2-10}$alkenyl, halo$C_{1-6}$alkyl, halo$C_{1-6}$alkoxy, $C_{1-6}$alkylcarbonyl, $C_{1-6}$alkoxycarbonyl or a ring which is: $C_{3-10}$cycloalkyl, $C_{6-10}$aryl, $C_{6-10}$aryloxy, oxetanyl, azetidinyl, a 5 or 6 membered saturated or partially saturated heterocyclic ring containing 1, 2 or 3 atoms independently selected from N, O and S, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 N atoms or a 7-10 membered unsaturated, partially saturated or saturated heterocyclic ring containing 1, 2, 3 or 4 heteroatoms independently selected from N, O and S; any of which rings being optionally substituted by one, two or three groups independently selected from $R^6$.

9. A compound of claim 8 wherein $R^6$ is cyano, halogen, $C_{1-6}$alkyl, $C_{1-6}$alkoxy, halo$C_{1-6}$alkyl, $C_{1-6}$alkylsulfonyl or $C_{6-10}$aryl.

10. A compound of claim 1 selected from:
6-{4-Fluoro-3-[(3-oxo-4-phenylpiperazin-1-yl)carbonyl]benzyl}-4,5-dimethyl-3-oxo-2,3-dihydropyridazin-1-ium trifluoroacetate;
6-{3-[(4-Cyclohexyl-3-oxopiperazin-1-yl)carbonyl]-4-fluorobenzyl}-4,5-dimethyl-3-oxo-2,3-dihydropyridazin-1-ium trifluoroacetate;
6-{3-[(4-Cyclopentyl-3-oxopiperazin-1-yl)carbonyl]-4-fluorobenzyl}-4,5-dimethylpyridazin-3(2H)-one;
6-{4-Fluoro-3-[(3-oxo-4-phenylpiperazin-1-yl)carbonyl]benzyl}-4,5-dimethylpyridazin-3(2H)-one hydrochloride;
4-Ethyl-6-{4-fluoro-3-[(3-oxo-4-phenylpiperazin-1-yl)carbonyl]benzyl}pyridazin-3(2H)-one trifluoroacetate;
6-{3-[(4-Cyclohexyl-3-oxopiperazin-1-yl)carbonyl]-4-fluorobenzyl}-4-ethylpyridazin-3(2H)-one trifluoroacetate;
3-{4-Fluoro-3-[(4-methyl-3-oxopiperazin-1-yl)carbonyl]benzyl}-4,5-dimethyl-6-oxo-1,6-dihydropyridazin-1-ium trifluoroacetate;
3-(4-Fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate;
6-(3-{[4-(2-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,4-Difluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(3,5-Difluorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(4-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-(3-{[4-(2-Chlorophenyl)-3-oxopiperazin-1-yl]carbonyl}-4-fluorobenzyl)-4,5-dimethyl-3-oxo-2,3-dihydropyridazin-1-ium trifluoroacetate;
6-[4-Fluoro-3-({3-oxo-4-[2-(trifluoromethyl)phenyl]piperazin-1-yl}carbonyl)benzyl]-4,5-dimethyl-3-oxo-2,3-dihydropyridazin-1-ium trifluoroacetate;
6-(3-{[4-(2-Chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate;
6-{3-[(4-Ethyl-3-oxopiperazin-1-yl)carbonyl]-4-fluorobenzyl}-4,5-dimethylpyridazin-3(2H)-one trifluoroacetate;
6-{3-[(4-Butyl-3-oxopiperazin-1-yl)carbonyl]-4-fluorobenzyl}-4,5-dimethylpyridazin-3(2H)-one trifluoroacetate;
6-(3-{[4-(3,5-Dimethylbenzyl)-3-oxopiperazin-1-yl]carbonyl}-4-fluorobenzyl)-4,5-dimethylpyridazin-3(2H)-one trifluoroacetate;
6-(4-Fluoro-3-{[4-(4-methoxybenzyl)-3-oxopiperazin-1-yl]carbonyl}benzyl)-4,5-dimethylpyridazin-3(2H)-one trifluoroacetate;
6-(4-Fluoro-3-{[3-oxo-4-(2-phenylethyl)piperazin-1-yl]carbonyl}benzyl)-4,5-dimethylpyridazin-3(2H)-one trifluoroacetate;
6-(4-Fluoro-3-{[4-(3-methoxyphenyl)-3-oxopiperazin-1-yl]carbonyl}benzyl)-4,5-dimethylpyridazin-3(2H)-one trifluoroacetate;
6-(3-{[4-(3,5-Dimethylphenyl)-3-oxopiperazin-1-yl]carbonyl}-4-fluorobenzyl)-4,5-dimethylpyridazin-3(2H)-one trifluoroacetate;
Methyl (4-{5-[(4,5-dimethyl-6-oxo-1,6-dihydropyridazin-3-yl)methyl]-2-fluorobenzoyl}-2-oxopiperazin-1-yl)acetate trifluoroacetate;
3-{3-[(4-Cyclohexyl-3-oxopiperazin-1-yl)carbonyl]-4-fluorobenzyl}-4-methyl-6-oxo-5-(trifluoromethyl)-1,6-dihydropyridazin-1-ium trifluoroacetate;
3-(3-{[4-(3,4-Difluorophenyl)-3-oxopiperazin-1-yl]carbonyl}-4-fluorobenzyl)-4-methyl-6-oxo-5-(trifluoromethyl)-1,6-dihydropyridazin-1-ium trifluoroacetate;
6-{3-[(4-Cyclohexyl-3-oxopiperazin-1-yl)carbonyl]-4-fluorobenzyl}-3-oxo-4-(trifluoromethyl)-2,3-dihydropyridazin-1-ium trifluoroacetate;
3-{3-[(4-Cyclohexyl-3-oxopiperazin-1-yl)carbonyl]-4-fluorobenzyl}-4-ethyl-5-methyl-6-oxo-1,6-dihydropyridazin-1-ium trifluoroacetate;
3-{3-[(4-Cyclohexyl-3-oxopiperazin-1-yl)carbonyl]-4-fluorobenzyl}-5-ethyl-4-methyl-6-oxo-1,6-dihydropyridazin-1-ium trifluoroacetate;
3-{3-[(4-Cyclopentyl-3-oxopiperazin-1-yl)carbonyl]-4-fluorobenzyl}-5-ethyl-6-oxo-1,6-dihydropyridazin-1-ium trifluoroacetate;
3-{4-Fluoro-3-[(3-oxo-4-pyridin-2-ylpiperazin-1-yl)carbonyl]benzyl}-4,5-dimethyl-6-oxo-1, 6-dihydropyridazin-1-ium trifluoroacetate;
6-{4-Fluoro-3-[(4-oxooctahydro-2H-pyrido[1,2-a]pyrazin-2-yl)carbonyl]benzyl}-4,5-dimethyl-3-oxo-2,3-dihydropyridazin-1-ium trifluoroacetate;
6-{3-[(4-Cyclopentyl-3-oxopiperazin-1-yl)carbonyl]-4-fluorobenzyl}-3-oxo-4-(trifluoromethyl)-2,3-dihydropyridazin-1-ium trifluoroacetate;
6-{3-[(4-Cyclohexyl-3-oxo-1,4-diazepan-1-yl)carbonyl]-4-fluorobenzyl}-4,5-dimethyl-3-oxo-2,3-dihydropyridazin-1-ium trifluoroacetate;

6-{3-[(4-Cyclohexyl-2-methyl-3-oxopiperazin-1-yl)carbonyl]-4-fluorobenzyl}-4,5-dimethyl-3-oxo-2,3-dihydropyridazin-1-ium trifluoroacetate;

6-{4-Fluoro-3-[(4-isopropyl-5-oxo-1,4-diazepan-1-yl)carbonyl]benzyl}-4,5-dimethyl-3-oxo-2,3-dihydropyridazin-1-ium trifluoroacetate;

3-{3-[(4-Cyclohexyl-2,2-dimethyl-3-oxopiperazin-1-yl)carbonyl]-4-fluorobenzyl}-4,5-dimethyl-6-oxo-1,6-dihydropyridazin-1-ium trifluoroacetate;

6-{4-Fluoro-3-[(3-oxo-4-pyridin-3-ylpiperazin-1-yl)carbonyl]benzyl}-4,5-dimethylpyridazin-3(2H)-one;

6-{3-[(4-Cyclohexyl-3-oxopiperazin-1-yl)carbonyl]-4-fluorobenzyl}-5-ethyl-4-(trifluoromethyl)pyridazin-3(2H)-one trifluoroacetate;

6-(4-Fluoro-3-{[4-(4-fluorophenyl)-3-oxopiperazin-1-yl]carbonyl}benzyl)-4,5-dimethyl-3-oxo-2,3-dihydropyridazin-1-ium trifluoroacetate;

(1S,4S)-5-{5-[(4,5-Dimethyl-6-oxo-1,6-dihydropyridazin-3-yl)methyl]-2-fluorobenzoyl}-2-phenyl-2,5-diazabicyclo[2.2.1]heptan-3-one trifluoroacetate;

3-(3-{[4-(3,5-Dichlorophenyl)-3-oxopiperazin-1-yl]carbonyl}-4-fluorobenzyl)-4,5-dimethyl-6-oxo-1,6-dihydropyridazin-1-ium trifluoroacetate;

3-(4-Fluoro-3-{[4-(1-naphthyl)-3-oxopiperazin-1-yl]carbonyl}benzyl)-4,5-dimethyl-6-oxo-1,6-dihydropyridazin-1-ium trifluoroacetate;

3-(4-Fluoro-3-{[3-oxo-4-(2-thienyl)piperazin-1-yl]carbonyl}benzyl)-4,5-dimethyl-6-oxo-1,6-dihydropyridazin-1-ium trifluoroacetate;

6-(4-Fluoro-3-{[3-oxo-4-(3,3,3-trifluoro-2-methylpropyl)piperazin-1-yl]carbonyl}benzyl)-4,5-dimethyl-3-oxo-2,3-dihydropyridazin-1-ium trifluoroacetate;

6-(3-{[4-(2,2-Difluoro-1-phenylethyl)-3-oxopiperazin-1-yl]carbonyl}-4-fluorobenzyl)-4,5-dimethyl-3-oxo-2,3-dihydropyridazin-1-ium trifluoroacetate;

6-(4-Fluoro-3-{[3-oxo-4-(tetrahydro-2H-pyran-3-yl)piperazin-1-yl]carbonyl}benzyl)-4,5-dimethyl-3-oxo-2,3-dihydropyridazin-1-ium trifluoroacetate;

6-(3-{[4-(4,4-Difluorocyclohexyl)-3-oxopiperazin-1-yl]carbonyl}-4-fluorobenzyl)-4,5-dimethyl-3-oxo-2,3-dihydropyridazin-1-ium trifluoroacetate;

6-(3-{[4-(3,3-Difluorocyclopentyl)-3-oxopiperazin-1-yl]carbonyl}-4-fluorobenzyl)-4,5-dimethyl-3-oxo-2,3-dihydropyridazin-1-ium trifluoroacetate;

6-(3-{[4-(4,4-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate;

6-(3-{[4-(3,3-Dimethylcyclohexyl)-3-oxopiperazin-1-yl]carbonyl}-4-fluorobenzyl)-4,5-dimethyl-3-oxo-2,3-dihydropyridazin-1-ium trifluoroacetate;

6-{3-[(4-Bicyclo[1.1.1]pent-1-yl-3-oxopiperazin-1-yl)carbonyl]-4-fluorobenzyl}-4,5-dimethyl-3-oxo-2,3-dihydropyridazin-1-ium trifluoroacetate;

6-(4-Fluoro-3-{[3-oxo-4-(1,2,3,4-tetrahydronaphthalen-1-ylmethyl)piperazin-1-yl]carbonyl}benzyl)-4,5-dimethyl-3-oxo-2,3-dihydropyridazin-1-ium trifluoroacetate;

6-[4-Fluoro-3-({4-[1-(3-isopropyl-1,2,4-oxadiazol-5-yl)ethyl]-3-oxopiperazin-1-yl}carbonyl)benzyl]-4,5-dimethyl-3-oxo-2,3-dihydropyridazin-1-ium trifluoroacetate;

6-(3-{[4-(3,3-Difluorocyclobutyl)-3-oxopiperazin-1-yl]carbonyl}-4-fluorobenzyl)-4,5-dimethyl-3-oxo-2,3-dihydropyridazin-1-ium trifluoroacetate;

6-[4-Fluoro-3-({3-oxo-4-[(4-phenyltetrahydro-2H-pyran-4-yl)methyl]piperazin-1-yl}carbonyl)benzyl]-4,5-dimethyl-3-oxo-2,3-dihydropyridazin-1-ium trifluoroacetate;

6-{3-[(4-Cyclobutyl-3-oxopiperazin-1-yl)carbonyl]-4-fluorobenzyl}-4,5-dimethyl-3-oxo-2,3-dihydropyridazin-1-ium trifluoroacetate;

6-(4-Fluoro-3-{[4-(2-fluoroethyl)-3-oxopiperazin-1-yl]carbonyl}benzyl)-4,5-dimethyl-3-oxo-2,3-dihydropyridazin-1-ium trifluoroacetate;

6-[4-Fluoro-3-({4-[2,4,3-fluorophenyl)ethyl]-3-oxopiperazin-1-yl}carbonyl)benzyl]-4,5-dimethyl-3-oxo-2,3-dihydropyridazin-1-ium trifluoroacetate;

6-{4-Fluoro-3-[(3-oxo-4-quinolin-3-ylpiperazin-1-yl)carbonyl]benzyl}-4,5-dimethylpyridazin-3(2H)-one;

3-[4-Fluoro-3-({3-oxo-4-[4-(trifluoromethyl)pyridin-2-yl]piperazin-1-yl}carbonyl)benzyl]-4,5-dimethyl-6-oxo-1,6-dihydropyridazin-1-ium trifluoroacetate;

3-(3-{[4-(1-Benzothien-3-yl)-3-oxopiperazin-1-yl]carbonyl}-4-fluorobenzyl)-4,5-dimethyl-6-oxo-1,6-dihydropyridazin-1-ium trifluoroacetate;

3-(4-Fluoro-3-{[3-oxo-4-(1,3-thiazol-5-yl)piperazin-1-yl]carbonyl}benzyl)-4,5-dimethyl-6-oxo-1,6-dihydropyridazin-1-ium trifluoroacetate;

3-{4-Fluoro-3-[(3-oxo-4-pyrimidin-5-ylpiperazin-1-yl)carbonyl]benzyl}-4,5-dimethyl-6-oxo-1,6-dihydropyridazin-1-ium trifluoroacetate;

3-[4-Fluoro-3-({3-oxo-4-[5-(trifluoromethyl)pyridin-3-yl]piperazin-1-yl}carbonyl)benzyl]-4,5-dimethyl-6-oxo-1,6-dihydropyridazin-1-ium trifluoroacetate;

6-(4-Fluoro-3-{[3-oxo-4-(3-phenylcyclohexyl)piperazin-1-yl]carbonyl}benzyl)-4,5-dimethyl-3-oxo-2,3-dihydropyridazin-1-ium trifluoroacetate;

6-[4-Fluoro-3-({3-oxo-4-[(1R,2S)-2-phenylcyclohexyl]piperazin-1-yl}carbonyl)benzyl]-4,5-dimethyl-3-oxo-2,3-dihydropyridazin-1-ium trifluoroacetate;

6-(4-Fluoro-3-{[3-oxo-4-(4-phenylcyclohexyl)piperazin-1-yl]carbonyl}benzyl)-4,5-dimethyl-3-oxo-2,3-dihydropyridazin-1-ium trifluoroacetate;

6-(4-Fluoro-3-{[3-oxo-4-(tetrahydrofuran-3-yl)piperazin-1-yl]carbonyl}benzyl)-4,5-dimethyl-3-oxo-2,3-dihydropyridazin-1-ium trifluoroacetate;

6-(4-Fluoro-3-{[3-oxo-4-(1,2,3,4-tetrahydronaphthalen-2-yl)piperazin-1-yl]carbonyl}benzyl)-4,5-dimethyl-3-oxo-2,3-dihydropyridazin-1-ium trifluoroacetate;

6-(3-{[4-(2,3-Dihydro-1H-inden-2-yl)-3-oxopiperazin-1-yl]carbonyl}-4-fluorobenzyl)-4,5-dimethyl-3-oxo-2,3-dihydropyridazin-1-ium trifluoroacetate;

6-(4-Fluoro-3-{[3-oxo-4-(2,2,2-trifluoroethyl)piperazin-1-yl]carbonyl}benzyl)-4,5-dimethyl-3-oxo-2,3-dihydropyridazin-1-ium trifluoroacetate;

6-{3-[(4-Cycloheptyl-3-oxopiperazin-1-yl)carbonyl]-4-fluorobenzyl}-4,5-dimethyl-3-oxo-2,3-dihydropyridazin-1-ium trifluoroacetate;

3-(4-Fluoro-3-{[4-(3-thienyl)piperazin-1-yl]carbonyl}benzyl)-4,5-dimethyl-6-oxo-1,6-dihydropyridazin-1-ium trifluoroacetate;

6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one;

6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one;

6-(3-{[4-(2,2-dimethyltetrahydro-2H-pyran-4-yl)-3-oxopiperazin-1-yl]carbonyl}-4-fluorobenzyl)-4,5-dimethylpyridazin-3(2H)-one trifluoroacetate;

6-{3-[(3,3-Dimethyl-5-oxo-4-phenylpiperazin-1-yl)carbonyl]-4-fluorobenzyl}-4,5-dimethylpyridazin-3(2H)-one;

3-[4-fluoro-3-(3-methyl-5-oxo-4-phenyl-piperazine-1-carbonyl)-benzyl]-4,5-dimethyl-6-oxo-1,6-dihydro-pyridazin-1-ium trifluoroacetate;

6-(4-fluoro-3-{[(3S)-3-methyl-5-oxo-4-phenylpiperazin-1-yl]carbonyl}benzyl)-4,5-dimethylpyridazin-3(2H)-one;

6-(4-fluoro-3-{[(3R)-3-methyl-5-oxo-4-phenylpiperazin-1-yl]carbonyl}benzyl)-4,5-dimethylpyridazin-3(2H)-one;

3-{4-fluoro-3-[4-(4-fluoro-phenyl)-3-methyl-5-oxo-piperazine-1-carbonyl]-benzyl}-4,5-dimethyl-6-oxo-1,6-dihydro-pyridazin-1-ium trifluoroacetate;

6-(4-fluoro-3-{[(3S)-4-(4-fluorophenyl)-3-methyl-5-oxopiperazin-1-yl]carbonyl}benzyl)-4,5-dimethylpyridazin-3(2H)-one;

6-(4-fluoro-3-{[(3R)-4-(4-fluorophenyl)-3-methyl-5-oxopiperazin-1-yl]carbonyl}benzyl)-4,5-dimethylpyridazin-3(2H)-one;

cis-3-{4-Fluoro-3-[4-(3-fluoro-cyclopentyl)-3-oxo-piperazine-1-carbonyl]-benzyl}-4,5-dimethyl-6-oxo-1,6-dihydro-pyridazin-1-ium trifluoroacetate;

6-{3-[(4-cyclopentyl-3-oxopiperazin-1-yl)carbonyl]-4-fluorobenzyl}-4-(pentafluoroethyl)pyridazin-3(2H)-one;

1-cyclopropyl-4-{5-[(4,5-dimethyl-6-oxo-1,6-dihydropyridazin-3-yl)methyl]-2-fluorobenzoyl}-1,4-diazepan-2-one;

6-{2-bromo-5-[(4-cyclopentyl-3-oxopiperazin-1-yl)carbonyl]-4-fluorobenzyl}-4,5-dimethylpyridazin-3(2H)-one;

6-{4-fluoro-3-[(6-oxohexahydropyrazino[2,1-c][1,4]oxazin-8(1H)-yl)carbonyl]benzyl}-4,5-dimethyl-3-oxo-2,3-dihydropyridazin-1-ium trifluoroacetate;

6-{4-fluoro-3-[(cis-6-methyl-4-oxooctahydro-2H-pyrido[1,2-a]pyrazin-2-yl)carbonyl]benzyl}-4,5-dimethyl-3-oxo-2,3-dihydropyridazin-1-ium trifluoroacetate;

(6S,9aS)-2-{5-[(4,5-dimethyl-6-oxo-1,6-dihydropyridazin-3-yl)methyl]-2-fluorobenzoyl}-6-methyloctahydro-4H-pyrido[1,2-a]pyrazin-4-one;

(6R,9aR)-2-{5-[(4,5-dimethyl-6-oxo-1,6-dihydropyridazin-3-yl)methyl]-2-fluorobenzoyl}-6-methyloctahydro-4H-pyrido[1,2-a]pyrazin-4-one;

6-{4-fluoro-3-[(cis-6-methyl-4-oxooctahydro-2H-pyrido[1,2-a]pyrazin-2-yl)carbonyl]benzyl}-3-oxo-4-(trifluoromethyl)-2,3-dihydropyridazin-1-ium trifluoroacetate;

(6S,9aS)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one;

(6R,9aR)-2-(2-fluoro-5-{[6-oxo-5-(trifluoromethyl)-1,6-dihydropyridazin-3-yl]methyl}benzoyl)-6-methyloctahydro-4H-pyrido[1,2-a]pyrazin-4-one;

(9aS)-2-{5-[(4,5-dimethyl-6-oxo-1,6-dihydropyridazin-3-yl)methyl]-2-fluorobenzoyl}octahydro-4H-pyrido[1,2-a]pyrazin-4-one trifluoroacetate;

(9aR)-2-{5-[(4,5-dimethyl-6-oxo-1,6-dihydropyridazin-3-yl)methyl]-2-fluorobenzoyl}octahydro-4H-pyrido[1,2-a]pyrazin-4-one trifluoroacetate;

2-(2-fluoro-5-{[6-oxo-5-(trifluoromethyl)-1,6-dihydropyridazin-3-yl]methyl}benzoyl)octahydro-4H-pyrido[1,2-a]pyrazin-4-one;

(9aS)-2-(2-fluoro-5-{[6-oxo-5-(trifluoromethyl)-1,6-dihydropyridazin-3-yl]methyl}benzoyl)octahydro-4H-pyrido[1,2-a]pyrazin-4-one;

(9aR)-2-(2-fluoro-5-{[6-oxo-5-(trifluoromethyl)-1,6-dihydropyridazin-3-yl]methyl}benzoyl)octahydro-4H-pyrido[1,2-a]pyrazin-4-one;

3-{3-[(4-cyclohexyl-2,2-dimethyl-5-oxopiperazin-1-yl)carbonyl]-4-fluorobenzyl}-4,5-dimethyl-6-oxo-1,6-dihydropyridazin-1-ium trifluoroacetate;

3-(3-{[4-(4-cyanophenyl)-3-oxopiperazin-1-yl]carbonyl}-4-fluorobenzyl)-4,5-dimethyl-6-oxo-1,6-dihydropyridazin-1-ium trifluoroacetate;

3-[4-fluoro-3-({4-[4-(methylsulfonyl)phenyl]-3-oxopiperazin-1-yl}carbonyl)benzyl]-4,5-dimethyl-6-oxo-1,6-dihydropyridazin-1-ium trifluoroacetate;

6-(3-{[4-(2,2-difluoro-1-pyridin-3-ylethyl)-3-oxopiperazin-1-yl]carbonyl}-4-fluorobenzyl)-4,5-dimethyl-3-oxo-2,3-dihydropyridazin-1-ium trifluoroacetate;

6-[4-fluoro-3-({4-[(2-methyltetrahydrofuran-2-yl)methyl]-3-oxopiperazin-1-yl}carbonyl)benzyl]-4,5-dimethyl-3-oxo-2,3-dihydropyridazin-1-ium trifluoroacetate;

6-(3-{[4-(3,4-dihydro-2H-chromen-3-yl)-3-oxopiperazin-1-yl]carbonyl}-4-fluorobenzyl)-4,5-dimethyl-3-oxo-2,3-dihydropyridazin-1-ium trifluoroacetate;

6-(4-fluoro-3-{[3-oxo-4-(1,2,3,4-tetrahydronaphthalen-1-yl)piperazin-1-yl]carbonyl}benzyl)-4,5-dimethyl-3-oxo-2,3-dihydropyridazin-1-ium trifluoroacetate;

6-(3-{[4-(2,3-dihydro-1H-inden-1-yl)-3-oxopiperazin-1-yl]carbonyl}-4-fluorobenzyl)-4,5-dimethyl-3-oxo-2,3-dihydropyridazin-1-ium trifluoroacetate;

6-[3-({4-[(1R,2R,4S)-bicyclo[2.2.1]hept-2-yl]-3-oxopiperazin-1-yl}carbonyl)-4-fluorobenzyl]-4,5-dimethyl-3-oxo-2,3-dihydropyridazin-1-ium trifluoroacetate;

6-{3-[(4-cyclopentyl-3-methyl-5-oxopiperazin-1-yl)carbonyl]-4-fluorobenzyl}-4,5-dimethyl-3-oxo-2,3-dihydropyridazin-1-ium trifluoroacetate;

6-[4-fluoro-3-({3-oxo-4-[(3S)-tetrahydro-2H-pyran-3-yl]piperazin-1-yl}carbonyl)benzyl]-4,5-dimethylpyridazin-3(2H)-one;

6-[4-fluoro-3-({3-oxo-4-[(3R)-tetrahydro-2H-pyran-3-yl]piperazin-1-yl}carbonyl)benzyl]-4,5-dimethylpyridazin-3(2H)-one;

3-{3-[(4-ethyl-3-oxopiperazin-1-yl)carbonyl]-4-fluorobenzyl}-4-methyl-6-oxo-5-(trifluoromethyl)-1,6-dihydropyridazin-1-ium trifluoroacetate;

6-(4-fluoro-3-{[4-(1-oxaspiro[4.4]non-3-yl)-3-oxopiperazin-1-yl]carbonyl}benzyl)-4,5-dimethylpyridazin-3(2H)-one trifluoroacetate;

6-(4-fluoro-3-{[4-(1-oxaspiro[4.5]dec-3-yl)-3-oxopiperazin-1-yl]carbonyl}benzyl)-4,5-dimethylpyridazin-3(2H)-one trifluoroacetate;

(9aR)-2-{5-[(4,5-dimethyl-6-oxo-1,6-dihydropyridazin-3-yl)methyl]-2-fluorobenzoyl}octahydro-4H-pyrido[1,2-a]pyrazin-4-one;

(9aS)-2-{5-[(4,5-dimethyl-6-oxo-1,6-Dihydropyridazin-3-yl)methyl]-2-fluorobenzoyl}octahydro-4H-pyrido[1,2-a]pyrazin-4-one;

6-(4-fluoro-3-{[4-(1-methylcyclohexyl)-3-oxopiperazin-1-yl]carbonyl}benzyl)-4,5-dimethyl-3-oxo-2,3-dihydropyridazin-1-ium trifluoroacetate;

6-[4-fluoro-3-({4-[1-(methylsulfonyl)piperidin-4-yl]-3-oxopiperazin-1-yl}carbonyl)benzyl]-4,5-dimethyl-3-oxo-2,3-dihydropyridazin-1-ium trifluoroacetate;

6-[4-fluoro-3-({3-oxo-4-[(3R)-tetrahydrofuran-3-yl]piperazin-1-yl}carbonyl)benzyl]-4,5-dimethylpyridazin-3(2H)-one;

6-[4-fluoro-3-({3-oxo-4-[(3S)-tetrahydrofuran-3-yl]piperazin-1-yl}carbonyl)benzyl]-4,5-dimethylpyridazin-3(2H)-one;

6-(3-{[(3S)-4-cyclopentyl-3-methyl-5-oxopiperazin-1-yl]carbonyl}-4-fluorobenzyl)-4,5-dimethylpyridazin-3(2H)-one;

6-(3-{[(3R)-cyclopentyl-3-methyl-5-oxopiperazin-1-yl]carbonyl}-4-fluorobenzyl)-4,5-dimethylpyridazin-3(2H)-one;

3-(4-fluoro-3-{[4-(1-methyl-1H-imidazol-5-yl)-3-oxopiperazin-1-yl]carbonyl}benzyl)-4,5-dimethyl-6-oxo-1,6-dihydropyridazin-1-ium trifluoroacetate;

3-(3-{[4-(2,4-dimethyl-1,3-thiazol-5-yl)-3-oxopiperazin-1-yl]carbonyl}-4-fluorobenzyl)-4,5-dimethyl-6-oxo-1,6-dihydropyridazin-1-ium trifluoroacetate;

6-[3-({4-[2,2-difluoro-1-(4-fluorophenyl)ethyl]-3-oxopiperazin-1-yl}carbonyl)-4-fluorobenzyl]-4,5-dimethyl-3-oxo-2,3-dihydropyridazin-1-ium trifluoroacetate;

6-(4-fluoro-3-{[3-oxo-4-(3-phenylcyclopentyl-piperazin-1-yl]carbonyl}benzyl)-4,5-dimethyl-3-oxo-2,3-dihydropyridazin-1-ium trifluoroacetate;

6-(4-fluoro-3-{[3-oxo-4-(tetrahydro-2H-pyran-4-yl)piperazin-1-yl]carbonyl}benzyl)-4,5-dimethyl-3-oxo-2,3-dihydropyridazin-1-ium trifluoroacetate;

6-[4-fluoro-3-({3-oxo-4-[(1R)-1-phenylethyl]piperazin-1-yl}carbonyl)benzyl]-4,5-dimethyl-3-oxo-2,3-dihydropyridazin-1-ium trifluoroacetate;

6-[4-fluoro-3-({3-oxo-4-[(1S)-1-phenylethyl]piperazin-1-yl}carbonyl)benzyl]-4,5-dimethyl-3-oxo-2,3-dihydropyridazin-1-ium trifluoroacetate;

6-(3-{[4-(2,2-difluoro-1R-phenylethyl)-3-oxopiperazin-1-yl]carbonyl}-4-fluorobenzyl)-4,5-dimethyl-3-oxo-2,3-dihydropyridazin-1-ium trifluoroacetate;

6-(3-{[4-(2,2-difluoro-1S-phenylethyl)-3-oxopiperazin-1-yl]carbonyl}-4-fluorobenzyl)-4,5-dimethyl-3-oxo-2,3-dihydropyridazin-1-ium trifluoroacetate;

3-{3-[(4-cyclohexyl-3-methyl-5-oxopiperazin-1-yl)carbonyl]-4-fluorobenzyl}-4,5-dimethyl-6-oxo-1,6-dihydropyridazin-1-ium trifluoroacetate;

6-(3-{[4-(4,4-difluorocyclohexyl)-3-methyl-5-oxopiperazin-1-yl]carbonyl}-4-fluorobenzyl)-4,5-dimethylpyridazin-3(2H)-one trifluoroacetate;

6-(3-{[4-(3,3-difluorocyclopentyl)-3-methyl-5-oxopiperazin-1-yl]carbonyl}-4-fluorobenzyl)-4,5-dimethylpyridazin-3(2H)-one trifluoroacetate;

6-(3-{[4-(4,4-dimethylcyclohexyl)-3-methyl-5-oxopiperazin-1-yl]carbonyl}-4-fluorobenzyl)-4,5-dimethylpyridazin-3(2H)-one trifluoroacetate;

6-(4-fluoro-3-{[3-methyl-5-oxo-4-(tetrahydro-2h-pyran-3-yl)piperazin-1-yl]carbonyl}benzyl)-4,5-dimethylpyridazin-3(2H)-one trifluoroacetate;

6-(4-fluoro-3-{[3-methyl-5-oxo-4-(tetrahydrofuran-3-yl)piperazin-1-yl]carbonyl}benzyl)-4,5-dimethylpyridazin-3(2H)-one trifluoroacetate;

6-(3-{[4-(2,2-difluoro-1-phenylethyl)-3-methyl-5-oxopiperazin-1-yl]carbonyl}-4-fluorobenzyl)-4,5-dimethylpyridazin-3(2H)-one trifluoroacetate;

6-(3-{[4-(3,4-dihydro-2H-chromen-3-yl)-3-methyl-5-oxopiperazin-1-yl]carbonyl}-4-fluorobenzyl)-4,5-dimethylpyridazin-3(2H)-one trifluoroacetate;

4-ethyl-6-(4-fluoro-3-{[3-oxo-4-(tetrahydro-2H-pyran-3-yl)piperazin-1-yl]carbonyl}benzyl)-3-oxo-2,3-dihydropyridazin-1-ium trifluoroacetate;

4-ethyl-6-(4-fluoro-3-{[3-oxo-4-(2,2,2-trifluoroethyl)piperazin-1-yl]carbonyl}benzyl)-3-oxo-2,3-dihydropyridazin-1-ium trifluoroacetate;

3-(4-fluoro-3-{[(9aS)-4-oxooctahydro-2H-pyrido[1,2-a]pyrazin-2-yl]carbonyl}benzyl)-4-methyl-6-oxo-5-(trifluoromethyl)-1,6-dihydropyridazin-1-ium trifluoroacetate;

3-{4-fluoro-3-[(6-oxohexahydropyrazino[2,1-c][1,4]oxazin-8(1H)-yl)carbonyl]benzyl}-4-methyl-6-oxo-5-(trifluoromethyl)-1,6-dihydropyridazin-1-ium trifluoroacetate;

6-{3-[(4-ethyl-3-methyl-5-oxopiperazin-1-yl)carbonyl]-4-fluorobenzyl}-4,5-dimethyl-3-oxo-2,3-dihydropyridazin-1-ium trifluoro acetate;

6-(4-fluoro-3-{[4-(4-methoxybenzyl)-3-methyl-5-oxopiperazin-1-yl]carbonyl}benzyl)-4,5-dimethyl-3-oxo-2,3-dihydropyridazin-1-ium trifluoroacetate;

6-(4-fluoro-3-{[3-methyl-5-oxo-4-(2,2,2-trifluoroethyl)piperazin-1-yl]carbonyl}benzyl)-4,5-dimethyl-3-oxo-2,3-dihydropyridazin-1-ium trifluoroacetate;

6-[3-({4-[(1R,4S)-bicyclo[2.2.1]hept-2-yl]-3-methyl-5-oxopiperazin-1-yl}carbonyl)-4-fluorobenzyl]-4,5-dimethyl-3-oxo-2,3-dihydropyridazin-1-ium trifluoroacetate;

3-(4-fluoro-3-{[3-oxo-4-(tetrahydro-2h-pyran-3-yl)piperazin-1-yl]carbonyl}benzyl)-4-methyl-6-oxo-5-(trifluoromethyl)-1,6-dihydropyridazin-1-ium trifluoroacetate;

3-(4-fluoro-3-{[3-oxo-4-(tetrahydrofuran-3-yl)piperazin-1-yl]carbonyl}benzyl)-4-methyl-6-oxo-5-(trifluoromethyl)-1,6-dihydropyridazin-1-ium trifluoroacetate;

6-{3-[(4-ethyl-3-oxopiperazin-1-yl)carbonyl]-4-fluorobenzyl}-5-methyl-4-(trifluoromethyl)pyridazin-3(2H)-one;

4-ethyl-6-[4-fluoro-3-[{3-oxo-4-[(3S)-tetrahydro-2H-pyran-3-yl]piperazin-1-yl}carbonyl)benzyl]pyridazin-3(2H)-one;

4-ethyl-6-[4-fluoro-3-({3-oxo-4-[(3R)-tetrahydro-2H-pyran-3-yl]piperazin-1-yl}carbonyl)benzyl]pyridazin-3(2H)-one;

3-(4-fluoro-3-{[3-oxo-4-(tetrahydro-2H-pyran-4-yl)piperazin-1-yl]carbonyl}benzyl)-4-methyl-6-oxo-5-(trifluoromethyl)-1,6-dihydropyridazin-1-ium trifluoroacetate;

3-{3-[(4-ethyl-3-methyl-5-oxopiperazin-1-yl)carbonyl]-4-fluorobenzyl}-4-methyl-6-oxo-5-(trifluoromethyl)-1,6-dihydropyridazin-1-ium trifluoroacetate;

4-ethyl-6-(4-fluoro-3-{[3-oxo-4-(1,2,3,4-tetrahydronaphthalen-2-yl)piperazin-1-yl]carbonyl}benzyl)pyridazin-3(2H)-one;

6-{3-[(4-cyclopentyl-3-oxopiperazin-1-yl)carbonyl]-4-fluorobenzyl}-3-oxo-4-(pentafluoroethyl)-2,3-dihydropyridazin-1-ium trifluoroacetate;

6-(4-fluoro-3-{[4-(3-fluorocyclopentyl)-3-oxopiperazin-1-yl]carbonyl}benzyl)-4,5-dimethylpyridazin-3(2H)-one;

6-(3-{[(3R)-4-cyclopentyl-3-methyl-5-oxopiperazin-1-yl]carbonyl}-4-fluorobenzyl)-4-(trifluoromethyl)pyridazin-3(2H)-one;

6-(3-{[(3S)-4-cyclopentyl-3-methyl-5-oxopiperazin-1-yl]carbonyl}-4-fluorobenzyl)-4-(trifluoromethyl)pyridazin-3(2H)-one;

6-[4-fluoro-3-({3-oxo-4-[(3S)-tetrahydro-2H-pyran-3-yl]piperazin-1-yl}carbonyl)benzyl]-4-(trifluoromethyl)pyridazin-3(2H)-one;

6-[4-fluoro-3-({3-oxo-4-[(3R)-tetrahydro-2H-pyran-3-yl]piperazin-1-yl}carbonyl)benzyl]-4-(trifluoromethyl)pyridazin-3(2H)-one;

6-(3-{[(3S)-4-ethyl-3-methyl-5-oxopiperazin-1-yl]carbonyl}-4-fluorobenzyl)-5-methyl-4-(trifluoromethyl)pyridazin-3(2H)-one;

6-(3-{[(3R)-4-ethyl-3-methyl-5-oxopiperazin-1-yl]carbonyl}-4-fluorobenzyl)-5-methyl-4-(trifluoromethyl)pyridazin-3(2H)-one;

6-[4-fluoro-3-({(3S)-3-methyl-5-oxo-4-[(3S)-tetrahydrofuran-3-yl]piperazin-1-yl}carbonyl)benzyl]-4,5-dimethylpyridazin-3(2H)-one;

6-[4-fluoro-3-({(3R)-3-methyl-5-oxo-4-[(3S)-tetrahydrofuran-3-yl]piperazin-1-yl}carbonyl)benzyl]-4,5-dimethylpyridazin-3(2H)-one;

4-ethyl-6-(4-fluoro-3-{[3-oxo-4-[(2S)-1,2,3,4-tetrahydronaphthalen-2-yl]piperazin-1-yl}carbonyl)benzyl]pyridazin-3(2H)-one;

4-ethyl-6-(4-fluoro-3-{[3-oxo-4-[(2R)-1,2,3,4-tetrahydronaphthalen-2-yl]piperazin-1-yl}carbonyl)benzyl]pyridazin-3(2H)-one;

6-[4-Fluoro-3-({4-[(1S)-1-methylpropyl]-3-oxopiperazin-1-yl}carbonyl)benzyl]-4,5-dimethylpyridazin-3(2H)-one;

6-(4-Fluoro-3-{[4-(2-methoxy-1-methylethyl)-3-oxopiperazin-1-yl]carbonyl}benzyl)-4,5-dimethylpyridazin-3(2H)-one;

6-{3-[(4-Cyclobutyl-3-methyl-5-oxopiperazin-1-yl)carbonyl]-4-fluorobenzyl}-4,5-dimethylpyridazin-3(2H)-one;

6-{3-[(4-Cyclobutyl-3-ethyl-5-oxopiperazin-1-yl)carbonyl]-4-fluorobenzyl}-4,5-dimethylpyridazin-3(2H)-one;

6-(3-{[4-(3-Chlorophenyl)-3-methyl-5-oxopiperazin-1-yl]carbonyl}-4-fluorobenzyl)-4,5-dimethylpyridazin-3(2H)-one;

4-((2S)-4-{5-[(4,5-Dimethyl-6-oxo-1,6-dihydropyridazin-3-yl)methyl]-2-fluorobenzoyl}-2-methyl-6-oxopiperazin-1-yl)benzonitrile;

6-(3-{[4-(1-Ethylpropyl)-3-oxopiperazin-1-yl]carbonyl}-4-fluorobenzyl)-4,5-dimethylpyridazin-3(2H)-one;

6-[4-Fluoro-3-({4-[(1R)-1-methylpropyl]-3-oxopiperazin-1-yl}carbonyl)benzyl]-4,5-dimethylpyridazin-3(2H)-one;

6-[4-Fluoro-3-({4-[(1S)-2-methoxy-1-methylethyl]-3-oxopiperazin-1-yl}carbonyl)benzyl]-4,5-dimethylpyridazin-3(2H)-one;

6-(4-Fluoro-3-{[4-(2-methoxyethyl)-3-oxopiperazin-1-yl]carbonyl}benzyl)-4,5-dimethylpyridazin-3(2H)-one;

6-(3-{[4-(2-Ethoxyethyl)-3-oxopiperazin-1-yl]carbonyl}-4-fluorobenzyl)-4,5-dimethylpyridazin-3(2H)-one;

6-(4-Fluoro-3-{[4-(2-isopropoxyethyl)-3-oxopiperazin-1-yl]carbonyl}benzyl)-4,5-dimethylpyridazin-3(2H)-one;

6-(4-Fluoro-3-{[4-(2-hydroxy-2-methylpropyl)-3-oxopiperazin-1-yl]carbonyl}benzyl)-4,5-dimethylpyridazin-3(2H)-one;

4-((2S)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-(3-{[(3R)-4-Cyclobutyl-3-methyl-5-oxopiperazin-1-yl]carbonyl}-4-fluorobenzyl)-4,5-dimethylpyridazin-3(2H)-one;

6-(3-{[(3S)-4-Cyclobutyl-3-methyl-5-oxopiperazin-1-yl]carbonyl}-4-fluorobenzyl)-4,5-dimethylpyridazin-3(2H)-one;

6-(3-{[(3S)-4-(3-Chlorophenyl)-3-methyl-5-oxopiperazin-1-yl]carbonyl}-4-fluorobenzyl)-4,5-dimethylpyridazin-3(2H)-one;

6-(3-{[(3R)-4-(3-Chlorophenyl)-3-methyl-5-oxopiperazin-1-yl]carbonyl}-4-fluorobenzyl)-4,5-dimethylpyridazin-3(2H)-one;

6-[4-Fluoro-3-({4-[(1R)-2-methoxy-1-methylethyl]-3-oxopiperazin-1-yl}carbonyl)benzyl]-4,5-dimethylpyridazin-3(2H)-one;

6-(3-{[(3R)-4-Cyclobutyl-3-ethyl-5-oxopiperazin-1-yl]carbonyl}-4-fluorobenzyl)-4,5-dimethylpyridazin-3(2H)-one;

6-(3-{[(3S)-4-Cyclobutyl-3-ethyl-5-oxopiperazin-1-yl]carbonyl}-4-fluorobenzyl)-4,5-dimethylpyridazin-3(2H)-one;

6-[3-({4-[(1R)-1,2-Dimethylpropyl]-3-oxopiperazin-1-yl}carbonyl)-4-fluorobenzyl]-4,5-dimethylpyridazin-3(2H)-one;

6-[3-({4-[(1S)-1,2-Dimethylpropyl]-3-oxopiperazin-1-yl}carbonyl)-4-fluorobenzyl]-4,5-dimethylpyridazin-3(2H)-one;

6-{3-[(4-Cyclohexyl-3-ethyl-5-oxopiperazin-1-yl)carbonyl]-4-fluorobenzyl}-4,5-dimethylpyridazin-3(2H)-one;

6-{3-[(4-Cyclopentyl-3-isobutyl-5-oxopiperazin-1-yl)carbonyl]-4-fluorobenzyl}-4,5-dimethylpyridazin-3(2H)-one;

6-{3-[(4-Cyclopentyl-3-ethyl-5-oxopiperazin-1-yl)carbonyl]-4-fluorobenzyl}-4,5-dimethylpyridazin-3(2H)-one;

6-(3-{[(3R)-4-(4-Chloro-3-fluorophenyl)-3-methyl-5-oxopiperazin-1-yl]carbonyl}-4-fluorobenzyl)-4,5-dimethylpyridazin-3(2H)-one;

6-(3-{[4-(3,3-Difluorocyclobutyl)-3-methyl-5-oxopiperazin-1-yl]carbonyl}-4-fluorobenzyl)-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)benzonitrile;

6-(3-{[(3R)-4-(3-Chlorophenyl)-3-methyl-5-oxopiperazin-1-yl]carbonyl}-4-fluorobenzyl)-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-[4-Fluoro-3-({3-oxo-4-[(1S)-2,2,2-trifluoro-1-methylethyl]piperazin-1-yl}carbonyl)benzyl]-4,5-dimethylpyridazin-3(2H)-one;

6-(3-{[(3R)-4-(3S-Difluorophenyl)-3-methyl-5-oxopiperazin-1-yl]carbonyl}-4-fluorobenzyl)-4,5-dimethylpyridazin-3(2H)-one;

6-(3-{[(3R)-4-(4-Chlorophenyl)-3-methyl-5-oxopiperazin-1-yl]carbonyl}-4-fluorobenzyl)-4,5-dimethylpyridazin-3(2H)-one;

6-(4-Fluoro-3-{[(3R)-3-methyl-5-oxo-4-(2-thienyl)piperazin-1-yl]carbonyl}benzyl)-4,5-dimethylpyridazin-3(2H)-one;

6-(3-{[(3R)-4-(4-Chloro-2-fluorophenyl)-3-methyl-5-oxopiperazin-1-yl]carbonyl}-4-fluorobenzyl)-4,5-dimethylpyridazin-3(2H)-one;

5-((2R)-4-{5-[(4,5-Dimethyl-6-oxo-1,6-dihydropyridazin-3-yl)methyl]-2-fluorobenzoyl}-2-methyl-6-oxopiperazin-1-yl)-2-fluorobenzonitrile;

6-(3-{[(3R)-4-(3-Chloro-5-fluorophenyl)-3-methyl-5-oxopiperazin-1-yl]carbonyl}-4-fluorobenzyl)-4,5-dimethylpyridazin-3(2H)-one;

6-(3-{[(3R)-4-(3-Chloro-4-fluorophenyl)-3-methyl-5-oxopiperazin-1-yl]carbonyl}-4-fluorobenzyl)-4,5-dimethylpyridazin-3(2H)-one;

6-[4-Fluoro-3-({3-oxo-4-[(1R)-2,2,2-trifluoro-1-methylethyl]piperazin-1-yl}carbonyl)benzyl]-4,5-dimethylpyridazin-3(2H)-one;

4-((2R)-4-{5-[(4,5-Dimethyl-6-oxo-1,6-dihydropyridazin-3-yl)methyl]-2-fluorobenzoyl}-2-methyl-6-oxopiperazin-1-yl)-3-fluorobenzonitrile;

3-((2R)-4-{5-[(4,5-Dimethyl-6-oxo-1,6-dihydropyridazin-3-yl)methyl]-2-fluorobenzoyl}-2-methyl-6-oxopiperazin-1-yl)-5-fluorobenzonitrile;

6-(3-{[(3R)-4-(3,4-Difluorophenyl)-3-methyl-5-oxopiperazin-1-yl]carbonyl}-4-fluorobenzyl)-4,5-dimethylpyridazin-3(2H)-one;

6-(3-{[4-(1-Cyclopropylethyl)-3-oxopiperazin-1-yl]carbonyl}-4-fluorobenzyl)-4,5-dimethylpyridazin-3(2H)-one;

6-(3-{[(3R)-4-(5-Chloro-2-fluorophenyl)-3-methyl-5-oxopiperazin-1-yl]carbonyl}-4-fluorobenzyl)-4,5-dimethylpyridazin-3(2H)-one;

6-(3-{[(3R)-4-(3-Chloro-2-fluorophenyl)-3-methyl-5-oxopiperazin-1-yl]carbonyl}-4-fluorobenzyl)-4,5-dimethylpyridazin-3(2H)-one;

6-(3-{[(3R)-4-Cyclopentyl-3-isopropyl-5-oxopiperazin-1-yl]carbonyl}-4-fluorobenzyl)-4,5-dimethylpyridazin-3(2H)-one;

6-(3-{[(3S)-4-(4-Chloro-3-fluorophenyl)-3-methyl-5-oxopiperazin-1-yl]carbonyl}-4-fluorobenzyl)-4,5-dimethylpyridazin-3(2H)-one;

6-(3-{[(3S)-4-(3,3-Difluorocyclobutyl)-3-methyl-5-oxopiperazin-1-yl]carbonyl}-4-fluorobenzyl)-4,5-dimethylpyridazin-3(2H)-one;

6-(3-{[(3R)-4-(3,3-Difluorocyclobutyl)-3-methyl-5-oxopiperazin-1-yl]carbonyl}-4-fluorobenzyl)-4,5-dimethylpyridazin-3(2H)-one;

6-{4-Fluoro-3-[(4-isopropyl-3-oxopiperazin-1-yl)carbonyl]benzyl}-4,5-dimethylpyridazin-3(2H)-one;

6-[4-Fluoro-3-({4-[(trans)-3-fluorocyclopentyl]-3-oxopiperazin-1-yl}carbonyl)benzyl]-4,5-dimethylpyridazin-3(2H)-one;

or a pharmaceutically acceptable salt, stereoisomer, free base or tautomer thereof.

11. A pharmaceutical composition comprising a compound of claim 1, or a pharmaceutically acceptable salt, stereoisomer or tautomer thereof in association with a pharmaceutically acceptable carrier.

12. A combination of a compound of claim 1, or a pharmaceutically acceptable salt, stereoisomer or tautomer thereof and an anti-cancer agent for simultaneous, separate or sequential administration.

* * * * *